United States Patent
Ouzunova et al.

(10) Patent No.: US 11,345,923 B2
(45) Date of Patent: May 31, 2022

(54) COLD-TOLERANT PLANT

(71) Applicant: KWS SAAT SE & CO. KGAA, Einbeck (DE)

(72) Inventors: Milena Ouzunova, Göttingen (DE); Thomas Presterl, Einbeck (DE); Carsten Knaak, Göttingen (DE); Daniela Scheuermann, Einbeck (DE); Claude Urbany, Einbeck (DE); Peter Westhoff, Neuss (DE); Elena Pestsova, Wuppertal (DE); Karin Ernst, Düsseldorf (DE)

(73) Assignee: KWS SAAT SE & Co. KGaA, Einbeck (DE)

( * ) Notice: Subject to any disclaimer, the term of this patent is extended or adjusted under 35 U.S.C. 154(b) by 0 days.

(21) Appl. No.: 15/779,328

(22) PCT Filed: Nov. 26, 2016

(86) PCT No.: PCT/EP2016/078920
§ 371 (c)(1),
(2) Date: May 25, 2018

(87) PCT Pub. No.: WO2017/089601
PCT Pub. Date: Jun. 1, 2017

(65) Prior Publication Data
US 2018/0371486 A1  Dec. 27, 2018

(30) Foreign Application Priority Data
Nov. 27, 2015  (EP) .................... 15196721

(51) Int. Cl.
*C12N 15/82* (2006.01)
*C12Q 1/6895* (2018.01)
*C07K 14/415* (2006.01)

(52) U.S. Cl.
CPC ........ *C12N 15/8273* (2013.01); *C07K 14/415* (2013.01); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 5,352,605 A | 10/1994 | Fraley et al. | |
| 5,847,102 A | 12/1998 | Singh et al. | |
| 2007/0044171 A1 | 2/2007 | Kovalic et al. | |
| 2009/0068163 A1 | 3/2009 | Klebsattal et al. | |
| 2010/0115670 A1 | 5/2010 | Christensen | |

FOREIGN PATENT DOCUMENTS

| | | |
|---|---|---|
| DE | 10 2005 021 365 A1 | 11/2006 |
| DE | 10 2013 014 637 | 3/2015 |
| EP | 2 116 606 A1 | 11/2009 |
| WO | 00/026388 | 5/2000 |
| WO | 02/48378 | 6/2002 |
| WO | 03/006660 A1 | 1/2003 |
| WO | 03/008596 | 1/2003 |
| WO | WO2008/034648 A1 | 3/2008 |
| WO | 2008/148298 A1 | 12/2008 |
| WO | 2010/079430 A1 | 7/2010 |
| WO | 2011/072246 | 6/2011 |
| WO | 2014/104878 A1 | 7/2014 |
| WO | WO2014/160304 A1 | 10/2014 |

OTHER PUBLICATIONS

Gen Bank Accession XM_008680084, dated Aug. 2, 2014. (Year: 2014).*
Gen Bank Accession EU959260, dated Dec. 10, 2008. (Year: 2008).*
Baliashvili, Nino. Feinkartierung eines QTL (Quantitative Trait Locus) für Kühletoleranz auf Chromosom 4 in Mais und dessen molekularbiologische und phänotypische Charakterisierung. Diss. Universitäts-und Landesbibliothekder Heinrich-Heine-Universität Düsseldorf 2011. (Year: 2011).*
Pozniak et al. (Theoretical and Applied Genetics 114.3 (2007): 525-537). (Year: 2007).*
Guo et al. (Theoretical and applied genetics 127.10 (2014): 2149-2158). (Year: 2014).*
Tao et al. (BMC Plant Biology 13.1 (2013): 1-13). (Year: 2013).*
Baliashvili, Nino. Feinkartierung eines QTL (Quantitative Trait Locus) für Kühletoleranz auf Chromosom 4 in Mais und dessen molekularbiologische und phänotypische Charakterisierung. Diss. Universitäts-und Landesbibliothekder Heinrich-Heine-Universität Düsseldorf 2011. (Year: 2011).*
Database EMBL [online], "Zea mays clone 213309 SAUR31—auxin-responsive SAUR family member mRNA, complete cds.", XP002757915,gefunden im EBI accession No. EMBL:EU959560, Oct. 31, 2008, 3 pages.
Nickolai N. Alexandrov et al., "Insights into corn genes derived from large-scale cDNA sequencing", Plant Mol Biol (2009) 69:179-194.
"Amino acid sequence SEQ ID 90823.", XP002757920, retrieved from EBI accession No. GSP:AWK17619 Database accession No. AWK17619 sequence Oct. 29, 2009 (Oct. 29, 2009).

(Continued)

*Primary Examiner* — Charles Logsdon
(74) *Attorney, Agent, or Firm* — Troutman Pepper Hamilton Sanders LLP

(57) ABSTRACT

The present invention relates to the identification and molecular characterization as well as to the use of genes and markers from a chromosomal interval which has a locus for cold tolerance in maize. The invention further relates to the development of molecular markers for assisting in growth, in particular for preventing a fixing of a "selective sweep" in a region with a low recombination rate, and to the provision of transgenic and non-transgenic plants, in particular maize plants, which show a newly mediated or increased cold tolerance.

3 Claims, 6 Drawing Sheets

Figure 1:
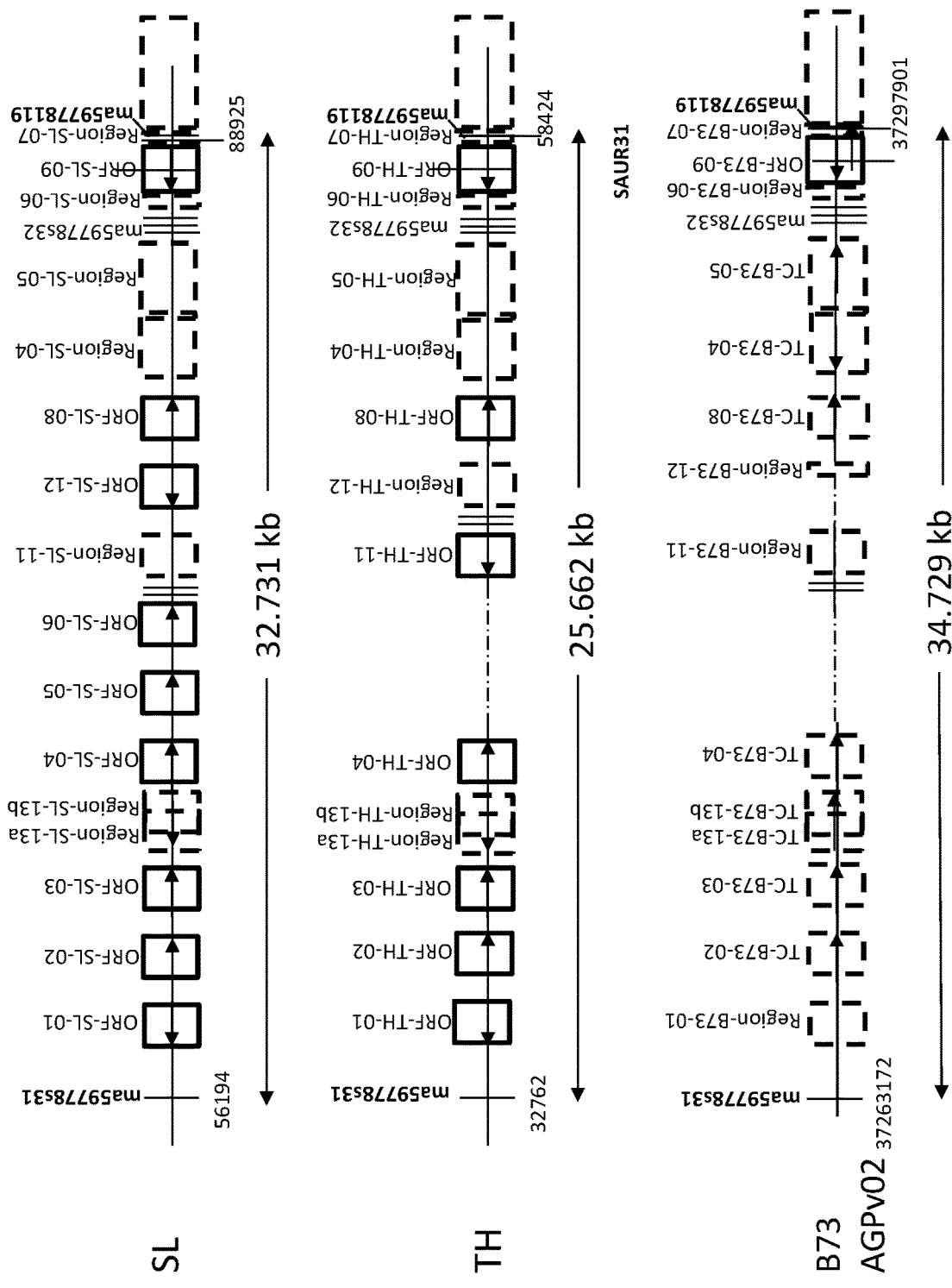

Specification includes a Sequence Listing.

(56) References Cited

OTHER PUBLICATIONS

Baliashvili, "Feinkartierung eines QTL (Quantitative Trait Locus) fUr KUhletoleranz auf Chromosom 4 in Mais und dessen molekularbiologische und phanotypische Charakterisierung. Inaugural-Dissertation zur Erlangung des Doktorgrades der Mathematisch-Naturwissenschaftlichen Fakultat der Heinrich-Heine-Universitat", Jan. 2011, pp. I-V, 1-96, XP055273945, Dusseldorf, Germany.
Cai, G. et al., "ZmMKKI, a novel group A mitogen-activated protein kinase kinase gene in maize, conferred chilling stress tolerance and was involved in pathogen defense in transgenic tobacco", Plant Science, vol. 214, Oct. 4, 2013 (Oct. 4, 2013), pp. 57-73.
Chen, Y. et al., "Small auxin upregulated RNA (SAUR) gene family in maize: Identification, evolution, and its ohylogenetic comparison with Arabidopsis , rice, and sorghum", Journal of Integrative Plant Biology, vol. 56, No. 2, Nov. 8, 2013 (Nov. 8, 2013), pp. 133-150.
European Search Report dated May 23, 2016 for EP Application No. 15196721.3.
Greaves, J.A., "Improving suboptimal temperature tolerance in maize—the search for variation", Journal of Experimental Botany, vol. 47, No. 296, Mar. 1996, pp. 307-323.
International Preliminary Report on Patentability issued from the International Searching Authority dated May 29, 2018 for International Application No. PCT/EP2016/078920.
International Search Report issued from the International Searching Authority dated May 17, 2017 for International Application No. PCT/EP2016/078920.
Marocco, A. et al., "Chilling Stress in Maize", Maydica, 2005, vol. 50, pp. 571-580.
"Nucleotide sequence SEQ ID 90822 ", XP002757919, retrieved from EBI accession No. GSN:AWK17618 Database accession No. AWK17618 sequence & Database Geneseq [Online] Oct. 29, 2009 (Oct. 29, 2009).
Ludwig, Y. et al., "The Maize (Zea mays L.) Auzin/Indole-3-Acetic AcidGene Family: Phylogeny, Synteny, and Unique Root-Type and Tissue-Specific Expression Patterns during Development", PLOS One, (2013) vol. 8, Issue 11, e78859, pp. 1-12.
Rincent, R. et al., "Dent and Flint maize diversity panels reveial important genetic potential for increasing biomass production", Theor Appl Genet (2014), vol. 127; pp. 2313-2331.
Rodriguez, V.M. et al., "Identification of quantitative trait loci involved in the response to cold stress in maize (Zea mays L.)", Molecular Breeding: New Strategies in Plant Improvement, vol. 33(2),pp. 363-371, Sep. 20, 2013.
Sobkowiak, A. et al., "Genome-wide transcriptomic analysis of response to low temperature reveals candidate genes determining divergent cold-sensitivity of maize inbred lines", Plant Molecular Biology, Springer, Dordrecht, NL, vol. 85, No. 3, Mar. 13, 2014, pp. 317-331.
Strigens, A. et al., "Association mapping for chilling tolerance in elite flint and dent maize inbred lines evaluated in growth chamber and field experiments" Plant Cell and Environment, vol. 36, No. 10, May 13, 2013, pp. 1871-1887.
Weckwerth, P. et al., "Zm CPKI, a calcium-independent kinase member of the Zea mays CDPK gene family, functions as a negative regulator in cold stress signalling", Plant Cell and Environment, vol. 38, No. 3, pp. 544-558, Aug. 22, 2014.
Written Opinion of the International Searching Authority dated May 17, 2017 for International Application No. PCT/EP2016/078920.
Bhosale et al., "Chilling Tolerance of Central European Maize Lines and their Factorial Crosses", Annals of Botany, 2007, vol. 100, pp. 1315-1321.
Fracheboud et al. "Identification of quantitative trait loci for cold-tolerance of photosynthesis in maize (Zea mays L.)", Journal of Experimental Botany, 2002, vol. 53, No. 376, pp. 1967-1977.
Fracheboud et al., "Genetic analysis of cold-tolerance of photosynthesis in maize", Plant Molecular Biology, 2004, vol. 56, No. 2, pp. 241-253.
Hund et al., "QTL controlling root and shoot traits of maize seedlings under cold stress", Theoretical and Applied Genetics, 2004, vol. 109, No. 3, pp. 618-629.
Hund et al. "Cold tolerance of the photosynthetic apparatus: pleiotropic relationship between photosynthetic performance and specific leaf area of maize seedlings", Molecular Breeding, 2005, vol. 16, No. 4, pp. 321-331.
Guerra-Peraza et al., "Temperature at night affects the genetic control of acclimation to cold in maize seedlings", Maydica, 2012, vol. 56, No. 4, pp. 367-377.
Leipner et al., "QTL studies reveal little relevance of chilling-related seedling traits for yield in maize", Theor Appl Genet, 2008, No. 116, pp. 555-562.
Jompuk et al., "Mapping of quantitative trait loci associated with chilling tolerance in maize (Zea mays L.) seedlings grown under field conditions", Journal of Experimental Botany, 2005, vol. 56, No. 414, pp. 1153-1163.
Presterl et al., "Quantitative trait loci for early plant vigour of maize grown in chilly environments", Theoretical and Applied Genetics, 2007, vol. 114, No. 6, pp. 1059-1070.
Rodriguez et al., Effects of selection for color intensity on antioxidant capacity in maize (Zea mays L.), Euphytica, 2013, vol. 193, No. 3, pp. 339-345.
Stam et al., "The theoretical proportion of the donor genome in near-isogenic lines of self-fertilizers bred by backcrossing", Euphytica, 1981, vol. 30, No. 2, pp. 227-238.
Zeven et al., Investigation of linkage drag in near isogenic lines of wheat by testing for seedling reaction to races of stem rust, leaf rust and yellow rust:, Euphytica, 1983, vol. 32, No. 2, pp. 319-327.
Ma et al., "COLD1 confers chilling tolerance in rice", Cell, 2015, vol. 160, No. 6, pp. 1209-1221.
Xu et al., "Multiple auxin response modules in the soybean SAUR 15A promoter", Plant Science, 1997, vol. 126, No. 2, pp. 193-201.
Jain et al., "Genome-wide analysis, evolutionary expansion, and expression of early auxin-responsive SAUR gene family in rice (Oryza sativa)". Genomics, 2006, vol. 88, No. 3, pp. 360-371.
Jain et al., "Transcript profiling reveals diverse roles of auxin-responsive genes during reproductive development and abiotic stress in rice", The Febs Journal, 2009, vol. 276, No. 11, p. 3148¬3162.
Hou et al., "SAUR36, a small auxin up RNA gene, is involved in the promotion of leaf senescence in Arabidopsis", Plant Physiology, 2013, vol. 161, No. 2, pp. 1002-1009.
Chen et al., "Small auxin upregulated RNA (SAUR) gene family in maize: Identification, evolution, and its phylogenetic comparison with Arabidopsis, rice, and sorghum", Journal of Integrative Plant Biology, 2014, vol. 56, Issue 2, pp. 133-150.
Miki et al., "Selectable marker genes in transgenic plants: applications, alternatives and biosafety", Journal of Biotechnology, 2004, vol. 107, No. 3, pp. 193-232.
Kobayashi et al., "Flower-specific gene expression directed by the promoter of a chaicone synthase gene from Gentiana triflora in Petunia hybrida". Plant Science, 1998, vol. 131, No. 2, pp. 173-180.
Gurr et al., "Engineering plants with increased disease resistance: what are we going to express?", TRENDS in Biotechnology, 2005, vol. 23, No. 6, pp. 275-282.
Venter, "Synthetic promoters: genetic control through cis engineering", Trends in Plant Science, 2007, vol. 12, No. 3, pp. 118-124.
Das et al., "Site-selected transposon mutagenesis at the hcf106 locus in maize", The Plant Cell, 1995, vol. 7, No. 3, pp. 287-294.
Till et al., "Discovery of induced point mutations in maize genes by Tilling", BMC Plant Biology, 2004, vol. 4, No. 1, pp. 12, 8 pages.
McCarty et al., "Steady-state transposon mutagenesis in inbred maize", The Plant Journal, 2005, vol. 44, No. 1, pp. 52-61.
Stoddard, "Homing endonucleases: from microbial genetic Invaders to reagents for targeted DNA modification", Structure, 2011, vol. 19, No. 1, pp. 7-15.
Lloyd et al., "Targeted mutagenesis using zinc-finger nucleases in Arabidopsis", PNAS, 2005, vol. 102, No. 6, pp. 2232-2237.
Silva et al., "Meganucleases and other tools for targeted genome engineering: perspectives and challenges for gene therapy", Current Gene Therapy, 2011, vol. 11, No. 1, pp. 11-27.

(56) References Cited

OTHER PUBLICATIONS

Gaj et al., "ZFN, TALEN, and CRISPR/Cas-based methods for genome engineering", Trends in Biotechnology, 2013, No. 31, No. 7, pp. 397-405.

Meihis et al., "Natural variation In maize aphid resistance is associated with 2,4-dihydroxy-7-methoxy-1, 4-benzoxazin-3-one glucoside methyltransferase activity", The Plant Cell, 2013, vol. 25. No. 6, pp. 2341-2355.

Butelli et al., "Retrotransposons control fruit-specific, cold-dependent accumulation of anthocyanins in blood oranges", The Plant Cell, 2012, vol. 24, No. 3, pp. 1242-1255.

Spartz et al., "The SAUR19 subfamily of Small Auxin up RNA genes promote cell expansion", The Plant Journal, 2012, vol. 70, No. 6, pp. 978-990.

Odell et al., "Identification of DNA sequences required for activity of the cauliflower mosaic virus 35S promoter", Nature, 1985, vol. 313, pp. 810-812.

\* cited by examiner

SEQUENCE LISTING

<160> NUMBER OF SEQ ID NOS: 38

<210> SEQ ID NO 1
<211> LENGTH: 2016

<212> TYPE: DNA
<213> ORGANISM: Zea mays

<400> SEQUENCE: 1

| | | | | | | |
|---|---|---|---|---|---|---|
| atggcgcccc | cgagagtgga | agacccatg | gcgctgttgt | tggccaaaat | cgatgaaggc | 60 |
| agtaaggaaa | cctgccgacg | catggaggca | atccattcta | caatggagaa | gatggagatc | 120 |
| acagtgcaag | gactggtctc | caatcagagc | gacttcaaga | agtggcagcc | cgagatcgag | 180 |
| aggaaggtgg | tggagatggc | ggaaacccta | gtgaagatcc | aaacgaagat | aagtaatacg | 240 |
| accccgtcta | ccacttcttc | gggagcagta | ccagcggtcg | ccaacgtctc | gatgtcggaa | 300 |
| acagcttcgg | tggtggtggg | ggagaagatg | gcgggttcta | ccctgcaccg | tacggcggat | 360 |
| cccttccgac | gacctgctgc | cgaatcgaag | gtgaaccaga | tgtcgctgcc | cttgggaggt | 420 |
| atggccacgc | ctaatcctca | tgctccttgg | ttattcggcc | aaacctctgt | gagtcccttt | 480 |
| gcatctccaa | cctggtcaca | aggattggga | ggaaacatgc | caccgatgaa | ttttccagtg | 540 |
| tttgatgcat | ccaatcctaa | gctatggaaa | atcggtgtg | aaacttattt | tgagtactat | 600 |
| gctgtcctag | tggatatgtg | gattcgattg | gctatcatgc | actttgaggg | gccgactcta | 660 |
| ttttggctgc | agtatatgga | aggtagaacg | agggaaatga | attggggtga | actttgtgca | 720 |
| gctctgctca | ccagattcgg | tcgtgaccag | cataatttgc | tcactagaca | attttaccat | 780 |
| atattccaga | caggatcagt | atcagattat | attgaacaat | ttgatttgtt | attgcatcag | 840 |
| ttgttggctc | atgaaaatca | tctcaccact | accatggtta | ctgcccgttt | tgttgatgga | 900 |
| ctgaaagacg | aactaagggc | agcggtaatc | atacagcggc | cagctgattt | ggatacaaca | 960 |
| tgttctctaa | cattattaca | agaagaggtc | atgagtactt | ccggacgtag | agaactgaga | 1020 |
| aaagtggata | ctaactccat | tgtcagagtt | ccaaacaaac | ccaatgcctt | gcctatgttg | 1080 |
| tcaggtagtc | ggatatcagg | ggtacaggat | gaacggaggt | ctatggcaac | agtgggtgct | 1140 |
| aaaggtgaaa | cgagtaaaat | ggaagccctc | aaggcatatc | ggaaggctaa | gggactgtgt | 1200 |
| tttaagtgtg | gagaaagatg | gggtcaactt | cacacgtgct | ctaacacagt | gccttacat | 1260 |
| ctggttgaag | aaatgtgggc | tctaacaatg | ggtgcatctg | agccggagat | ggactctgaa | 1320 |
| gagcctgcaa | ctgagactag | cctcgagagt | gtgcttgcta | tttctgttgc | agcagtatct | 1380 |
| ggcagcgaag | ggagcaaaac | tatcagactg | tgggcatcca | tttattgcca | acaggttttg | 1440 |
| gtgttagtgg | attctggtag | ctccgcgagt | tttatggata | accatctcac | aggagtaatg | 1500 |
| tccacaatga | agccattacc | aatgcctttg | caagtgaagg | ttgtcgatgg | aaggacacta | 1560 |
| tggagtactc | actttgttcc | tgattgccag | tggctatgtg | ggggacatac | tttcatccat | 1620 |
| gacttcaaaa | tattaccatt | gagtgggtat | gatctgattc | ttagtatgga | ctggctggaa | 1680 |
| aaatatagcc | aatgtctat | acactggggg | gaaaagtggt | tccaatttat | atataaaggg | 1740 |
| aagtcagtat | ggctgcaagg | tgttttaccc | aatactcggt | cttgttttc | cctaaattgt | 1800 |
| ctccagtttg | attcccttgt | caaacaagat | gcaattgagc | agttactgga | gttgcaagtc | 1860 |
| gtaccactta | gtgaacccac | tgacatgcct | atggtggtgg | ctgatttggt | taaccagttt | 1920 |
| aaccatctgt | tcgatgagcc | aaaagagtta | ccgcccaaga | ggtggattga | tcatgctata | 1980 |
| ccactaatcc | caggagctca | accttttcga | ctctga | | | 2016 |

<210> SEQ ID NO 2
<211> LENGTH: 671
<212> TYPE: PRT
<213> ORGANISM: Zea mays

```
<400> SEQUENCE: 2

Met Ala Pro Pro Arg Val Glu Asp Pro Met Ala Leu Leu Ala Lys
  1               5                  10                  15

Ile Asp Glu Gly Ser Lys Glu Thr Cys Arg Arg Met Glu Ala Ile His
             20                  25                  30

Ser Thr Met Glu Lys Met Glu Ile Thr Val Gln Gly Leu Val Ser Asn
         35                  40                  45

Gln Ser Asp Phe Lys Lys Trp Gln Pro Glu Ile Glu Arg Lys Val Val
     50                  55                  60

Glu Met Ala Glu Thr Leu Val Lys Ile Gln Thr Lys Ile Ser Asn Thr
 65                  70                  75                  80

Thr Pro Ser Thr Thr Ser Ser Gly Ala Val Pro Ala Val Ala Asn Val
                 85                  90                  95

Ser Met Ser Glu Thr Ala Ser Val Val Gly Glu Lys Met Ala Gly
            100                 105                 110

Ser Thr Leu His Arg Thr Ala Asp Pro Phe Arg Arg Pro Ala Ala Glu
            115                 120                 125

Ser Lys Val Asn Gln Met Ser Leu Pro Leu Gly Gly Met Ala Thr Pro
        130                 135                 140

Asn Pro His Ala Pro Trp Leu Phe Gly Gln Thr Ser Val Ser Pro Phe
145                 150                 155                 160

Ala Ser Pro Thr Trp Ser Gln Gly Leu Gly Gly Asn Met Pro Pro Met
                165                 170                 175

Asn Phe Pro Val Phe Asp Ala Ser Asn Pro Lys Leu Trp Lys Asn Arg
            180                 185                 190

Cys Glu Thr Tyr Phe Glu Tyr Ala Val Leu Val Asp Met Trp Ile
        195                 200                 205

Arg Leu Ala Ile Met His Phe Glu Gly Pro Thr Leu Phe Trp Leu Gln
        210                 215                 220

Tyr Met Glu Gly Arg Thr Arg Glu Met Asn Trp Gly Glu Leu Cys Ala
225                 230                 235                 240

Ala Leu Leu Thr Arg Phe Gly Arg Asp Gln His Asn Leu Leu Thr Arg
                245                 250                 255

Gln Phe Tyr His Ile Phe Gln Thr Gly Ser Val Ser Asp Tyr Ile Glu
            260                 265                 270

Gln Phe Asp Leu Leu His Gln Leu Leu Ala His Glu Asn His Leu
        275                 280                 285

Thr Thr Thr Met Val Thr Ala Arg Phe Val Asp Gly Leu Lys Asp Glu
        290                 295                 300

Leu Arg Ala Ala Val Ile Ile Gln Arg Pro Ala Asp Leu Asp Thr Thr
305                 310                 315                 320

Cys Ser Leu Thr Leu Leu Gln Glu Glu Val Met Ser Thr Ser Gly Arg
                325                 330                 335

Arg Glu Leu Arg Lys Val Asp Thr Asn Ser Ile Val Arg Val Pro Asn
            340                 345                 350

Lys Pro Asn Ala Leu Pro Met Leu Ser Gly Ser Arg Ile Ser Gly Val
        355                 360                 365

Gln Asp Glu Arg Arg Ser Met Ala Thr Val Gly Ala Lys Gly Glu Thr
    370                 375                 380

Ser Lys Met Glu Ala Leu Lys Ala Tyr Arg Lys Ala Lys Gly Leu Cys
385                 390                 395                 400

Phe Lys Cys Gly Glu Arg Trp Gly Gln Leu His Thr Cys Ser Asn Thr
                405                 410                 415
```

```
Val Pro Leu His Leu Val Glu Glu Met Trp Ala Leu Thr Met Gly Ala
            420                 425                 430

Ser Glu Pro Glu Met Asp Ser Glu Pro Ala Thr Glu Thr Ser Leu
        435                 440                 445

Glu Ser Val Leu Ala Ile Ser Val Ala Ala Val Ser Gly Ser Glu Gly
450                 455                 460

Ser Lys Thr Ile Arg Leu Trp Ala Ser Ile Tyr Cys Gln Gln Val Leu
465                 470                 475                 480

Val Leu Val Asp Ser Ser Ser Ala Ser Phe Met Asp Asn His Leu
                485                 490                 495

Thr Gly Val Met Ser Thr Met Lys Pro Leu Pro Met Pro Leu Gln Val
            500                 505                 510

Lys Val Val Asp Gly Arg Thr Leu Trp Ser Thr His Phe Val Pro Asp
            515                 520                 525

Cys Gln Trp Leu Cys Gly Gly His Thr Phe Ile His Asp Phe Lys Ile
            530                 535                 540

Leu Pro Leu Ser Gly Tyr Asp Leu Ile Leu Ser Met Asp Trp Leu Glu
545                 550                 555                 560

Lys Tyr Ser Pro Met Ser Ile His Trp Gly Glu Lys Trp Phe Gln Phe
                565                 570                 575

Ile Tyr Lys Gly Lys Ser Val Trp Leu Gln Gly Val Leu Pro Asn Thr
            580                 585                 590

Arg Ser Cys Phe Ser Leu Asn Cys Leu Gln Phe Asp Ser Leu Val Lys
            595                 600                 605

Gln Asp Ala Ile Glu Gln Leu Glu Leu Gln Val Val Pro Leu Ser
        610                 615                 620

Glu Pro Thr Asp Met Pro Met Val Val Ala Asp Leu Val Asn Gln Phe
625                 630                 635                 640

Asn His Leu Phe Asp Glu Pro Lys Glu Leu Pro Pro Lys Arg Trp Ile
                645                 650                 655

Asp His Ala Ile Pro Leu Ile Pro Gly Ala Gln Pro Phe Arg Leu
            660                 665                 670

<210> SEQ ID NO 3
<211> LENGTH: 2568
<212> TYPE: DNA
<213> ORGANISM: Zea mays

<400> SEQUENCE: 3
atggataaaa ataggggaccc tcaaaacaga agtggggaac agagtgaaga gggtaatggc      60
agaggcaagt gggggggctga ccagagagtt tccggggacc gtagcgtagt ccttggttgc    120
agctctgtta acaactctaa tggtggaccg gacctcgaag ggacaggaga tgaagctgtt    180
ggagatgaag gaagccggaa agctgtccag aaactaagga gagcctacac tggatcctca    240
tcacgagtac aacacgagat tgcaggccag agcgggagcg atggcgcccc gagagtggaa    300
gaccccatgg cactgttgtt agccaaaatc gatgaaggca ataaggaaac ctgccgacgc    360
atggaggcaa tccagtctac aatggagaag atggagatca cagtgcaagg actggtctcc    420
gatcggagcg acttcaagaa gtggcggccc gagatcgaga ggaaggtggt ggagatggcg    480
gaaaccctag tgaagatcca aacaaagata gtaatacga ccccgtctac cacttcttca    540
ggagcagtac cagcggtcac caacgtctcg atgtcggcaa caacttcggt ggtggcgggg    600
gagaagatgg cgggttctac cctgcaccgt acgacggatc ccttccgacg acctgctacc    660
```

```
gaatcgaagg tgaaccggat gtcgctgccc ttgggaggta tggccacgcc taatcctcat    720
gctccttggt tattcggcca aacctctgtg agtccctttg catctccaac ctggtcacaa    780
ggattgggag gaaacatgcc accgatgaat tttccagtgt tgatgcatc caatcctaag     840
ctgtggaaaa atcggtgtga aacttatttt gagtactatg ctgtcctagt ggagatgtgg    900
attcgattgg ctatcatgca cttttgagggg ccgactctat tttggctgca gtctatggaa   960
ggtagaacga gggaaatgaa ttggggtgaa ctttgtgcag ctctgctcac cagattcagt   1020
cgtgaccagc ataatttgct cactagacaa ttttaccata tattccagac aggatcagta   1080
tcagattata ttgaacaatt tgatttgtta ttgcatcagt tgttggctca tgaaaatcat   1140
ctcaccacta ccatggttac tgcccgtttt gttgatggac tgaaagacga actaagggca   1200
acgataatca tacagcggcc agctgatttg gatacaacat gttctctagc attattacaa   1260
gaagaggtca tgagtacttc cggacgtaga gaactgagaa aagtggatac taactccatt   1320
gtcagagttc caaacaaacc caatgccttg cctatgttgt caggtagtcg gatatcaggg   1380
gtacaggatg aacggaggtc tatggcaaca gtgggtgata aggtgaaaac gagtaaaatg   1440
gaagccctca aggcatatcg gaaggctaag ggactgtgtt ttaagtgtgg agaaagatgg   1500
ggtcaacttc acacgtgctc taacacagtg cctttacatc tggttgaaga aatgtgggct   1560
ctaacaatgg gtgcatctga gccggagatg gactctgaag agcctgcaac tgagactagc   1620
cttgagagtg tgcttgctat ttctgttgca gcagtatccg acagcgaagg gagcaaaact   1680
atcagactgt gggcatccat ttattgccaa caggttttgg tgttagtgga ttctagtagc   1740
tccgcgagtt ttatggataa ccatcttaca ggagtaatgt ccacagtgaa gccattacca   1800
atgcctttgc aagtgaaggt tgtcgatgga aggacactat ggagtactca ctttgttcct   1860
gattgccagt ggctatgtgg gggacatact ttcatccatg acttcaaaat attaccattg   1920
agtgggtatg atctgattct tgtgttgtat ggccactcac ctatacattt tgggcttgtt   1980
gacaatggtc agtgtacagt acctaatctt caagagctgt tggtagagag acagctgatg   2040
ctccagcaag ttaagttgca tctcaatcgt gcccagcaac gtatgaaaaa acaatcggat   2100
aaagggagga cagatcatgt ttttgaagaa ggacagcaag tgtttctcaa acttcaacct   2160
tattgtcaat cttccgtagc ttcacgtcct tatcccaaat tggcttttaa gttctttggt   2220
ccatttacca ttgctcgcaa ggttaatgtt gtagcttatg agttggctct tccaccaggt   2280
tttggtattc atccggtatt ccatgttttct cagttgaagc ctcaagttgg ttccaataca   2340
cctgttagct cattagtacc tgatatgtcg actggtttgc aagtgcctga acaaatatta   2400
gactccaagt tggtttggcg tggaggcaaa gcactttccc atgtgttggt taaatggttg   2460
gattgggatg tctatctagc tacgtgggaa gatgaagcag tgctgaagca acaattccct   2520
gcagcaccag cttggggacc agctgtatct ccaggggaa tatgttaa              2568
```

<210> SEQ ID NO 4
<211> LENGTH: 855
<212> TYPE: PRT
<213> ORGANISM: Zea mays

<400> SEQUENCE: 4

Met Asp Lys Asn Arg Asp Pro Gln Asn Arg Ser Gly Glu Gln Ser Glu
1               5                   10                  15

Glu Gly Asn Gly Arg Gly Lys Trp Gly Ala Asp Gln Arg Val Ser Gly
            20                  25                  30

Asp Arg Ser Val Val Leu Gly Cys Ser Ser Val Asn Asn Ser Asn Gly

```
            35                  40                  45
Gly Pro Asp Leu Glu Gly Thr Gly Asp Glu Ala Val Gly Asp Glu Gly
 50                  55                  60

Lys Pro Glu Ala Val Gln Lys Leu Arg Arg Ala Tyr Thr Gly Ser Ser
 65                  70                  75                  80

Ser Arg Val Gln His Glu Ile Ala Gly Gln Ser Gly Ser Asp Gly Ala
                 85                  90                  95

Pro Arg Val Glu Asp Pro Met Ala Leu Leu Ala Lys Ile Asp Glu
                100                 105                 110

Gly Asn Lys Glu Thr Cys Arg Arg Met Glu Ala Ile Gln Ser Thr Met
                115                 120                 125

Glu Lys Met Glu Ile Thr Val Gln Gly Leu Val Ser Asp Arg Ser Asp
                130                 135                 140

Phe Lys Lys Trp Arg Pro Glu Ile Glu Arg Lys Val Val Glu Met Ala
145                 150                 155                 160

Glu Thr Leu Val Lys Ile Gln Thr Lys Ile Ser Asn Thr Thr Pro Ser
                165                 170                 175

Thr Thr Ser Ser Gly Ala Val Pro Ala Val Thr Asn Val Ser Met Ser
                180                 185                 190

Ala Thr Ser Val Val Ala Gly Glu Lys Met Ala Gly Ser Thr Leu
                195                 200                 205

His Arg Thr Thr Asp Pro Phe Arg Arg Pro Ala Thr Glu Ser Lys Val
                210                 215                 220

Asn Arg Met Ser Leu Pro Leu Gly Gly Met Ala Thr Pro Asn Pro His
225                 230                 235                 240

Ala Pro Trp Leu Phe Gly Gln Thr Ser Val Ser Pro Phe Ala Ser Pro
                245                 250                 255

Thr Trp Ser Gln Gly Leu Gly Gly Asn Met Pro Pro Met Asn Phe Pro
                260                 265                 270

Val Phe Asp Ala Ser Asn Pro Lys Leu Trp Lys Asn Arg Cys Glu Thr
                275                 280                 285

Tyr Phe Glu Tyr Tyr Ala Val Leu Val Glu Met Trp Ile Arg Leu Ala
                290                 295                 300

Ile Met His Phe Glu Gly Pro Thr Leu Phe Trp Leu Gln Ser Met Glu
305                 310                 315                 320

Gly Arg Thr Arg Glu Met Asn Trp Gly Glu Leu Cys Ala Ala Leu Leu
                325                 330                 335

Thr Arg Phe Ser Arg Asp Gln His Asn Leu Leu Thr Arg Gln Phe Tyr
                340                 345                 350

His Ile Phe Gln Thr Gly Ser Val Ser Asp Tyr Ile Glu Gln Phe Asp
                355                 360                 365

Leu Leu Leu His Gln Leu Leu Ala His Glu Asn His Leu Thr Thr Thr
                370                 375                 380

Met Val Thr Ala Arg Phe Val Asp Gly Leu Lys Asp Glu Leu Arg Ala
385                 390                 395                 400

Thr Ile Ile Ile Gln Arg Pro Ala Asp Leu Asp Thr Cys Ser Leu
                405                 410                 415

Ala Leu Leu Gln Glu Glu Val Met Ser Thr Ser Gly Arg Arg Glu Leu
                420                 425                 430

Arg Lys Val Asp Thr Asn Ser Ile Val Arg Val Pro Asn Lys Pro Asn
                435                 440                 445

Ala Leu Pro Met Leu Ser Gly Ser Arg Ile Ser Gly Val Gln Asp Glu
                450                 455                 460
```

```
Arg Arg Ser Met Ala Thr Val Gly Asp Lys Gly Glu Thr Ser Lys Met
465                 470                 475                 480

Glu Ala Leu Lys Ala Tyr Arg Lys Ala Lys Gly Leu Cys Phe Lys Cys
                485                 490                 495

Gly Glu Arg Trp Gly Gln Leu His Thr Cys Ser Asn Thr Val Pro Leu
            500                 505                 510

His Leu Val Glu Glu Met Trp Ala Leu Thr Met Gly Ala Ser Glu Pro
        515                 520                 525

Glu Met Asp Ser Glu Glu Pro Ala Thr Glu Thr Ser Leu Glu Ser Val
    530                 535                 540

Leu Ala Ile Ser Val Ala Ala Val Ser Asp Ser Glu Gly Ser Lys Thr
545                 550                 555                 560

Ile Arg Leu Trp Ala Ser Ile Tyr Cys Gln Gln Val Leu Val Leu Val
                565                 570                 575

Asp Ser Ser Ser Ala Ser Phe Met Asp Asn His Leu Thr Gly Val
            580                 585                 590

Met Ser Thr Val Lys Pro Leu Pro Met Pro Leu Gln Val Lys Val Val
        595                 600                 605

Asp Gly Arg Thr Leu Trp Ser Thr His Phe Val Pro Asp Cys Gln Trp
610                 615                 620

Leu Cys Gly Gly His Thr Phe Ile His Asp Phe Lys Ile Leu Pro Leu
625                 630                 635                 640

Ser Gly Tyr Asp Leu Ile Leu Val Leu Tyr Gly His Ser Pro Ile His
            645                 650                 655

Phe Gly Leu Val Asp Asn Gly Gln Cys Thr Val Pro Asn Leu Gln Glu
        660                 665                 670

Leu Leu Val Glu Arg Gln Leu Met Leu Gln Gln Val Lys Leu His Leu
    675                 680                 685

Asn Arg Ala Gln Gln Arg Met Lys Lys Gln Ser Asp Lys Gly Arg Thr
690                 695                 700

Asp His Val Phe Glu Glu Gly Gln Gln Val Phe Leu Lys Leu Gln Pro
705                 710                 715                 720

Tyr Cys Gln Ser Ser Val Ala Ser Arg Pro Tyr Pro Lys Leu Ala Phe
                725                 730                 735

Lys Phe Phe Gly Pro Phe Thr Ile Ala Arg Lys Val Asn Val Val Ala
            740                 745                 750

Tyr Glu Leu Ala Leu Pro Pro Gly Phe Gly Ile His Pro Val Phe His
        755                 760                 765

Val Ser Gln Leu Lys Pro Gln Val Gly Ser Asn Thr Pro Val Ser Ser
    770                 775                 780

Leu Val Pro Asp Met Ser Thr Gly Leu Gln Val Pro Glu Gln Ile Leu
785                 790                 795                 800

Asp Ser Lys Leu Val Trp Arg Gly Gly Lys Ala Leu Ser His Val Leu
                805                 810                 815

Val Lys Trp Leu Asp Trp Asp Val Tyr Leu Ala Thr Trp Glu Asp Glu
            820                 825                 830

Ala Val Leu Lys Gln Gln Phe Pro Ala Ala Pro Ala Trp Gly Pro Ala
        835                 840                 845

Val Ser Pro Gly Gly Ile Cys
    850                 855

<210> SEQ ID NO 5
<211> LENGTH: 705
```

<212> TYPE: DNA
<213> ORGANISM: Zea mays

<400> SEQUENCE: 5

```
atggtgtgcc atctgagatc tgcgagcgtg ccttcgagcc ctcgctctaa tgagatccat     60
gttgaggaac agctgcagag cctgaaggca gccatctcat caccgtcagt gaccatcaaa    120
accatggtcg atggtctgag caagctcggg agcatctacg accgcattga tgtgctcaca    180
tgcttgccca ccagccagag gaaggcggtg gaggaagagc tcgagcgctc cctcgtcctg    240
cttgacctct gcagcgcctt gcaagagagc ttcgtggagc tcaaggccag tgttcaagag    300
atgcagttgg ctctcaaaag aggagacgac gcggctctcc agaccagggt tcagtgctac    360
gcgcgcttgg tcaagaaggc acagaagctg ttcaagaagt caacaagaa gactgcttct     420
gacatcgaaa gttgcagggt gatcaacctt gttgctgaag cgagggagat tgctgtgtca    480
accctagaat caacattgca ctcctgtca aagcaaattg caatgccaag ttgtagcaag     540
tggtcacttg tctctaagtc tttccaaaag aagagagtca tgtgcgaggc ggatcaattg    600
caagggctgg agctcggctt cgttgatctt gagaacagag ttgggacatt gttcaggaaa    660
ttggtccaga acagagtgtc ttttctgaat attcttagct tgtag                    705
```

<210> SEQ ID NO 6
<211> LENGTH: 234
<212> TYPE: PRT
<213> ORGANISM: Zea mays

<400> SEQUENCE: 6

```
Met Val Cys His Leu Arg Ser Ala Ser Val Pro Ser Ser Pro Arg Ser
1               5                   10                  15

Asn Glu Ile His Val Glu Glu Gln Leu Gln Ser Leu Lys Ala Ala Ile
            20                  25                  30

Ser Ser Pro Ser Val Thr Ile Lys Thr Met Val Asp Gly Leu Ser Lys
        35                  40                  45

Leu Gly Ser Ile Tyr Asp Arg Ile Asp Val Leu Thr Cys Leu Pro Thr
    50                  55                  60

Ser Gln Arg Lys Ala Val Glu Glu Leu Glu Arg Ser Leu Val Leu
65                  70                  75                  80

Leu Asp Leu Cys Ser Ala Leu Gln Glu Ser Phe Val Glu Leu Lys Ala
                85                  90                  95

Ser Val Gln Glu Met Gln Leu Ala Leu Lys Arg Gly Asp Asp Ala Ala
            100                 105                 110

Leu Gln Thr Arg Val Gln Cys Tyr Ala Arg Leu Val Lys Lys Ala Gln
        115                 120                 125

Lys Leu Phe Lys Phe Asn Lys Lys Thr Ala Ser Asp Ile Glu Ser
    130                 135                 140

Cys Arg Val Ile Asn Leu Val Ala Glu Ala Arg Glu Ile Ala Val Ser
145                 150                 155                 160

Thr Leu Glu Ser Thr Leu His Leu Leu Ser Lys Gln Ile Ala Met Pro
                165                 170                 175

Ser Cys Ser Lys Trp Ser Leu Val Ser Lys Ser Phe Gln Lys Lys Arg
            180                 185                 190

Val Met Cys Glu Ala Asp Gln Leu Gln Gly Leu Glu Leu Gly Phe Val
        195                 200                 205

Asp Leu Glu Asn Arg Val Gly Thr Leu Phe Arg Lys Leu Val Gln Asn
    210                 215                 220
```

Arg Val Ser Phe Leu Asn Ile Leu Ser Leu
225                 230

<210> SEQ ID NO 7
<211> LENGTH: 705
<212> TYPE: DNA
<213> ORGANISM: Zea mays

<400> SEQUENCE: 7

```
atggtgtgcc atctgagatc tgcgagcgtg ccttcgagcc ctcgctctaa tgagatccat      60
gttgaggaac agctgcagag cctgaaggca gccatctcat caccgtcagt gaccatcaaa     120
accatggtcg atggtctgag caagctcggg agcatctacg accgcattga tgtgctcaca     180
tgcttgccca ccagccagag gaaggcggtg gaggaagagc tcgagcgctc cctcgtcctg     240
cttgacctct gcagcgcctt gcaagagagc ttcgtggagc tcaaggccag tgttcaagag     300
atgcagttgg ctctcaaaag aggagacgac gcggctctcc agaccagggt tcagtgctac     360
gcgcgcttgg tcaagaaggc acagaagctg ttcaagaagt tcaacaagaa gactgcttct     420
gacatcgaaa gttgcagggt gatcaacctt gttgctgaag cgagggagat tgccgtgtca     480
accctagaat caacattgca ctcctgtca aagcaaattg caatgccaag ttgtagcaag     540
tggtcacttg tctctaagtc tttccaaaag aagagagtca tgtgcgaggc ggatcaattg     600
caagggctgg agctcggctt cattgatctt gagaacagag ttgggacatt gttcaggaaa     660
ttggtccaga acagagtgtc ttttctgaat attcttagct tgtag               705
```

<210> SEQ ID NO 8
<211> LENGTH: 234
<212> TYPE: PRT
<213> ORGANISM: Zea mays

<400> SEQUENCE: 8

Met Val Cys His Leu Arg Ser Ala Ser Val Pro Ser Ser Pro Arg Ser
1               5                   10                  15

Asn Glu Ile His Val Glu Glu Gln Leu Gln Ser Leu Lys Ala Ala Ile
                20                  25                  30

Ser Ser Pro Ser Val Thr Ile Lys Thr Met Val Asp Gly Leu Ser Lys
            35                  40                  45

Leu Gly Ser Ile Tyr Asp Arg Ile Asp Val Leu Thr Cys Leu Pro Thr
        50                  55                  60

Ser Gln Arg Lys Ala Val Glu Glu Leu Glu Arg Ser Leu Val Leu
65                  70                  75                  80

Leu Asp Leu Cys Ser Ala Leu Gln Glu Ser Phe Val Glu Leu Lys Ala
                85                  90                  95

Ser Val Gln Glu Met Gln Leu Ala Leu Lys Arg Gly Asp Asp Ala Ala
            100                 105                 110

Leu Gln Thr Arg Val Gln Cys Tyr Ala Arg Leu Val Lys Lys Ala Gln
        115                 120                 125

Lys Leu Phe Lys Lys Phe Asn Lys Lys Thr Ala Ser Asp Ile Glu Ser
    130                 135                 140

Cys Arg Val Ile Asn Leu Val Ala Glu Ala Arg Glu Ile Ala Val Ser
145                 150                 155                 160

Thr Leu Glu Ser Thr Leu His Leu Leu Ser Lys Gln Ile Ala Met Pro
                165                 170                 175

Ser Cys Ser Lys Trp Ser Leu Val Ser Lys Ser Phe Gln Lys Lys Arg
            180                 185                 190

Val Met Cys Glu Ala Asp Gln Leu Gln Gly Leu Glu Leu Gly Phe Ile
            195                 200                 205

Asp Leu Glu Asn Arg Val Gly Thr Leu Phe Arg Lys Leu Val Gln Asn
    210                 215                 220

Arg Val Ser Phe Leu Asn Ile Leu Ser Leu
225                 230

<210> SEQ ID NO 9
<211> LENGTH: 678
<212> TYPE: DNA
<213> ORGANISM: Zea mays

<400> SEQUENCE: 9

```
atgccttcga gccctcattc cagggagacc aatgttgagg aacagattct atgcctgaaa    60
gcagccatct ctctgccttc agtgactgtc gaaaccgtat tcgatgatct gagcaagctc   120
gggagcatct acaaccacat cgacgcactc acatgcttgc ccaggagcca gaggaaggca   180
gtggaggagg aggttgagca ctccctcgtc ctgctcgacc tctgcagcat tgtgcaagag   240
agctttgttg aactcaaggc ctgtgtccag agatacagtt ggctctctga acgaggtgat   300
cacacagctg cccataccaa gattcagtgc tatgtgcgct cggccaagaa ggcacagaag   360
ctgttcaaga aggtcaacaa gaagactgtc tctgacatcg aaggatgctg ggtgatcaat   420
ctggttgctg gagcgaggga gattgctgcg ttgatccttg aatcgacatt gcatctcctg   480
tcaaagcaaa ttgtggtcac aagttctagc aagtggtcac ttgtttccaa gtcattccga   540
aagaagtgtg tcatatgtga ggcagaacaa ttgcaagggt tggagctgga cattgttgaa   600
cttgagagca gagtagggac attgttcagg aagttgatcc aaagcagagt gtctcttctt   660
aatgctctta gcttgtag                                                 678
```

<210> SEQ ID NO 10
<211> LENGTH: 225
<212> TYPE: PRT
<213> ORGANISM: Zea mays

<400> SEQUENCE: 10

Met Pro Ser Ser Pro His Ser Arg Glu Thr Asn Val Glu Glu Gln Ile
1               5                   10                  15

Leu Cys Leu Lys Ala Ala Ile Ser Leu Pro Ser Val Thr Val Glu Thr
            20                  25                  30

Val Phe Asp Asp Leu Ser Lys Leu Gly Ser Ile Tyr Asn His Ile Asp
        35                  40                  45

Ala Leu Thr Cys Leu Pro Arg Ser Gln Arg Lys Ala Val Glu Glu Glu
    50                  55                  60

Val Glu His Ser Leu Val Leu Leu Asp Leu Cys Ser Ile Val Gln Glu
65                  70                  75                  80

Ser Phe Val Glu Leu Lys Ala Cys Val Gln Glu Ile Gln Leu Ala Leu
                85                  90                  95

Lys Arg Gly Asp His Thr Ala Ala His Thr Lys Ile Gln Cys Tyr Val
            100                 105                 110

Arg Ser Ala Lys Lys Ala Gln Lys Leu Phe Lys Val Asn Lys Lys
        115                 120                 125

Thr Val Ser Asp Ile Glu Gly Cys Trp Val Ile Asn Leu Val Ala Gly
    130                 135                 140

Ala Arg Glu Ile Ala Ala Leu Ile Leu Glu Ser Thr Leu His Leu Leu
145                 150                 155                 160

Ser Lys Gln Ile Val Val Thr Ser Ser Lys Trp Ser Leu Val Ser
            165                 170                 175

Lys Ser Phe Arg Lys Lys Cys Val Ile Cys Glu Ala Glu Gln Leu Gln
            180                 185                 190

Gly Leu Glu Leu Asp Ile Val Glu Leu Glu Ser Arg Val Gly Thr Leu
            195                 200                 205

Phe Arg Lys Leu Ile Gln Ser Arg Val Ser Leu Leu Asn Ala Leu Ser
    210                 215                 220

Leu
225

<210> SEQ ID NO 11
<211> LENGTH: 678
<212> TYPE: DNA
<213> ORGANISM: Zea mays

<400> SEQUENCE: 11
atgccttcga gccctcattc cagggagacc aatgttgagg aacagattct atgcctgaaa    60
gcagccatct ctctgccttc agtgactgtc gaaaccgtat tcgatgatct gagcaagctc   120
ggagcatct acaaccacat cgacgcactc acatgcttgc ccaggagcca gaggaaggca   180
gtggaggagg aggttgagca ctccctcgtc ctgctcgacc tctgcagcat tgtgcaagag   240
agctttgttg aactcaaggc ctgtgtccag gagatacagt tggctctgaa acgaggtgat   300
cacacagctg cccataccaa gattcagtgc tatgtgcgct cggccaagaa ggcacagaag   360
ctgttcaaga aggtcaacaa gaagactgtc tctgacatcg aaggatgctg ggtgatcaat   420
ctggttgctg agcgaggga gattgctgcg ttgatccttg aatcgacatt gcatctcctg   480
tcaaagcaaa ttgtggtcac aagttctagc aagtggtcac ttgtttccaa gtcattccga   540
aagaagtgtg tcatatgtga ggcagaacaa ttgcaagggt tggagctgga cattgttgaa   600
cttgagagca gagtagggac attgttcagg aagttgatcc aaagcagagt gtctcttctt   660
aatgctctta gcttgtag                                                 678

<210> SEQ ID NO 12
<211> LENGTH: 225
<212> TYPE: PRT
<213> ORGANISM: Zea mays

<400> SEQUENCE: 12

Met Pro Ser Ser Pro His Ser Arg Glu Thr Asn Val Glu Glu Gln Ile
1               5                   10                  15

Leu Cys Leu Lys Ala Ala Ile Ser Leu Pro Ser Val Thr Val Glu Thr
            20                  25                  30

Val Phe Asp Asp Leu Ser Lys Leu Gly Ser Ile Tyr Asn His Ile Asp
        35                  40                  45

Ala Leu Thr Cys Leu Pro Arg Ser Gln Arg Lys Ala Val Glu Glu Glu
    50                  55                  60

Val Glu His Ser Leu Val Leu Leu Asp Leu Cys Ser Ile Val Gln Glu
65                  70                  75                  80

Ser Phe Val Glu Leu Lys Ala Cys Val Gln Glu Ile Gln Leu Ala Leu
                85                  90                  95

Lys Arg Gly Asp His Thr Ala Ala His Thr Lys Ile Gln Cys Tyr Val
            100                 105                 110

Arg Ser Ala Lys Lys Ala Gln Lys Leu Phe Lys Lys Val Asn Lys Lys
        115                 120                 125

```
Thr Val Ser Asp Ile Glu Gly Cys Trp Val Ile Asn Leu Val Ala Gly
    130                 135                 140

Ala Arg Glu Ile Ala Ala Leu Ile Leu Glu Ser Thr Leu His Leu Leu
145                 150                 155                 160

Ser Lys Gln Ile Val Val Thr Ser Ser Ser Lys Trp Ser Leu Val Ser
                165                 170                 175

Lys Ser Phe Arg Lys Lys Cys Val Ile Cys Glu Ala Glu Gln Leu Gln
                180                 185                 190

Gly Leu Glu Leu Asp Ile Val Glu Leu Glu Ser Arg Val Gly Thr Leu
                195                 200                 205

Phe Arg Lys Leu Ile Gln Ser Arg Val Ser Leu Leu Asn Ala Leu Ser
210                 215                 220

Leu
225

<210> SEQ ID NO 13
<211> LENGTH: 681
<212> TYPE: DNA
<213> ORGANISM: Zea mays

<400> SEQUENCE: 13
atgccttcga gctctcgctc cagtgagacc tctattgacg aacagattct gagcctgaaa       60
gcagccatct ctctgccttc agtgtccatc aaaaccatgg tggatagtct gagcaagctc      120
ggcagcatct acaaccacat cgacgcactc acatgcttgc ccaggagcca gaggaaggca      180
gtggaggagg agctcgagca ctccctggtc ctgctcgatc tctgcagcgc tgtgcaagag      240
agctttgttg agcttaaggc cagtgtccag gaggtgcagt tggctctgga acgaggtgac      300
cacacggctg cccataccaa gattcagtgc tatgtgcgct cggccaagaa ggcacagaag      360
ctgttcaaga aggtcaacaa gaagactgcc tctgacatcg aaggatgctg ggtgattaat      420
ctggttgctg aagcgagaga gattgccgtg ttgatccttg aatcgacatt gcatctcatg      480
ttgaagcaaa ttgtgattcc aagctctagc aagtggtccc ttgtttccaa gtcattccga      540
aagaagtgtg ttgtatcatg cgatgcggaa caattgcaag ggttggagct ggacgttgtt      600
gatcttgaga gcagagttgg acattgttca aggacgttga tccagagcag agtgtctctt      660
cttaatgctc ttagcttgta g                                                681

<210> SEQ ID NO 14
<211> LENGTH: 226
<212> TYPE: PRT
<213> ORGANISM: Zea mays

<400> SEQUENCE: 14

Met Pro Ser Ser Ser Arg Ser Ser Glu Thr Ser Ile Asp Glu Gln Ile
1               5                   10                  15

Leu Ser Leu Lys Ala Ala Ile Ser Leu Pro Ser Val Ser Ile Lys Thr
                20                  25                  30

Met Val Asp Ser Leu Ser Lys Leu Gly Ser Ile Tyr Asn His Ile Asp
            35                  40                  45

Ala Leu Thr Cys Leu Pro Arg Ser Gln Arg Lys Ala Val Glu Glu Glu
        50                  55                  60

Leu Glu His Ser Leu Val Leu Leu Asp Leu Cys Ser Ala Val Gln Glu
65                  70                  75                  80

Ser Phe Val Glu Leu Lys Ala Ser Val Gln Glu Val Gln Leu Ala Leu
                85                  90                  95
```

```
Glu Arg Gly Asp His Thr Ala Ala His Thr Lys Ile Gln Cys Tyr Val
            100                 105                 110

Arg Ser Ala Lys Lys Ala Gln Lys Leu Phe Lys Val Asn Lys Lys
        115                 120                 125

Thr Ala Ser Asp Ile Glu Gly Cys Trp Val Ile Asn Leu Val Ala Glu
    130                 135                 140

Ala Arg Glu Ile Ala Val Leu Ile Leu Glu Ser Thr Leu His Leu Met
145                 150                 155                 160

Leu Lys Gln Ile Val Ile Pro Ser Ser Lys Trp Ser Leu Val Ser
                165                 170                 175

Lys Ser Phe Arg Lys Lys Cys Val Val Ser Cys Asp Ala Glu Gln Leu
        180                 185                 190

Gln Gly Leu Glu Leu Asp Val Val Asp Leu Glu Ser Arg Val Gly Thr
            195                 200                 205

Leu Phe Arg Thr Leu Ile Gln Ser Arg Val Ser Leu Leu Asn Ala Leu
    210                 215                 220

Ser Leu
225
```

<210> SEQ ID NO 15
<211> LENGTH: 681
<212> TYPE: DNA
<213> ORGANISM: Zea mays

<400> SEQUENCE: 15

```
atgccttcga gctctcgctc cagtgagacc tctattgacg aacagattct gagcctgaaa      60
gcagccatct ctctgccttc agtgtccatc aaaaccatgg tggatagtct gagcaagctc     120
ggcagcatct acaaccacat cgacgcactc acatgcttgc ccaggagcca gaggaaggca     180
gtggaggagg agctcgagca ctccctggtc ctgctcgatc tctgcagcgc tgtgcaagag     240
agctttgttg agcttaaggc cagtgtccag gaggtgcagt tggctctgga acgaggtgac     300
cacacggctg cccataccaa gattcagtgc tatgtgcgct cggccaagaa ggcacagaag     360
ctgttcaaga aggtcaacaa gaagactgcc tctgacatcg aaggatgctg ggtgattaat     420
ctggttgctg aagcgagaga gattgccgtg ttgatccttg aatcgacatt gcatctcatg     480
ttgaagcaaa ttgtgattcc aagctctagc aagtggtccc ttgtttccaa gtcattccga     540
aagaagtgtg ttgtatcatg cgatgcggaa caattgcaag ggttggagct ggacgttgtt     600
gatcttgaga gcagagttgg gacattgttc aggacgttga tccagagcag agtgtctctt     660
cttaatgctc ttagcttgta g                                               681
```

<210> SEQ ID NO 16
<211> LENGTH: 226
<212> TYPE: PRT
<213> ORGANISM: Zea mays

<400> SEQUENCE: 16

```
Met Pro Ser Ser Ser Arg Ser Ser Glu Thr Ser Ile Asp Glu Gln Ile
1               5                   10                  15

Leu Ser Leu Lys Ala Ala Ile Ser Leu Pro Ser Val Ser Ile Lys Thr
            20                  25                  30

Met Val Asp Ser Leu Ser Lys Leu Gly Ser Ile Tyr Asn His Ile Asp
        35                  40                  45

Ala Leu Thr Cys Leu Pro Arg Ser Gln Arg Lys Ala Val Glu Glu Glu
    50                  55                  60
```

```
Leu Glu His Ser Leu Val Leu Leu Asp Leu Cys Ser Ala Val Gln Glu
 65                  70                  75                  80

Ser Phe Val Glu Leu Lys Ala Ser Val Gln Glu Val Gln Leu Ala Leu
                 85                  90                  95

Glu Arg Gly Asp His Thr Ala Ala His Thr Lys Ile Gln Cys Tyr Val
            100                 105                 110

Arg Ser Ala Lys Lys Ala Gln Lys Leu Phe Lys Val Asn Lys Lys
        115                 120                 125

Thr Ala Ser Asp Ile Glu Gly Cys Trp Val Ile Asn Leu Val Ala Glu
    130                 135                 140

Ala Arg Glu Ile Ala Val Leu Ile Leu Glu Ser Thr Leu His Leu Met
145                 150                 155                 160

Leu Lys Gln Ile Val Ile Pro Ser Ser Lys Trp Ser Leu Val Ser
                165                 170                 175

Lys Ser Phe Arg Lys Lys Cys Val Val Ser Cys Asp Ala Glu Gln Leu
            180                 185                 190

Gln Gly Leu Glu Leu Asp Val Val Asp Leu Glu Ser Arg Val Gly Thr
        195                 200                 205

Leu Phe Arg Thr Leu Ile Gln Ser Arg Val Ser Leu Leu Asn Ala Leu
    210                 215                 220

Ser Leu
225

<210> SEQ ID NO 17
<211> LENGTH: 1836
<212> TYPE: DNA
<213> ORGANISM: Zea mays

<400> SEQUENCE: 17
atggagaata cgaggcgtgg gagacgaacg gaacgatcca acgcatcgtc ttcttcatcg      60
aaacaggctg ctgcagcagc atgcataggt gggcctggcc tgagagaaag taatgcgtcg     120
gtgggccaga gtggagacgt gctgtggcgt tgtgcagtcc agaacgaacc atacaagccg     180
cccgtcggtc ttgtggttct ttttgacaga acacacgcgt cgcttcctct ctaccaccga     240
gcgccaaaga cgaaacgtct ggctttaggg tcccaatcct acgcggactc aaccaaggtg     300
ccgccgacgc tacccatgga gaaccgcggg gactcccagc aaggagtgca gggagggcga     360
cctgtcgagc ctggcgcagg gagggctgca ccgaggcagg gattccagta caacggctca     420
ggtcaattcc gtccaggata cggtggcggt cgtggctacg cccagaaccg ggggaggacc     480
tggtcgcggg caggacacgg gcgcggaatg cacggcccgg ttggaggccg tggcgcggcg     540
agacccaacc cagctggccc tggcacgatg actccggcat cgggcatgga tggcacaacg     600
gggactggtc cggttgcagg tggaagtatt ggcacagctg gggatcaggc aggaatggca     660
gcggtgttgc tacagcaagc actctcagct ctccagggta tgaatgccga caagggaggg     720
ggtgctgctc aaccttctgc tgctcaacaa cctgtgatgc cggtacctag tgatgggaag     780
aaggtacacc cgaaacctgc tgttgtggaa gagaagaaaa agtccgatca agagaaggag     840
ggttttgtgg atgcgcctaa gaacaacaag agctactgcc ataggtgcta cggcaaggga     900
catgtcatga gtgagtgttc gacggcgctg ttttgtgaag tatgtggcac tgatacgcac     960
ataaagcaca aatgcccggt gttcaacgct ccgaaggttt atgcggttcc ggccggcttt    1020
ggcatcaaca agggcggctt cttccacatt ccctcgaaca agaagctggt gaagacgaag    1080
caagatgcta ggacagcaat gatacaggtg tcggagggac agatcagctt ggagaatgtt    1140
```

-continued

```
aaccgtgagc tggaccgctt gcttcccggg tctgctcctt ggaaggtgga acaagtttcg      1200
gctagttcct acagaactac ctttccatca gcctcggaac tgcagcgtat ggtggagtgg      1260
gggccggttc gtgctaaatc acagaaggca gtgctggaat tcatagctag cactagcatg      1320
gctgaaggac gggtcaaggc aaggctgacg gatgtgtggg tgcagtttga tggactgccg      1380
gctcagcttt gcacttacca acacatttgg ggagtgggtt cgaaacttgg ggtcacggtt      1440
gaagtggaca tgcctttttt ccgcaagcat gggatctgta aatgttggt ggctgtcatt       1500 gatccagagg caattccatt cgcaggtgat gtggaaatta acaagataat ttacgaggtg      1560
cactattggg tggaacaagg ccctctggat gatgaaccaa cacctatggt ctctgatctt      1620
ggcggtgatg accagggtaa cggtgacaac agcaagcaaa ataatgccaa ggaagggaat      1680
gagcaattca aaatgccggg tgaggaaggg agagatggag aggagaagaa aggcagtaat      1740
gatgtcgggg agcataagca agtgatggat gctgctccgg tggatgatgg tcaagccttg      1800
caatgtgatg aggagaatag gctggctgtt ttttga                                1836
```

<210> SEQ ID NO 18
<211> LENGTH: 611
<212> TYPE: PRT
<213> ORGANISM: Zea mays

<400> SEQUENCE: 18

```
Met Glu Asn Thr Arg Arg Gly Arg Arg Thr Glu Arg Ser Asn Ala Ser
1               5                   10                  15

Ser Ser Ser Ser Lys Gln Ala Ala Ala Ala Cys Ile Gly Gly Pro
            20                  25                  30

Gly Leu Arg Glu Ser Asn Ala Ser Val Gly Gln Ser Gly Asp Val Leu
        35                  40                  45

Trp Arg Cys Ala Val Gln Asn Glu Pro Tyr Lys Pro Val Gly Leu
    50                  55                  60

Val Val Leu Phe Asp Arg Thr His Ala Ser Leu Pro Leu Tyr His Arg
65                  70                  75                  80

Ala Pro Lys Thr Lys Arg Leu Ala Leu Gly Ser Gln Ser Tyr Ala Asp
                85                  90                  95

Ser Thr Lys Val Pro Pro Thr Leu Pro Met Glu Asn Arg Gly Asp Ser
            100                 105                 110

Gln Gln Gly Val Gln Gly Gly Arg Pro Val Glu Pro Gly Ala Gly Arg
        115                 120                 125

Ala Ala Pro Arg Gln Gly Phe Gln Tyr Asn Gly Ser Gly Gln Phe Arg
    130                 135                 140

Pro Gly Tyr Gly Gly Gly Arg Gly Tyr Ala Gln Asn Arg Gly Arg Thr
145                 150                 155                 160

Trp Ser Arg Ala Gly His Gly Arg Gly Met His Gly Pro Val Gly Gly
                165                 170                 175

Arg Gly Ala Ala Arg Pro Asn Pro Ala Gly Pro Gly Thr Met Thr Pro
            180                 185                 190

Ala Ser Gly Met Asp Gly Thr Thr Gly Thr Gly Pro Val Ala Gly Gly
        195                 200                 205

Ser Ile Gly Thr Ala Gly Asp Gln Ala Gly Met Ala Ala Val Leu Leu
    210                 215                 220

Gln Gln Ala Leu Ser Ala Leu Gln Gly Met Asn Ala Asp Lys Gly Gly
225                 230                 235                 240

Gly Ala Ala Gln Pro Ser Ala Ala Gln Gln Pro Val Met Pro Val Pro
                245                 250                 255
```

Ser Asp Gly Lys Lys Val His Pro Lys Pro Ala Val Val Glu Glu Lys
                260                 265                 270

Lys Lys Ser Asp Gln Glu Lys Glu Gly Phe Val Asp Ala Pro Lys Asn
            275                 280                 285

Asn Lys Ser Tyr Cys His Arg Cys Tyr Gly Lys Gly His Val Met Ser
        290                 295                 300

Glu Cys Ser Thr Ala Leu Phe Cys Glu Val Cys Gly Thr Asp Thr His
305                 310                 315                 320

Ile Lys His Lys Cys Pro Val Phe Asn Ala Pro Lys Val Tyr Ala Val
                325                 330                 335

Pro Ala Gly Phe Gly Ile Asn Lys Gly Gly Phe His Ile Pro Ser
            340                 345                 350

Asn Lys Lys Leu Val Lys Thr Lys Gln Asp Ala Arg Thr Ala Met Ile
        355                 360                 365

Gln Val Ser Glu Gly Gln Ile Ser Leu Glu Asn Val Asn Arg Glu Leu
370                 375                 380

Asp Arg Leu Leu Pro Gly Ser Ala Pro Trp Lys Val Glu Gln Val Ser
385                 390                 395                 400

Ala Ser Ser Tyr Arg Thr Thr Phe Pro Ser Ala Ser Glu Leu Gln Arg
                405                 410                 415

Met Val Glu Trp Gly Pro Val Arg Ala Lys Ser Gln Lys Ala Val Leu
            420                 425                 430

Glu Phe Ile Ala Ser Thr Ser Met Ala Glu Gly Arg Val Lys Ala Arg
        435                 440                 445

Leu Thr Asp Val Trp Val Gln Phe Asp Gly Leu Pro Ala Gln Leu Cys
450                 455                 460

Thr Tyr Gln His Ile Trp Gly Val Gly Ser Lys Leu Gly Val Thr Val
465                 470                 475                 480

Glu Val Asp Met Pro Phe Phe Arg Lys His Gly Ile Cys Arg Met Leu
                485                 490                 495

Val Ala Val Ile Asp Pro Glu Ala Ile Pro Phe Ala Gly Asp Val Glu
            500                 505                 510

Ile Asn Lys Ile Ile Tyr Glu Val His Tyr Trp Val Glu Gln Gly Pro
        515                 520                 525

Leu Asp Asp Glu Pro Thr Pro Met Val Ser Asp Leu Gly Gly Asp Asp
530                 535                 540

Gln Gly Asn Gly Asp Asn Ser Lys Gln Asn Asn Ala Lys Glu Gly Asn
545                 550                 555                 560

Glu Gln Phe Lys Met Pro Gly Glu Glu Gly Arg Asp Gly Glu Glu Lys
                565                 570                 575

Lys Gly Ser Asn Asp Val Gly Glu His Lys Gln Val Met Asp Ala Ala
            580                 585                 590

Pro Val Asp Asp Gly Gln Ala Leu Gln Cys Asp Glu Glu Asn Arg Leu
        595                 600                 605

Ala Val Phe
    610

<210> SEQ ID NO 19
<211> LENGTH: 645
<212> TYPE: DNA
<213> ORGANISM: Zea mays

<400> SEQUENCE: 19
atgaagatgg gaaagagtag gaaagaacca aggggggcggt caggaggtat acttatgggt          60

```
attgatctca atgtgaactc atcagagaag aataacgaca attttaatgc gagatggcct      120
tttctattca atgcgcctga attcaagttc gaacttggat ggctgttgcg ggagggattc      180
tgggagatgg tcactcaaat ttggtcaaag gagtatggtg gagatactgc cattgagaga      240
tggcagcgaa aaataaggaa gttaagacaa tacttgagag aagtagacat gcgcagtttt      300
cttcgtaata ggctcgcggc catgttacga gaagaagagg ttaagtggta ccagagagca      360
aaaactaaag gtttgctgga agggatgcg aacactaaat atttccatct ggtcgcgaat       420
ggacgcaata tcatggaagg gatagtgatt agatggtcat ttctaggcaa taacttccaa      480
actaagaagg ggctacggca aggccttaaa attaacttcc ataaaagtga aatcttctgc      540
tttggtgcgg ctaaagaaag tgaacattta tactcccaac ttttcggatg tactctttcg      600
aggaacctac tggtgtcgtt tctggggact actccaaaag cgtga                     645
```

```
<210> SEQ ID NO 20
<211> LENGTH: 214
<212> TYPE: PRT
<213> ORGANISM: Zea mays

<400> SEQUENCE: 20

Met Lys Met Gly Lys Ser Arg Lys Glu Pro Arg Gly Arg Ser Gly Gly
1               5                   10                  15

Ile Leu Met Gly Ile Asp Leu Asn Val Asn Ser Ser Glu Lys Asn Asn
            20                  25                  30

Asp Asn Phe Asn Ala Arg Trp Pro Phe Leu Phe Asn Ala Pro Glu Phe
        35                  40                  45

Lys Phe Glu Leu Gly Trp Leu Leu Arg Glu Gly Phe Trp Glu Met Val
    50                  55                  60

Thr Gln Ile Trp Ser Lys Glu Tyr Gly Gly Asp Thr Ala Ile Glu Arg
65                  70                  75                  80

Trp Gln Arg Lys Ile Arg Lys Leu Arg Gln Tyr Leu Arg Glu Val Asp
                85                  90                  95

Met Arg Ser Phe Leu Arg Asn Arg Leu Ala Ala Met Leu Arg Glu Glu
            100                 105                 110

Glu Val Lys Trp Tyr Gln Arg Ala Lys Thr Lys Gly Leu Leu Glu Gly
        115                 120                 125

Asp Ala Asn Thr Lys Tyr Phe His Leu Val Ala Asn Gly Arg Asn Ile
    130                 135                 140

Met Glu Gly Ile Val Ile Arg Trp Ser Phe Leu Gly Asn Asn Phe Gln
145                 150                 155                 160

Thr Lys Lys Gly Leu Arg Gln Gly Leu Lys Ile Asn Phe His Lys Ser
                165                 170                 175

Glu Ile Phe Cys Phe Gly Ala Ala Lys Glu Ser Glu His Leu Tyr Ser
            180                 185                 190

Gln Leu Phe Gly Cys Thr Leu Ser Arg Asn Leu Leu Val Ser Phe Leu
        195                 200                 205

Gly Thr Thr Pro Lys Ala
    210

<210> SEQ ID NO 21
<211> LENGTH: 234
<212> TYPE: DNA
<213> ORGANISM: Zea mays

<400> SEQUENCE: 21
```

```
atgcgagtca tatgcgttgt tgctagatac atgtctaatc ctgattatgg tggtgattta    60
gacaggagga gatctctttc agaagctgag tatatggcaa ttgcagaagt tactaaggaa   120
gccttatggt tgaaagatca gatgattact gagaaatcca acatattga tattcgttat    180 cacttcattc gtgatatcat tggagaacgt gtatttgcac agcagtttaa atga          234
```

<210> SEQ ID NO 22
<211> LENGTH: 77
<212> TYPE: PRT
<213> ORGANISM: Zea mays

<400> SEQUENCE: 22

```
Met Arg Val Ile Cys Val Val Ala Arg Tyr Met Ser Asn Pro Asp Tyr
1               5                   10                  15

Gly Gly Asp Leu Asp Arg Arg Arg Ser Leu Ser Glu Ala Glu Tyr Met
                20                  25                  30

Ala Ile Ala Glu Val Thr Lys Glu Ala Leu Trp Leu Lys Asp Gln Met
            35                  40                  45

Ile Thr Glu Lys Ser Lys His Ile Asp Ile Arg Tyr His Phe Ile Arg
        50                  55                  60

Asp Ile Ile Gly Glu Arg Val Phe Ala Gln Gln Phe Lys
65                  70                  75
```

<210> SEQ ID NO 23
<211> LENGTH: 693
<212> TYPE: DNA
<213> ORGANISM: Zea mays

<400> SEQUENCE: 23

```
atggcgtgcc acctgagatc tgctagcatg ccttcgagcc ctcgctccgt tgaggaacag    60
attctgagcc tgaaagtagc catctctctg ccttcagtga ccatcgaaac catggtggat   120
agtctgagca agctcgggag catctacagc cacatagacg cgctcgcatc cctgcccagc   180
tgccagagga aggcaatgga ggaggagctc gagcgctccg ttgtcctgct tgacctctgc   240
agcgccatgc aagagagctt tgcagaactc aaggccagtg tccaggagac gcagttggct   300
ctcaaaagag gagacgacgc ggctcttcat gccaagattc agtgctatgc gcgctcagct   360
aagaaggcac agaagctgtt caagaaggtc aacaagaaga ctgcctccga catcaaggga  420
tgcagggtga tcagcctggt cgctgaagcg agggaagttg ccctatcgat cctcgagtcg   480
acactgcatc tcctggcgaa gcagattgcg gtcccaagtc cagcaagtg gtcacttgta   540 tccaaatcgt tccagaagaa gagaatcatg tgtgaggcgg agcagttgca agggttggag   600
ccggagattg ctggtcttga gagcggagtt gggactttgt tcaggacgtt gatccagagc   660
agagtttctc ttctcaatgc tcttagtttg tag                                693
```

<210> SEQ ID NO 24
<211> LENGTH: 214
<212> TYPE: PRT
<213> ORGANISM: Zea mays

<400> SEQUENCE: 24

```
Met Lys Met Gly Lys Ser Arg Lys Glu Pro Arg Gly Arg Ser Gly Gly
1               5                   10                  15

Ile Leu Met Gly Ile Asp Leu Asn Val Asn Ser Ser Glu Lys Asn Asn
                20                  25                  30

Asp Asn Phe Asn Ala Arg Trp Pro Phe Leu Phe Asn Ala Pro Glu Phe
            35                  40                  45
```

```
Lys Phe Glu Leu Gly Trp Leu Leu Arg Glu Gly Phe Trp Glu Met Val
 50                  55                  60

Thr Gln Ile Trp Ser Lys Glu Tyr Gly Gly Asp Thr Ala Ile Glu Arg
 65                  70                  75                  80

Trp Gln Arg Lys Ile Arg Lys Leu Arg Gln Tyr Leu Arg Glu Val Asp
                 85                  90                  95

Met Arg Ser Phe Leu Arg Asn Arg Leu Ala Ala Met Leu Arg Glu Glu
            100                 105                 110

Glu Val Lys Trp Tyr Gln Arg Ala Lys Thr Lys Gly Leu Leu Glu Gly
        115                 120                 125

Asp Ala Asn Thr Lys Tyr Phe His Leu Val Ala Asn Gly Arg Asn Ile
    130                 135                 140

Met Glu Gly Ile Val Ile Arg Trp Ser Phe Leu Gly Asn Asn Phe Gln
145                 150                 155                 160

Thr Lys Lys Gly Leu Arg Gln Gly Leu Lys Ile Asn Phe His Lys Ser
                165                 170                 175

Glu Ile Phe Cys Phe Gly Ala Ala Lys Glu Ser Glu His Leu Tyr Ser
            180                 185                 190

Gln Leu Phe Gly Cys Thr Leu Ser Arg Asn Leu Leu Val Ser Phe Leu
        195                 200                 205

Gly Thr Thr Pro Lys Ala
    210

<210> SEQ ID NO 25
<211> LENGTH: 693
<212> TYPE: DNA
<213> ORGANISM: Zea mays

<400> SEQUENCE: 25
atggcgtgcc acctgagatc tgctagcatg ccttcgagcc ctcgctccgt tgaggaacag      60
attctgagcc tgaaagtagc catctctctg ccttcagtga ccatcgaaac catggtggat     120
agtctgagca agctcgggag catctacagc cacatagacg cgctcgcatc cctgcccagc     180
tgccagagga aggcaatgga ggaggagctc gagcgctccg ttgtcctgct tgacctctgc     240
agcgccatgc aagagagctt gcagaactca aggccagtg tccaggagac gcagttggct     300
ctcaaaagag agacgacgc ggctcttcat gccaagattc agtgctatgc gcgctcagct     360
aagaaggcac agaagctgtt caagaaggtc aacaagaaga ctgcctccga catcaaagga     420
tgcagggtga tcagcctggt cgctgaagcg agggaagttg ccctatcgat cctcgagtcg     480
acactgcatc tcctggcgaa gcagattgcg gtcccaagtc cagcaagtg gtcacttgta     540 tccaaatcgt tccagaagaa gagaatcatg tgtgaggcgg agcagttgca agggttggag     600
ccggagattg ctggtcttga gagcggagtt gggactttgt tcaggacgtt gatccagagc     660
agagtttctc ttctcaatgc tcttagtttg tag                                  693

<210> SEQ ID NO 26
<211> LENGTH: 230
<212> TYPE: PRT
<213> ORGANISM: Zea mays

<400> SEQUENCE: 26

Met Ala Cys His Leu Arg Ser Ala Ser Met Pro Ser Ser Pro Arg Ser
  1               5                  10                  15

Val Glu Glu Gln Ile Leu Ser Leu Lys Val Ala Ile Ser Leu Pro Ser
             20                  25                  30
```

```
Val Thr Ile Glu Thr Met Val Asp Ser Leu Ser Lys Leu Gly Ser Ile
         35                  40                  45

Tyr Ser His Ile Asp Ala Leu Ala Ser Leu Pro Ser Cys Gln Arg Lys
 50                  55                  60

Ala Met Glu Glu Leu Glu Arg Ser Val Val Leu Leu Asp Leu Cys
 65                  70                  75                  80

Ser Ala Met Gln Glu Ser Phe Ala Glu Leu Lys Ala Ser Val Gln Glu
                 85                  90                  95

Thr Gln Leu Ala Leu Lys Arg Gly Asp Asp Ala Ala Leu His Ala Lys
            100                 105                 110

Ile Gln Cys Tyr Ala Arg Ser Ala Lys Lys Ala Gln Lys Leu Phe Lys
            115                 120                 125

Lys Val Asn Lys Lys Thr Ala Ser Asp Ile Lys Gly Cys Arg Val Ile
130                 135                 140

Ser Leu Val Ala Glu Ala Arg Glu Val Ala Leu Ser Ile Leu Glu Ser
145                 150                 155                 160

Thr Leu His Leu Leu Ala Lys Gln Ile Ala Val Pro Ser Pro Ser Lys
                165                 170                 175

Trp Ser Leu Val Ser Lys Ser Phe Gln Lys Lys Arg Ile Met Cys Glu
            180                 185                 190

Ala Glu Gln Leu Gln Gly Leu Glu Pro Glu Ile Ala Gly Leu Glu Ser
            195                 200                 205

Gly Val Gly Thr Leu Phe Arg Thr Leu Ile Gln Ser Arg Val Ser Leu
210                 215                 220

Leu Asn Ala Leu Ser Leu
225                 230

<210> SEQ ID NO 27
<211> LENGTH: 309
<212> TYPE: DNA
<213> ORGANISM: Zea mays

<400> SEQUENCE: 27
atggcggcgg gaaagctggg gcagcagctg atgacgaggc tgcacctcgc gaggacccga      60
tcgtcggcga cggcggacgt gccgcggggc cacctggcgg tgtacgtggg cgaggggcgg     120
aagcggctgg tcatcccgac ggcgtgcctc agccacccgg ccttcgtcac gctgctgaag     180
cgggtggagg acgagttcgg cttcgaccac cgctgcggcg gcctcaccat cccctgcgcc     240
tccgagaccg agttcgctca catcgtcggc gccgccgccg ccgccgggga cgaccaccac     300
catcactga                                                            309

<210> SEQ ID NO 28
<211> LENGTH: 102
<212> TYPE: PRT
<213> ORGANISM: Zea mays

<400> SEQUENCE: 28

Met Ala Ala Gly Lys Leu Gly Gln Gln Leu Met Thr Arg Leu His Leu
 1               5                  10                  15

Ala Arg Thr Arg Ser Ser Ala Thr Ala Asp Val Pro Arg Gly His Leu
            20                  25                  30

Ala Val Tyr Val Gly Glu Gly Arg Lys Arg Leu Val Ile Pro Thr Ala
            35                  40                  45

Cys Leu Ser His Pro Ala Phe Val Thr Leu Leu Lys Arg Val Glu Asp
 50                  55                  60
```

Glu Phe Gly Phe Asp His Arg Cys Gly Gly Leu Thr Ile Pro Cys Ala
65                  70                  75                  80

Ser Glu Thr Glu Phe Ala His Ile Val Gly Ala Ala Ala Ala Gly
                85                  90                  95

Asp Asp His His His His
            100

<210> SEQ ID NO 29
<211> LENGTH: 309
<212> TYPE: DNA
<213> ORGANISM: Zea mays

<400> SEQUENCE: 29
atggcggcgg gaaagctggg gcagcagctg atgacgaggc tgcacctcgc gaggacccga      60
tcgtcggcga cggcggacgt gccgcggggc cacctggcgg tgtacgtggg cgaggggcgg     120
aagcggctgg tcatcccgac ggcgtgcctc agccacccgg ccttcgtcac gctgctcaag     180
cgggtggagg acgagttcgg cttcgaccac cgctgcggcg gcctcaccat ccctgcgcc      240 tccgagaccg agttcgctca catcgtcggc gccgccgccg ccgccgggga cgaccaccac     300
catcactga                                                             309

<210> SEQ ID NO 30
<211> LENGTH: 102
<212> TYPE: PRT
<213> ORGANISM: Zea mays

<400> SEQUENCE: 30

Met Ala Ala Gly Lys Leu Gly Gln Gln Leu Met Thr Arg Leu His Leu
1               5                   10                  15

Ala Arg Thr Arg Ser Ser Ala Thr Ala Asp Val Pro Arg Gly His Leu
                20                  25                  30

Ala Val Tyr Val Gly Glu Gly Arg Lys Arg Leu Val Ile Pro Thr Ala
            35                  40                  45

Cys Leu Ser His Pro Ala Phe Val Thr Leu Leu Lys Arg Val Glu Asp
        50                  55                  60

Glu Phe Gly Phe Asp His Arg Cys Gly Gly Leu Thr Ile Pro Cys Ala
65                  70                  75                  80

Ser Glu Thr Glu Phe Ala His Ile Val Gly Ala Ala Ala Ala Gly
                85                  90                  95

Asp Asp His His His His
            100

<210> SEQ ID NO 31
<211> LENGTH: 512
<212> TYPE: DNA
<213> ORGANISM: Zea mays

<400> SEQUENCE: 31
atggcggcgg gaaagctggg gcagcagctg atgacgaggc tgcacctcgc gaggacccga      60
ccgtcggcga cggcggacgt gccgcggggc cacctggcgg tgtacgtggg cgaggggcgg     120
aagcggctgg tcatcccaac ggcgtgcctc agccacccag ccttcgtcac gctgctgaag     180
cgggtggagg acgagttcgg cttcgaccac cgctgcggcg gcctcaccat ccctgcgcc      240 tccgagaccg agttcgctca catcgtgggc gccgccgccg ccggggacgg ccaccaccat     300
cactgacgat cgcgtgcgtg cccgcgccga tcgatcgagt tagagtccgg ccgtgtcgat     360

```
agattaattc cgcttccagt tccacctagc taggacaaaa ttattgttct cttttggggt    420
ggtgtcgatc gtagcagcaa tagtgttggg ttttgcttga cgacactgta aagattgtga    480
ttgggaattg aagaataag  ctcttctctc ac                                  512
```

<210> SEQ ID NO 32
<211> LENGTH: 101
<212> TYPE: PRT
<213> ORGANISM: Zea mays

<400> SEQUENCE: 32

```
Met Ala Ala Gly Lys Leu Gly Gln Gln Leu Met Thr Arg Leu His Leu
1               5                   10                  15

Ala Arg Thr Arg Pro Ser Ala Thr Ala Asp Val Pro Arg Gly His Leu
            20                  25                  30

Ala Val Tyr Val Gly Glu Gly Arg Lys Arg Leu Val Ile Pro Thr Ala
        35                  40                  45

Cys Leu Ser His Pro Ala Phe Val Thr Leu Leu Lys Arg Val Glu Asp
    50                  55                  60

Glu Phe Gly Phe Asp His Arg Cys Gly Gly Leu Thr Ile Pro Cys Ala
65                  70                  75                  80

Ser Glu Thr Glu Phe Ala His Ile Val Gly Ala Ala Ala Gly Asp
                85                  90                  95

Gly His His His His
        100
```

<210> SEQ ID NO 33
<211> LENGTH: 1501
<212> TYPE: DNA
<213> ORGANISM: Zea mays

<400> SEQUENCE: 33

```
cctatgcaaa cctagattaa atttatagtg ggatttaacc caaataatgc atgccccgct     60
aatgggtgat ggatttcccc tcataagttt ttaccatatg gtcatttcct gccatcctaa    120
caacttctaa ttcatgaatt ggattggttg acataacccc ataaaattgt gggttgggta    180
aagcagttaa tttgacatgg ggttgaggta gatatgggat ggaattttttg ttttaagagc    240 aatggcatca gctctactat ttattaattt aaaagggaaa acaaatagtt cataaaattg    300
tgtagagtag aagctagcta gctagcattg gtcagaataa gcaggacaca cctgggtgag    360
agaagagagc ttattcttcc aatccccaat cacaatcttt acagtgtcgt caagcaaaaa    420
cccaatcact attgctgcta cgacaccacc caaagagaa caataatttt gtcctagcta    480
ggtggaactg gaagcggaat taatctatcg acacggccgg actcgatcga tcggcgcggg    540
cacgcacgcg atcgtcagtg atggtggtgg tcgtccccgg cggcggcggc ggcgccgacg    600
atgtgagcga actcggtctc ggaggcgcag gggatggtga ggccgccgca gcggtggtcg    660
aagccgaact cgtcctccac cgcttgagc agcgtgacga aggccgggtg gctgaggcac    720
gccgtcggga tgaccagccg cttccgcccc tcgcccacgt acaccgccag gtggccccgc    780
ggcacgtccg ccgtcgccga cgatcgggtc ctcgcgaggt gcagcctcgt catcagctgc    840
tgccccagct ttcccgccgc catctctagc tctagctgtg tgtgtcggtg attgttgcac    900
aaagtcgtgt gtatagctct agcttgctat agctagagtg gtgctgctag atttggagct    960
caagagcttt gtgtggcgac ctgtgctgtg aggaccaagg ttgcactggg ccggtctttt   1020
atagcgcctc acaccagcta gctcagtctc aggcagcatg catggagatg gagccaatct   1080
```

```
tgccatggca cccaacaacg cgcgcctacc ggataaatta gaaagaatca tggaagcaca    1140
gtacggagta gtagtgtagt gtggcacgca ccacttgcag tttcttgttg gtgatatgat    1200
gatgatcata aagctgggca tatgcatgtc aatcacatgc tgcatgcagc agcactggca    1260
ctaatgagta gtgatgtctc taaaaagtac cccaccatt cacaaatact aacaccattg     1320
atttaaaaaa aactttaaac actcgtctta tataaaatat aaaatataaa attttaagtt    1380
ataacttatt tttctaataa gacgagtgat aaaaaattta aaaagaacgg tgtcatatat    1440
ttatgaacgg atgaagtata ggacaacatt gattttttt aaaaaaaaaa ttaatcactc     1500
a                                                                    1501

<210> SEQ ID NO 34
<211> LENGTH: 1501
<212> TYPE: DNA
<213> ORGANISM: Zea mays

<400> SEQUENCE: 34
ccctatgcaa acctagatta aatttatagt gggatttaac ccaaataatg catgccccgc      60
taatgggtga tggatttccc ctcataagtt tttaccatat ggtcatttcc tgccatccta    120
acaacttcta attcatgaat tggattggtt gacataaccc cataaaattg tgggttgggt    180
aaagcagtta atttgacatg gggttgaggt agatatggga tggaattttt gtttaagag     240 caatggcatc agctctacta tttattaatt taaaagggaa aacaaatagt tcataaaatt    300
gtgtagagta gaagctagct agctagcatt ggtcagaata agcaggacac acctgggtga    360
gagaagagag cttattcttc caatccccaa tcacaatctt tacagtgtcg tcaagcaaaa    420
acccaatcac tattgctgct acgacaccac cccaaagaga acaataattt tgtcctagct    480
aggtggaact ggaagcggaa ttaatctatc gacacggccg gactcgatcg atcggcgcgg    540
gcacgcacgc gatcgtcagt gatggtggtg gtcgtccccg gcggcggcgg cggcgccgac    600
gatgtgagcg aactcggtct cggaggcgca ggggatggtg aggccgccgc agcggtggtc    660
gaagccgaac tcgtcctcca cccgcttcag cagcgtgacg aaggccgggt ggctgaggca    720
cgccgtcggg atgaccagcc gcttccgccc ctcgcccacg tacaccgcca ggtggccccg    780
cggcacgtcc gccgtcgccg acgatcgggt cctcgcgagg tgcagcctcg tcatcagctg    840
ctgccccagc tttcccgccg ccatctctag ctctagctgt gtgtgtcggt gattgttgca    900
caaagtcgtg tgtatagctc tagcttgcta tagctagagt ggtgctgcta gatttggagc    960
tcaagagctt tgtgtggcga cctgctctgt gaggaccaag gttgcactgg gccggtcttt    1020
tatagcgcct cacaccagct agctcagtct caggcagcat gcatggagat ggagccaatc    1080
ttgccatggc acccaacaac gcgcgcctac cggataaatt agaaataatc atggaagcac    1140
agtacggagt agtagtgtaa tggcacgcac cacttgcagt ttcttgttgg tgatatgatg    1200
atgatcataa agctgggcat atgcatgtca atcacatgct gcatgcagca gcactggcac    1260
taatgagtag tgatgtctct aaaaagtaca cccaccattc acaaatacta acaccattga    1320
tttaaaaaaa actttaaaca ctcgtcttat ataaaatata aaatataaaa ttttaagtta    1380
taacttattt ttctaataag acgagtgata aaaaatttaa aaagaacggt gtcatatatt    1440
tatgaacgga tgaagtatag gacaacattg attttttta aaaaaaaaat taatcactca     1500
t                                                                    1501

<210> SEQ ID NO 35
<211> LENGTH: 507
```

```
<212> TYPE: DNA
<213> ORGANISM: Zea mays

<400> SEQUENCE: 35
atgcgagtca tatgcgttgt tgctagatac atgtctaatc ctggtaaaga gcattggaaa      60
gctgttcagt ggattttcag atatctacgt ggttcttcta gtgcttgttt atgttttggt     120
aaatctggag atggtctgat tggctatgtt gattcagatt atggtggtga tttagacagg     180
aggagatctc tttcaggtta tgtctttact attggagatt gtgctgtgag ttggaaagct     240
cgtttacagg atactgttgc tttgtctacc acagaagctg aatatatggc aattgcagaa     300
gttactaagg aagccttatg gttgaaaggt atatattcag agctatgtgg aattaagtct     360
tgcattacca tctattgtga tagccagagt gccattcatc tcaccaaaga tcagatgatt     420
actgagaaat ccaaacatat tgatattcgt tatcacttca ttcgtgatat cattggagaa     480
cgtgtatttg cacagcagtt taaatga                                         507

<210> SEQ ID NO 36
<211> LENGTH: 30
<212> TYPE: DNA
<213> ORGANISM: Zea mays

<400> SEQUENCE: 36
agctatacac acgactttgt gcaacaatca                                       30

<210> SEQ ID NO 37
<211> LENGTH: 30
<212> TYPE: DNA
<213> ORGANISM: Zea mays

<400> SEQUENCE: 37
cgacacacac agctagagct agagatggcg                                       30

<210> SEQ ID NO 38
<211> LENGTH: 509
<212> TYPE: DNA
<213> ORGANISM: Artificial Sequence
<220> FEATURE:
<223> OTHER INFORMATION: SAUR31 mutant in Zea mays
<220> FEATURE:
<221> NAME/KEY: 5'UTR
<222> LOCATION: (310)..(435)
<220> FEATURE:
<221> NAME/KEY: mutation
<222> LOCATION: (334)..(334)

<400> SEQUENCE: 38
tcagtgatgg tggtggtcgt ccccggcggc ggcggcggcg ccgacgatgt gagcgaactc      60
ggtctcggag gcgcagggga tggtgaggcc gccgcagcgg tggtcgaagc cgaactcgtc     120
ctccacccgc ttgagcagcg tgacgaaggc cgggtggctg aggcacgccg tcgggatgac     180
cagccgcttc cgcccctcgc ccacgtacac cgccaggtgg ccccgcggca cgtccgccgt     240
cgccgacgat cgggtcctcg cgaggtgcag cctcgtcatc agctgctgcc ccagctttcc     300
cgccgccatc tctagctcta gctgtgtgtg tcgatgattg ttgcacaaag tcgtgtgtat     360
agctctagct tgctatagct agagtggtgc tgctagattt ggagctcaag agctttgtgt     420
ggcgacctgt gctgtgagga ccaaggttgc actgggccgg tcttttatag cgcctcacac     480
cagctagctc agtctcaggc agcatgcat                                       509
```

COLD-TOLERANT PLANT

CROSS-REFERENCE TO RELATED APPLICATIONS

This application is a U.S. National Phase of International Patent Application No. PCT/EP2016/078920, filed Nov. 26, 2016, which claims priority to European Patent Application No. 15196721.3, filed on Nov. 27, 2015, all of which are herein incorporated by reference in their entirety.

FIELD OF THE INVENTION

The present invention relates to the field of the modification of plants using molecular biological methods and marker technology and genetic engineering. It relates to a novel chill-tolerant plant, in particular a maize plant, as well as to the identification and molecular characterization and also to the use of genes and markers from a chromosomal interval of 25.7 kb, which in maize lines contains a locus for chill/cold tolerance. In a further aspect, the invention relates to the development of molecular markers to assist during breeding, in particular to avoid fixing of a "selective sweep" in a region with a low recombination rate.

BACKGROUND OF THE INVENTION

The expression "chill" means temperatures at which the maize plant can survive, but the growth is compromised or even substantially compromised. The optimal growth temperature for the germination of maize seeds and the development of maize plants is between 21-27° C. (Greaves J A (1996), Improving suboptimal temperature tolerance in maize-the search for variation. J Exp Bot 47: 307-323, 1996).

Thus, stress already occurs below temperatures of 20° C., which is a typical temperature in Northern Europe during planting times. Mild chilling stress with reduced photosynthesis in light and reduced growth is seen at 12-17° C., and severe chilling stress occurs together with cold-induced water stress, a type of drought stress, in light at 2-10° C. (Marocco A., Lorenzoni C and Fracheboud Y, 2005. Chilling stress in maize. Maydica, 50: 571-580).

Chill stress is accompanied by either photoinhibition and oxidative stress in light or gene expression alterations in the dark (summarized in Marocco et al., 2005). The heterotrophic phase (sowing up to the third leaf) is the most sensitive, but the early autotrophic phase is also affected by chill stress (Bhosale et al., 2007 Chilling Tolerance of Central European Maize Lines and their Factorial Crosses, Annals of Botany 100: 1315-1321). The long-term action of low temperatures results in irreversible damage to the cells and tissue (Greaves, 1996) and associated reduced growth and yield.

Early strong plant growth is viewed as an important indicator for high and stable yields, for example in maize, in particular in the cool climate of Central and Northern Europe. In addition, maize varieties with improved early plant growth result in better ground coverage and thus assist in reducing erosion and nitrate flushing at the beginning of the growth phase.

Several QTL (Quantitative Trait Locus) investigations have already been carried out in order to identify a genetic chill tolerance in maize Most of the studies analysed maize plants which were cultivated in growth chambers under optimal (25/22° C. and suboptimal (15/13° C.) conditions. In this regard, parameters such as the quantum efficiency of the photosy stem II, the maximum quantum efficiency of the photosystem II, the chlorophyll fluorescence, the chlorophyll content of the third leaf (SPAD), leaf area and dry weight of the seedling were measured (Fracheboud, Y., et al. "Identification of quantitative trait loci for cold-tolerance of photosynthesis in maize (Zea mays L.)." Journal of experimental botany 53.376 (2002): 1967-1977; Fracheboud, Y., et al. "Genetic analysis of cold-tolerance of photosynthesis in maize" Plant molecular biology 56.2 (2004): 241-253; Hund, A., et al. "QTL controlling root and shoot traits of maize seedlings under cold stress." Theoretical and applied genetics 109.3 (2004): 618-629; Hund, Andreas, et al. "Chill tolerance of the photosynthetic apparatus: pleiotropic relationship between photosynthetic performance and specific leaf area of maize seedlings." Molecular Breeding 16.4 (2005): 321-331; Guerra-Peraza, Orlene, et al. "Temperature at night affects the genetic control of acclimation to cold in maize seedlings." Maydica 56.4 (2012)), but in all of those experiments, no QTL was documented in the vicinity of the QTL on chromosome 4 described and cloned here. Leipner et al. (QTL studies reveal little relevance of chilling-related seedling traits for yield in maize. Theor Appl Genet (2008) 116:555-562) reported a QTL mapping experiment in the blossom and harvest phase in a field experiment when sowing at two different times. The parameters measured were flowering time, plant height, straw and ear dry weight, and the authors compared their identified QTLs with QTLs which were identified using growth chamber experiments in the germination phase, such as that published by Jompuk et al. (Mapping of quantitative trait loci associated with chilling tolerance in maize (Zea mays L.) seedlings grown under field conditions. Journal of experimental botany, 2005, 56. Jg., No. 414, p. 1153-1163.). Only a few common QTLs were detected. Leipner et al. concluded from this that the chill tolerance of seedlings apparently had no significant effect on yield.

Jompuk et al. (2005) determined the carbohydrate exchange and chlorophyll fluorescence, the operational quantum efficiency of photosystem II, the green colour of the third leaf (SPAD), the area of the third leaf and the dry weight of the seedling in the same population, and mapped a QTL for SPAD for early sowing and the operational quantum efficiency of the photosystem II on chromosome 4 at 31.1 Mb, which is approximately 6 Mb from the QTL of the present invention in position 37 Mb.

Using SSR markers, Presterl et al. 2007 ("Quantitative trait loci for early plant vigour of maize grown in chilly environments." Theoretical and Applied Genetics 114.6 (2007): 1059-1070) mapped a QTL of 4 cM on chromosome 4, but which has a physical size of approximately 155 Mb, which is no less than approximately 7% of the total genome for maize Although an advanced fine mapping study by Baliashvili was reported in 2011 (Feinkartierung eines QTL (Quantitative Trait Locus) für Kühletoleranz auf Chromosom 4 in Mais and dessen molekularbiologische and phänotypische Charakterisierung. Diss. Universitäts- and Landesbibliothek der Heinrich-Heine-Universität Düsseldorf, 2011 [Fine mapping of a QTL (quantitative trait locus) for chill tolerance on chromosome 4 in maize and its molecular biological and phenotype characterization, dissertation, Heinrich-Heine University Düsseidorf, 2011]), neither markers nor other sequence information was reported therein.

A recent QTL study has been published by Rodriguez et al. (Effects of selection for color intensity on antioxidant capacity in maize (Zea mays L.). Euphytica, 2013, 193. Jg., No. 3, p. 339-345.). The descendants of a cross between Flint maize and Dent maize were evaluated under controlled conditions, wherein the Dent maize line reacted sensitively to low temperatures and exhibited a drastic reduction in the chlorophyll content. The control temperatures in this case were 25/20° C., and the cool temperatures were set at 14/8° C. The measured parameters were the number of surviving plants under control and cool conditions, the dry weight of the seedling under control conditions, the quantum yield of photosystem II under control conditions and the total anthocyanin content. Four out of the 10 detected QTL regions overlapped with the QTL mapped by Presterl et al. in 2007 on chromosome 4, but no further investigations were carried out in respect of the genetic bases such as, for example, fine mapping of the regions or the identification of candidate genes.

In investigations of this type, generally, analysis of a parenteral origin of alleles by markers which flank a target locus is used to select individuals with a short intact donor chromosome segment around the target gene, and thus "linkage drag" can be reduced. Stam and Zeven (The theoretical proportion of the donor genome in near-isogenic lines of self-fertilizers bred by backcrossing. Euphytica, 1981, 30. Jg., No. 2, p. 227-238), however, showed that the expected length of a donor chromosome segment which is coupled with a target gene, even after six generations of backcrossing and combined with selection onto the target gene, is still 32 cM of a 100 cM chromosome. There are examples of negative genetically coded properties which remain coupled with a target gene under selection (Zeven, A C; Knott, D R; Johnson, R. Investigation of linkage drag in near isogenic lines of wheat by testing for seedling reaction to races of stem rust, leaf rust and yellow rust. Euphytica, 1983, 32. Jg., No. 2, p. 319-327).

In general, chill tolerance is an important feature in the further development of crop plants. In this regard, chill tolerance-conferring genes are known for other types of cultures. Thus, Ma et al. (in: COLD1 confers chilling tolerance in rice. Cell. 2015 Mar. 12; 160(6):1209-21), for example, describe the QTL COLD1 in rice. An overexpression of COLD1(jap) significantly increases chill tolerance. COLD1 codes for a regulator of the G-protein signal cascade. Furthermore, an SNP known as SNP2 is also described in COLD1 Similarly, chill tolerance is also considered to be an important aim for silo, grain and energy maize cultivation in many maize growing regions, in particular in the cool regions of Central and Northern Europe, but also in Southern Europe, where farmers would like to sow maize plants earlier in order to exploit the moisture of winters in the ground better. The discovery and characterization of chill tolerance-conferring genes and the provision of novel markers for chill tolerance in plants in general and in particular in crop plants, as well as the provision of plants with an increased chill tolerance, without these plants suffering further agronomic or breeding disadvantages, is thus of particular interest and an objective of this invention. Further aspects will become apparent to the person skilled in the art upon study of the description and examples below.

DETAILED DESCRIPTION OF THE INVENTION

In a first aspect of the present invention, this objective is achieved by means of the provision of a nucleic acid, which comprises a nucleic acid sequence selected from the group consisting of a) a nucleic acid sequence with one of the SEQ ID NOs: 29, 3, 7, 11, 15, 25 or 35, or a functional fragment thereof, b) a nucleic acid sequence which is complementary to a sequence from a), c) a nucleic acid sequence which has at least 80%, 85%, 90% or 95% or preferably at least 96%, 97%, 98%, or 99% identity with a sequence from a) or b), d) a nucleic acid sequence which differs from a nucleic acid sequence according to a), b) or c) depending on the degeneracy of the genetic code, e) a nucleic acid sequence which hybridizes with a nucleic acid sequence according to a), b) or c) under stringent conditions, f) a nucleic acid sequence which codes for a protein with one of the SEQ ID NOs: 30, 4, 8, 12, 16 or 26 or a homologue, analogue or orthologue thereof, or g) a nucleic acid sequence which codes for one or more RNAs which is/are capable of hybridizing with at least a portion of itself or with each other and of thus forming a double-stranded portion, wherein this nucleic acid matches over at least 19, 20, 21, 22, 23, 24 or 25, preferably at least 30, 32, 34, 36, 38 or 40, particularly preferably at least 50, 60, 70, 80, 90 or 100, or more particularly preferably at least 150, 200, 250, 300, 400, 500, 750 or 1000 successive nucleotides with one of the nucleic acid sequences selected from the group consisting of (i) a nucleic acid sequence with one of the SEQ ID NOs: 27, 17, 19, 5, 7, 23 or 25, (ii) a nucleic acid sequence which is complementary to a sequence from i), (iii) a nucleic acid sequence which has at least 80%, 85%, 90% or 95% or preferably at least 96%, 97%, 98%, or 99% identity with a sequence from (i) or (ii), (iv) a nucleic acid sequence which differs from a nucleic acid sequence according to (i), (ii) or (iii) in accordance with the degeneracy of the genetic code, (v) a nucleic acid sequence which hybridizes with a nucleic acid sequence according to (i), (ii) or (iii) under stringent conditions, (vi) a nucleic acid sequence which codes for a protein with one of the SEQ ID NOs: 28, 18, 20, 6, 8, 24 or 26, or a homologue, analogue or orthologue thereof, or vii) a nucleic acid sequence in antisense orientation to a nucleic acid sequence according to (i) to (vi).

The present invention results from studies by the inventors aimed at precisely identifying and localizing a chill tolerance-quantitative marker locus (quantitative trait locus (QTL)) on chromosome 4 of maize, cloning this QTL and sequencing and identifying the gene(s) which are responsible for the chill tolerance phenotype. The identified region of 25.7 kb (donor genotype) in total was investigated on a molecular level, and suitable candidate genes were identified (see FIG. 1). The functional validation carried out comprised the identification of TILLING mutants and gene expression studies. In this regard, the identified chill tolerance has been made useful for the first time on a breeding and genetic engineering level. During the course of the mapping and fine mapping studies, special molecular markers were developed which can be used diagnostically for the selection of plants with increased chill tolerance. Furthermore, the developed markers may also be used in order to specifically cross the genetic source of the increased chill tolerance in already available breeding material (for example existing varieties, elite lines, etc), and thus to keep the extent of the introgression produced low. In this manner, for the first time it has been possible to transmit the chill tolerance trait without bringing with it an extended genetic region of the centromer region of chromosome 4 from the donor. This is particularly advantageous, because it has been observed that this genetic region is strongly fixed and thus only allows a very small amount of genetic diversity and recombination frequency. If this genetic region, which in any case constitutes more than 5% of the total genome of maize, were to be transmitted with it, then it would drastically limit the further breeding usefulness of varieties with this important agronomic trait. Thus, the present invention advantageously and for the first time allows the identified chill tolerance trait to be exploited for breeding and at the same time reduces loss of genetic diversity (selective sweep) to a minimum.

Figure 2:
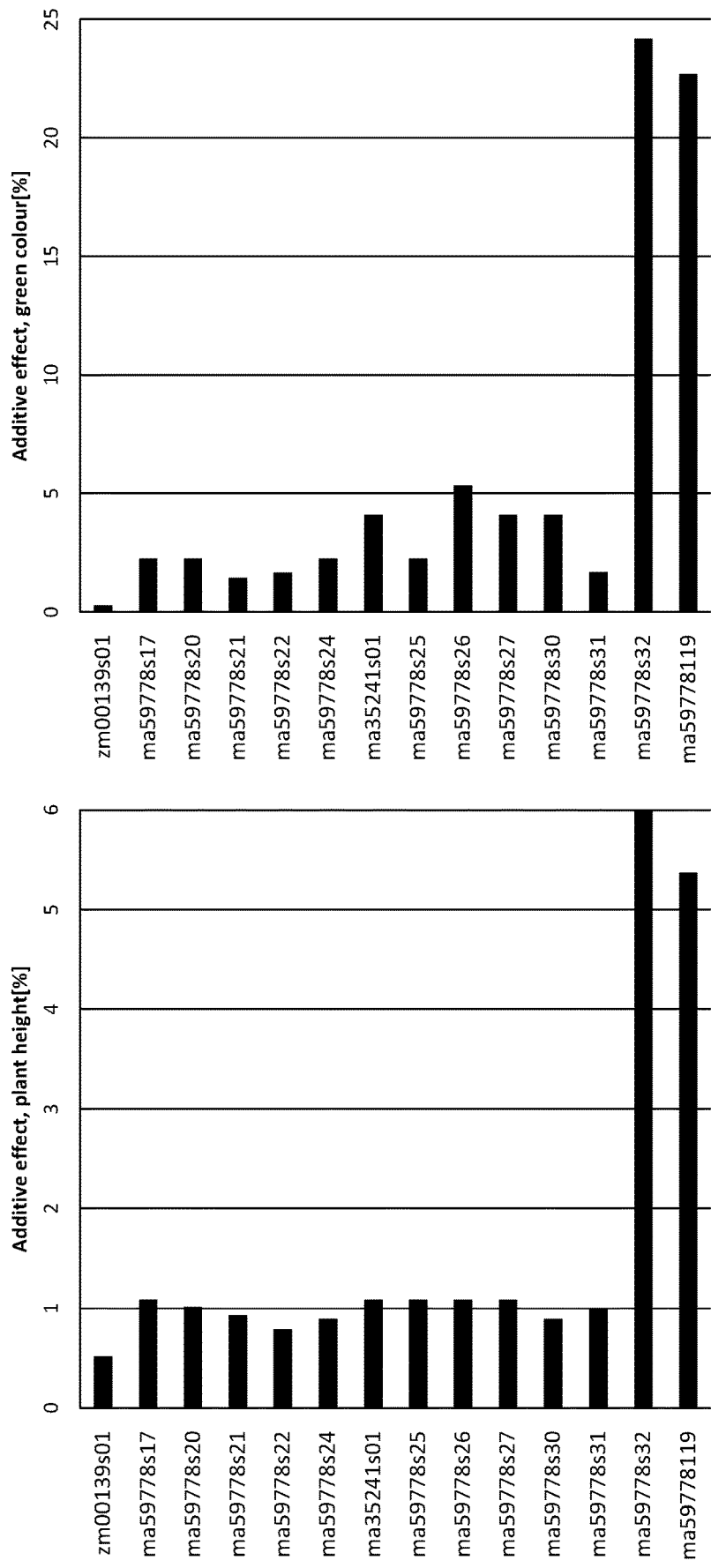

As a result of the analyses carried out in the context of the invention, a significant correlation of phenotype markers for chill tolerance with the region between the markers ma59778s31 and ma59778119 was found (see FIG. 2, for example). The discovery of a QTL on chromosome 4 in the Dent pool which explains 35% of the phenotypic variation for chill tolerance constitutes a decisive resource for breeding exploitation.

Because of the low recombination rate and the pericentromeric position of the QTL, in the present case it was particularly difficult to restrict the original region to a narrow interval and, instead of a half chromosome of 122 MB on which even more negative traits would have been inherited and which would have led to a loss of genetic diversity, only a few kb were crossed in breeding. With the knowledge regarding the genetic bases for the chill tolerance trait, it is now possible to exploit it alone and avoid linkage drag and reduced genetic diversity.

In the region around said QTL, by means of comparisons between the various plants and the associated database comparisons, several functional elements or genes could be identified (see examples) which alone or in combination are involved in chill tolerance. The following Tables Ia, Ib and Ic provide a list thereof.

TABLE 1a

Genetic elements and genes in the 25.7 kb target region (TH genotype; ORF—open reading frame as identified; SL—sensitive line; TH—tolerant line)

| SEQ ID NO: | Description | Position (SL) | Annotation |
|---|---|---|---|
| 29 | ORF TH-09 | 88663 | Auxin-responsive SAUR protein (SAUR31) |
| 3 | ORF TH-01 | 61977 | Retrotransposon gag Protein |
| 7 | ORF TH-02 | 63012 | Transposon Sb07g001920 from *Sorghum bicolor* |
| 11 | ORF TH-03 | 65848 | Transposon Sb07g001880 from *Sorghum bicolor* |
| 15 | ORF TH-04 | 70255 | Transposon Sb07g001880 from *Sorghum bicolor* |
| 25 | ORF TH-08 | 80491 | Transposon Sb07g001900 from *Sorghum bicolor* |
| 35 | ORF TH-11 | 79716 | Putative polyprotein, *Oryza sativa* ssp. *japonica* |
|  | Region TH-12 |  | Transposon Sb07g001920 from *Sorghum bicolor* |

TABLE 1b

Genetic elements and genes in the 25.7 kb target region, not present in the TH genotype or which have an altered, preferably reduced expression in the TH genotype (ORF—open reading frame as identified; SL—sensitive line; TH—tolerant line)

| SEQ ID NO: | Description | Position (SL) | Annotation |
|---|---|---|---|
| 17 | ORF SL-05 | 71918 | Transposable element, possible non-characterized protein, *Oryza sativa* subsp. *Japonica* |
| 19 | ORF SL-06 | 74307 | Retrotransposon, possible non-characterized protein OSJNBb0006B22.8, *Oryza sativa* subsp. *japonica* |
| 7 | ORF TH-02 | 63012 | Transposon Sb07g001920 from *Sorghum bicolor* |
| 25 | ORF TH-08 | 80491 | Transposon Sb07g001900 from *Sorghum bicolor* |
| 29 | ORF TH-09 | 88663 | Auxin-responsive SAUR protein (SAUR31) |

TABLE 1c

Genetic elements and genes in the 25.7 kb target region (SL genotype; ORF—open reading frame as identified; SL—sensitive line; TH—tolerant line)

| SEQ ID NO: | Description | Position (SL) | Annotation |
|---|---|---|---|
| 27 | ORF SL-09 | 88663 | Auxin-responsive SAUR protein (SAUR31) |
| 1 | ORF SL-01 | 61977 | Retrotransposon gag Protein |
| 5 | ORF SL-02 | 63012 | Transposon Sb07g001920 from *Sorghum bicolor* |
| 9 | ORF SL-03 | 65848 | Transposon Sb07g001880 from *Sorghum bicolor* |
| 13 | ORF SL-04 | 70255 | Transposon Sb07g001880 from *Sorghum bicolor* |
| 17 | ORF SL-05 | 71918 | Transposable element, possible non-characterized protein, *Oryza sativa* subsp. *Japonica* |
| 19 | ORF SL-06 | 74307 | Retrotransposon, possible non-characterized protein OSJNBb0006B22.8, *Oryza sativa* subsp. *japonica* |
| 23 | ORF SL-08 | 80491 | Transposon Sb07g001900 from *Sorghum bicolor* |
| 27 | ORF SL-09 | 88663 | Auxin-responsive SAUR protein (SAUR31) |
|  | Region SL-11 | 79716 | Putative polyprotein, *Oryza sativa* ssp. *japonica* |
| 21 | ORF SL-12 |  | Transposon Sb07g001920 from *Sorghum bicolor* |

ORF-09 (SAUR31), ORF-08 and ORF-02, which exhibited different expressions between the SL and TH lines, are of particular interest in the context of the present invention and are therefore preferred (see Table 1b). As an example, the expression rate of ORF-09 under chill stress was higher in the chill-sensitive lines (SL) than in the chill-tolerant lines (TH) and reduced over time.

Data from analyses of the gene ORF-09 or the associated annotation SAUR31 with SEQ ID NO: 27 (nucleotide sequence for the SL genotype), SEQ ID NO: 29 (nucleotide sequence for the TH genotype) and SEQ ID NO: 31 (nucleotide sequence for the maize genome reference line B73) with the aid of marker analyses and evaluation of recombination frequencies in the various lines SL, TH and B73 (FIG. 1) enabled SAUR31 to be positioned unequivocally within a section on chromosome 4 between the markers ma59778s31 and ma59778119, preferably between ma59778s32 and ma59778119. In this regard, SAUR31 is a gene which codes for the auxin-responsive protein (cf. SEQ ID NOs: 28, 30 and 32). SAUR genes are known to be involved in cell expansion, auxin-mediated signal transduction and root meristem development and also are positive regulators for leaf senescence (Xu, N.; Hagen, G; Guilfoyle, T. Multiple auxin response modules in the soybean SAUR 15A promoter. Plant Science, 1997, 126. Jg., No. 2, p. 193-201; Jain, M; Tyagi, A K; Khurana, J P. Genome-wide analysis, evolutionary expansion, and expression of early auxin-responsive SAUR gene family in rice (*Oryza sativa*). Genomics, 2006, 88. Jg., No. 3, p. 360-371; Jain, M; Khurana, J P. Transcript profiling reveals diverse roles of auxin-responsive genes during reproductive development and abiotic stress in rice. Febs Journal, 2009, 276. Jg., No. 11, p. 3148-3162; Spartz, A K, et al. The SAUR19 subfamily of SMALL AUXIN UP RNA genes promote cell expansion. The Plant Journal, 2012, 70. Jg., No. 6, p. 978-990; Hou et al. SAUR36, a small auxin up RNA gene, is involved in the promotion of leaf senescence in *Arabidopsis*. Plant physiology, 2013, 161. Jg., No. 2, p. 1002-1009). SAUR genes are primary auxin response genes which are involved in the auxin signalling pathway (Chen et al. Jun. Small auxin upregulated RNA (SAUR) gene family in maize: Identification, evolution, and its phylogenetic comparison with *Arabidopsis*, rice, and sorghum. Journal of integrative plant biology, 2014, 56. Jg., No. 2, p. 133-150). They can be divided into various groups and have already been found in *A. thaliana*, rice and soya in different functions. In maize, putative SAUR genes were identified in B73 genome 79. (Chen et al. Small auxin upregulated RNA (SAUR) gene family in maize: Identification, evolution, and its phylogenetic comparison with *Arabidopsis*, rice, and sorghum. Journal of integrative plant biology, 2014, 56. Jg., No. 2, p. 133-150). The candidate gene ORF-09 was mentioned as ZmSAUR37, but the significance conferringchill tolerance was not described earlier and was completely unexpected. In the studies at the basis of the invention, different levels of expression of SAUR31 in the sensitive (SL) compared with the tolerant (TH) lines during chill stress was observed (Table 1b). The promoter sequence shows a high number of polymorphisms between the investigated lines, while the amino acid sequence for the coded protein was largely unaltered. Although it can be postulated that the differing expression of the putative SAUR gene mediated by variation in its promoter is involved in the present chill-tolerant phenotype, all other genes or regions (as can be seen in Tables 1a-c) within the chill tolerance-conferring QTL, individually or together, optionally together with SAUR are responsible for the chill tolerance phenotype or have an influence on the degree of chill tolerance. In total, they constitute preferred aspects of the present invention.

Furthermore, the objective of the invention is also achieved by means of the provision of an expression cassette, which comprises a nucleic acid with a nucleic acid sequence which is selected from the group consisting of a) a nucleic acid sequence with one of the SEQ ID NOs: 29, 3, 7, 11, 15, 25 or 35, or a functional fragment thereof, b) a nucleic acid sequence which is complementary to a sequence from a), c) a nucleic acid sequence which has at least 80%, 85%, 90% or 95% or preferably at least 96%, 97%, 98%, or 99% identity with a sequence from a) or b), d) a nucleic acid sequence which differs from a nucleic acid sequence according to a), b) or c) depending on the degeneracy of the genetic code, e) a nucleic acid sequence which hybridizes with a nucleic acid sequence according to a), b) or c) under stringent conditions, f) a nucleic acid sequence which codes for a protein with one of the SEQ ID NOs: 30, 4, 8, 12, 16 or 26 or a homologue, analogue or orthologue thereof, or g) a nucleic acid sequence which codes for one or more RNAs which is/are capable of hybridizing with at least a portion of itself or with each other and of thus forming a double-stranded portion, wherein this nucleic acid matches over at least 19, 20, 21, 22, 23, 24 or 25, preferably at least 30, 32, 34, 36, 38 or 40, particularly preferably at least 50, 60, 70, 80, 90 or 100, or more particularly preferably at least 150, 200, 250, 300, 400, 500, 750 or 1000 successive nucleotides with one of the nucleic acid sequences selected from the group consisting of (i) a nucleic acid sequence with one of the SEQ ID NOs: 27, 17, 19, 5, 7, 23 or 25, (ii) a nucleic acid sequence which is complementary to a sequence from i), (iii) a nucleic acid sequence which has at least 80%, 85%, 90% or 95% or preferably at least 96%, 97%, 98%, or 99% identity with a sequence from (i) or (ii), (iv) a nucleic acid sequence which differs from a nucleic acid sequence according to (i), (ii) or (iii) in accordance with the degeneracy of the genetic code, (v) a nucleic acid sequence which hybridizes with a nucleic acid sequence according to (i), (ii) or (iii) under stringent conditions, (vi) a nucleic acid sequence which codes for a protein with one of the SEQ ID NOs: 28, 18, 20, 6, 8, 24 or 26, or a homologue, analogue or orthologue thereof, or vii) a nucleic acid sequence in antisense orientation to a nucleic acid sequence according to (i) to (vi).

A nucleic acid or expression cassette in accordance with the invention is preferably suitable, after transcription or after expression in a plant, of conferring the property of chill tolerance or of increasing the chill tolerance of the plant.

The principle of expression cassettes, their construction and their components are known to the person skilled in the art and have been described in the literature (Sambrook et al. 2001, Molecular cloning: A laboratory manual (3-volume set) (Vol. 999). Cold Spring Harbor, New York: Cold Spring Harbor Laboratory Press). Cassettes of this type consist of at least a gene to be expressed and a promoter which is operatively connected to it. Promoters of this type may be capable of mediating the transgenic expression of specific genes in a plant development-specific or tissue-specific manner such as, for example, in WO 2003/006660 or WO 2000/026388. As an example, DE 10 2005 021365 describes a flower-specific expression cassette. They may also contain at least one terminator sequence which is functional in plant cells or plant organisms (for example as described in WO 2003/008596). Expression cassettes may also contain one or more resistance genes which allow for the selection of successfully transformed or transfected cells. The person skilled in the art will be aware of various resistance genes (selection markers) which are known in the prior art (Miki, B; McHugh, p. Selectable marker genes in transgenic plants: applications, alternatives and biosafety. Journal of Biotechnology, 2004, 107. Jg., No. 3, p. 193-232). These may include a resistance to kanamycin, streptomycin or ampicillin, for example. Expression cassettes may be present as linear nucleic acid or in a vector or plasmid.

In one embodiment of the expression cassette of the present invention, a nucleic acid in accordance with the invention is operatively connected to a constitutive promoter such as, for example, the 35S promoter (Odell, J T; Nagy, F; Chua, N H. Identification of DNA sequences required for activity of the cauliflower mosaic virus 35S promotor. 1985, U.S. Pat. No. 5,352,605 A), a chill/cold-inducible promoter such as, for example, BN115 (U.S. Pat. No. 5,847,102 A) or a promoter such as, for example, p63 (EP 2 116 606 B1), which is active in particular in the early development of plants or in young plant tissue, wherein "early development" means the first 12 weeks following germination, in particular the first 8 weeks following germination, and in particular the first 4 weeks following germination.

In a preferred embodiment of the present invention, the expression cassette comprises a nucleic acid, which comprises a nucleic acid sequence selected from the group consisting of a) a nucleic acid sequence with SEQ ID NO:

29, or a functional fragment thereof, b) a nucleic acid sequence which is complementary to a sequence from a), c) a nucleic acid sequence which has at least 80%, 85%, 90% or 95% or preferably at least 96%, 97%, 98%, or 99% identity with a sequence from a) or b), d) a nucleic acid sequence which differs from a nucleic acid sequence according to a), b) or c) depending on the degeneracy of the genetic code, e) a nucleic acid sequence which hybridizes with a nucleic acid sequence according to a), b) or c) under stringent conditions, or f) a nucleic acid sequence which codes for a protein with one of the SEQ ID NOs: 30 or a homologue, analogue or orthologue thereof, preferably operatively connected with a promoter which comprises the nucleotide sequence with SEQ ID NO: 33, or with an allele variant or a modified form of a promoter which comprises the nucleotide sequence with SEQ ID NO: 34, wherein the allele variant or the modified form produces a comparable expression rate or level of expression to the promoter which comprises the nucleotide sequence with SEQ ID NO: 33. An "allele variant" or a "modified form of the promoter" means a promoter which has an expression rate or expression level which is reduced by more than 5%, 10%, 15%, 20%, 25%, 30%, 40% or 50% compared with the expression rate or expression level caused by the promoter with the nucleotide sequence with SEQ ID NO: 34. A "comparable expression rate or expression level" means that the allele variant or the modified form of the promoter which comprises the nucleotide sequence with SEQ ID NO: 34 essentially has an expression rate or expression level which differs by no more than 20%, 18%, 16%, 14% or 12%, preferably by no more than 10%, 9%, 8%, 7% or 6%, or particularly preferably no more than 5%, 4%, 3%, 2%, 1%, 0.5% or 0% from the expression rate or expression level of the promoter which comprises the nucleotide sequence with SEQ ID NO: 33.

Furthermore, the present invention also includes a chill stress-responsive promoter comprising a nucleotide sequence with SEQ ID NO: 33 or 34 or a nucleotide sequence which is complementary to the nucleotide sequence with SEQ ID NO: 33 or 34 or a nucleotide sequence which hybridizes with the nucleotide sequence with SEQ ID NO: 33 or 34, or a nucleotide sequence which is complementary to the nucleotide sequence with SEQ ID NO: 33 or 34, as well as an expression cassette comprising the chill stress-responsive promoter, a vector comprising the chill stress-responsive promoter, or the expression cassette which comprises the chill stress-responsive promoter, a host cell or a plant or parts thereof comprising the chill stress-responsive promoter as a transgene, the expression cassette which comprises the chill stress-responsive promoter, or the vector comprising the chill stress-responsive promoter, or the expression cassette which comprises the chill stress-responsive promoter.

In a further preferred embodiment of the present invention, the expression cassette comprises a nucleic acid which comprises a nucleotide sequence which codes for one or more RNAs which is/are capable of hybridizing with at least a portion of itself or with each other and of thus forming a double-stranded portion, wherein this nucleic acid matches over at least 19, 20, 21, 22, 23, 24 or 25, preferably at least 30, 32, 34, 36, 38 or 40, particularly preferably at least 50, 60, 70, 80, 90 or 100, or more particularly preferably at least 150, 200, 250, 300, 400, 500, 750 or 1000 successive nucleotides with one of the nucleic acid sequences selected from the group consisting of (i) a nucleic acid sequence with one of the SEQ ID NOs: 27, (ii) a nucleic acid sequence which is complementary to a sequence from i), (iii) a nucleic acid sequence which has at least 80%, 85%, 90% or 95% or preferably at least 96%, 97%, 98%, or 99% identity with a sequence from (i) or (ii), (iv) a nucleic acid sequence which differs from a nucleic acid sequence according to (i), (ii) or (iii) in accordance with the degeneracy of the genetic code, (v) a nucleic acid sequence which hybridizes with a nucleic acid sequence according to (i), (ii) or (iii) under stringent conditions, (vi) a nucleic acid sequence which codes for a protein with one of the SEQ ID NOs: 28 or a homologue, analogue or orthologue thereof, or vii) a nucleic acid sequence in antisense orientation to a nucleic acid sequence according to (i) to (vi).

In a further aspect, the present invention concerns a vector which comprises the nucleic acid in accordance with the invention or the expression cassette in accordance with the invention. The vector may be a plasmid, a cosmid, a phage or an expression vector, a transformation vector, a shuttle vector or a cloning vector; it may be double or single-stranded, linear or circular, or it can transform a prokaryotic or eukaryotic host either by integration into its genome or extra-chromosomally. Preferably, the nucleic acid or expression cassette in accordance with the invention is operatively connected with one or more regulatory sequences which allow transcription and optionally expression in a prokaryotic or eukaryotic host cell. A regulatory sequence, preferably DNA, may be homologous or heterologous to the nucleic acid in accordance with the invention. As an example, the nucleic acid may be under the control of a suitable promoter or a terminator. Suitable promoters may be promoters which are constitutively induced (e.g.: 35S promoter from the "Cauliflower mosaic virus" (Odell et al. 1985); particularly suitable promoters are those of the type which are tissue-specific or stress-specific (e.g. chill-responsive, BN115 (U.S. Pat. No. 5,847,102 A)) or development-specific (e.g.: flower-specific promoters, for example the promoter region of the gene GTCHS1; Kobayashi, H et al. Flower-specific gene expression directed by the promoter of a chalcone synthase gene from Gentiana triflora in Petunia hybrida. Plant Science, 1998, 131. Jg., No. 2, p. 173-180). Synthetic or chimeric promoters which are not from nature and which are composed of several elements and contain a minimal promoter as well as, upstream of the minimal promoter, at least one cis-regulatory element which acts as a binding site for special transcription factors may also be suitable promoters. Chimeric promoters can be tailored to the desired specificities and are induced or repressed by various factors. Examples of such promoters can be found in Gun & Rushton (Gurr, S J; Rushton, P J. Engineering plants with increased disease resistance: what are we going to express?. TRENDS in Biotechnology, 2005, 23. Jg., No. 6, p. 275-282) or Venter (Synthetic promoters: genetic control through cis engineering. Trends in Plant Science, 2007, 12. Jg., No. 3, p. 118-124). An example of a suitable terminator is the nos-terminator (Depicker, A, Stachel, S, Dhaese, P, Zambryski, P and Goodman, H (1982) J. Mol. Appl. Genet., 1, 561-575).

In addition to the vectors described above, the present invention also provides a method comprising introducing a vector as described into a host cell. The vector may, for example, be introduced by conjugation, mobilization, biolistic transformation, *agrobacterium*-mediated transformation, transfection, transduction, vacuum infiltration or electroporation. Methods of this type as well as methods for the preparation of the described vectors are familiar to the person skilled in the art (Sambrook et al. 2001, Molecular cloning: A laboratory manual (3-volume set) (Vol. 999). Cold Spring Harbor, N.Y.: Cold Spring Harbor Laboratory Press).

In a further aspect, the present invention concerns a host cell which comprises the nucleic acid, the expression cassette or the vector of the present invention. A "host cell" in the context of the invention may be a prokaryotic (for example bacterial) or eukaryotic cell (for example a plant cell or a yeast cell). Preferably, the host cell is an *agrobacterium* such as *Agrobacterium tumefaciens* or *Agrobacterium rhizogenes*, or a plant cell which comprises the nucleic acid, the expression cassette or the vector of the present invention. The person skilled in the art will be aware both of many methods such as conjugation or electroporation with which the nucleic acid, the expression cassette or the vector of the present invention can be introduced into an *agrobacterium*, as well as of methods such as various transformation processes (biolistic transformation, *agrobacterium*-mediated transformation) with which the nucleic acid, the expression cassette or the vector of the present invention can be introduced into a plant cell (Sambrook et al. 2001).

In a further aspect, the present invention concerns a transgenic plant cell which comprises the nucleic acid in accordance with the invention as a transgene or the expression cassette or the vector of the present invention, and a transgenic plant or a portion thereof which comprises the transgenic plant cell. An example of a transgenic plant cell or plant of this type is a plant cell or plant which is transformed with the nucleic acid in accordance with the invention, with the expression cassette or with the vector of the present invention, preferably stably. A transgenic plant or cell of the present invention preferably comprises a freshly-conferred chill tolerance or an increased chill tolerance compared with a wild type plant which is isogenic, but which has not been transformed with the nucleic acid in accordance with the invention, with the expression cassette or with the vector of the present invention, preferably stably.

In a preferred embodiment of the transgenic plant, the nucleic acid is operatively connected with one or more regulatory sequences which enable transcription and optionally expression in the plant cell. A regulatory sequence, preferably DNA, can be homologous or heterologous to the nucleic acid in accordance with the invention. The total construct formed by the nucleic acid in accordance with the invention and the regulatory sequence(s) can constitute the transgene in the form of the expression cassette. A "portion of a plant" may be a fertilized or unfertilized seed, an embryo, pollen, tissue, an organ or a plant cell, wherein the fertilized or unfertilized seed, embryo or pollen are produced on the transgenic plant wherein the nucleic acid in accordance with the invention has been integrated into its genome as a transgene or the expression cassette or the vector. Similarly, the present invention also includes a descendant of the transgenic plant into the genome of which the nucleic acid in accordance with the invention has been integrated as a transgene, the expression cassette or the vector and which has a conferred chill tolerance or an increased chill tolerance compared with a wild type plant, which is isogenic, but which has not been transformed with the nucleic acid in accordance with the invention, with the expression cassette or with the vector of the present invention, preferably stably.

A freshly-conferred or increased chill tolerance may be determined in a species-specific and experimental manner. In this regard, a leaf image analysis method may be appropriate, which method essentially comprises the following steps: a) two to four weeks cultivation of the plants under zero-stress conditions as regards the outside temperature, b) exposing the plants to a significant chill stress over a period of at least one week, c) carrying out a regeneration phase again under zero-stress conditions over a period of at least one week, and d) measuring the leaf green colour loss in one or more leaves which grew during the period during which the chill stress was applied. As an example, this is described below for maize (*Zea mays*): the plants are cultivated for two weeks under optimal conditions (no stress) in a greenhouse at 25° C. (daytime temperature) or 22° C. (night time temperature). Next, they are transferred to a climatic chamber at 8° C. or 6° C. for one week. This is followed by a one-week regeneration phase in the greenhouse at 25° C. or 22° C. Next, preferably, the 4th or 5th leaf is examined as regards its colour. This produces a value of 100% for complete maintenance of the green leaf colour and a value of 0% for complete yellowing (chlorosis). In the context of the present invention, it has been shown that the TH variant did better than the SL variant in maintaining chlorophyll under chill stress (see Table 5). In total, values of 10% to 85% leaf greening were measured. The leaf green colour loss of the TH variant was reduced by 19% to 75% compared with the SL variant, i.e. the chill tolerance increased significantly. In this regard, the term "chill tolerance" means— but is not limited to—a reduction in the loss of green leaf colour under chill stress of 5%, 10%, 15%, 20%, preferably 30%, 40% or 50%, particularly preferably 60%, 70%, 80% or 90% measured using the leaf image analysis described above.

Alternatively, the freshly-conferred or increased chill tolerance in a plant may also be measured by measuring the plant height at the time of onset of the elongation growth in the shoot region. To this end, chill-tolerant and sensitive plants are cultivated under chill stress conditions in comparative tests. In the context of the present invention, it was thus shown that, for example, the TH variant maize had an approximately 35% increased plant length, which in absolute terms is approximately an additional 21 cm compared with the sensitive S1 variant. In this manner, the term "chill tolerance" may also mean that a plant with freshly-conferred or increased chill tolerance has a plant height which is increased by at least 5%, 10%, 15%, 20%, 25%, 30% or 35% compared with a control plant at the time of onset of elongation growth.

In a further aspect, the invention provides a method for the production of a chill-tolerant plant. A method of this type comprises the following steps: A) mutagenization of plant cells or of portions of a plant and subsequent regeneration of plants from the mutagenized plant cells or mutagenized parts, or mutagenization of plants, and B) identification of a plant from A) which, in an endogenous DNA sequence which is identical to a nucleic acid sequence selected from the group consisting of (i) a nucleic acid sequence with one of the SEQ ID NOs: 27, 17, 19, 5, 7, 23 or 25, (ii) a nucleic acid sequence which is complementary to a sequence from i), (iii) a nucleic acid sequence which has at least 80%, 85%, 90% or 95% or preferably at least 96%, 97%, 98%, or 99% identity with a sequence from (i) or (ii), (iv) a nucleic acid sequence which differs from a nucleic acid sequence according to (i), (ii) or (iii) in accordance with the degeneracy of the genetic code, (v) a nucleic acid sequence which hybridizes with a nucleic acid sequence according to (i), (ii) or (iii) under stringent conditions, or (vi) a nucleic acid sequence which codes for a protein with one of the SEQ ID NOs: 28, 18, 20, 6, 8, 24 or 26, or a homologue, analogue or orthologue thereof, or in a regulatory sequence of the endogenous DNA sequence, has at least one mutation which causes an alteration in the transcription or expression rate or level of transcription or expression of the endogenous DNA sequence in the identified plant compared with a non-mutagenized wild type plant or an alteration in the activity or stability of a protein or polypeptide coded by the endogenous DNA sequence in the identified plant compared with a non-mutagenized wild type plant. Preferably, the at least one mutation ensures that the identified plant becomes chill-tolerant or that an already existing chill tolerance is increased.

Preferably, the endogenous DNA sequence from step B) codes for an auxin-responsive protein or a SAUR protein, particular preferably for the protein SAUR31 with SEQ ID NOs: 28 or 30 or a homologue, analogue or orthologue thereof. Preferably, the regulatory sequence of the endogenous DNA sequence from step B) is a promoter or a portion thereof. Particularly preferably, the promoter is a promoter with SEQ ID NO: 34 or a promoter which has an identity of at least 80%, 85% or 90%, preferably of at least 92%, 94%, 96% or 98% or particularly preferably of at least 98.5%, 99%, 99.5% or 99.8% with the promoter with SEQ ID NO: 34. An example of a potentially mutated form of a regulatory sequence of an endogenous DNA sequence is the promoter with SEQ ID NO: 33.

A mutation means a modification on a DNA level, i.e. a change in the genetics and/or the epigenetics. As an example, a change in the genetics may be an exchange of at least one nucleobase in the endogenous DNA sequence or in a regulatory sequence of the endogenous DNA sequence. If such a nucleobase exchange occurs, for example in a promoter, then this may result in a modified activity of the promoter, because, for example, cis-regulatory elements are modified by this in a manner such that the affinity of a transcription factor to the mutated cis-regulatory elements is altered compared with the wild type promoter, so that the activity of the promoter with the mutated cis-regulatory elements is raised or reduced, depending on whether the transcription factor is a repressor or inductor or whether the affinity of the transcription factor to the mutated cis regulatory element is strengthened or weakened. If such a nucleobase exchange takes place in a coding region for the endogenous DNA sequence, for example, then this may lead to an amino acid exchange in the coded protein, which can change the activity or stability of the protein compared with the wild type protein. A further example of an alteration in the genetics is the deletion of nucleotides in the regulatory sequence and/or the endogenous DNA sequence as well as the addition of nucleotides in the regulatory sequence and/or the endogenous DNA sequence. An example of the regulation of genes by insertion of nucleotides by transposon mutagenesis in maize is shown in Das & Martienssen (Das, Lekha, and Robert Martienssen. "Site-selected transposon mutagenesis at the hcf106 locus in maize" The Plant Cell 7.3 (1995): 287-294.). An alteration in the epigenetics may, for example, be caused by an altered methylation pattern in the DNA.

The person skilled in the art will be aware that a "mutation" within the meaning of the invention can be obtained by a process of mutagenization in step A) of the method for the production of a chill-tolerant plant. The mutagenization here includes both conventional mutagenesis and also location-specific mutagenesis, also known as "genome editing". In conventional mutagenesis, the modification on a DNA level is not carried out specifically. The plant cell or the plant is exposed to mutagenic conditions such as, for example TILLING, by UV light irradiation or the use of chemicals (Till, Bradley J., et al. "Discovery of induced point mutations in maize genes by TILLING." BMC Plant Biology 4.1 (2004): 12.). A further method for random mutagenesis is mutagenesis with the aid of a transposon. A comprehensive collection of mutants is freely available from the UniformMU project. The collection and the methods are described in McCarty et al. (McCarty, Donald R., et al. "Steady-state transposon mutagenesis in inbred maize" The Plant Journal 44.1 (2005): 52-61.). Location-specific mutagenesis allows the introduction of modifications on a DNA level to be made specifically at predetermined sites in the DNA. In this regard, for example, TALENS (WO 2010/079430, WO 2011/072246), meganucleases (Silva, George, et al. "Meganucleases and other tools for targeted genome engineering: perspectives and challenges for gene therapy." Current gene therapy 11.1 (2011): 11.), homing endonucleases (Stoddard, Barry L. "Homing endonucleases: from microbial genetic invaders to reagents for targeted DNA modification." Structure 19.1 (2011): 7-15.), zinc-finger nucleases (Lloyd, Alan, et al. "Targeted mutagenesis using zinc-finger nucleases in *Arabidopsis*." Proceedings of the National Academy of Sciences of the United States of America 102.6 (2005): 2232-2237) or a CRISPR/Cas system (Gaj, Thomas, Charles A. Gersbach, and Carlos F. Barbas. "ZFN, TALEN, and CRISPR/Cas-based methods for genome engineering." Trends in biotechnology 31.7 (2013): 397-405) may be used. Preferably, the mutations occur in all copies or alleles or, where appropriate, in all homologues of the corresponding endogenous DNA sequences. This typically means two alterations in respect of a diploid organism such *Zea may*, for example.

The identification of a plant in step B) may, for example, be carried out with the aid of molecular markers or probes. DNA probes are, for example, primers or primer pairs which may be used in a PCR reaction. As an example, TILLING mutants may be detected or identified by sequencing the target gene in a TILLING population or other methods which detect mispairing in DNA such as, for example, melting point analyses or the use of mispairing-specific nucleases. The present invention encompasses in this respect primer/primer pairs which can be used in this regard, such as primers for the detection of SAUR31 or a mutated form of the promoter of SAUR31, Furthermore, mutants produced using transposons, by using transposon-specific primers and target gene-specific primers in PCR over the whole population and subsequent sequencing of PCR products may be detected. Primers of this type are also encompassed by the invention, Altering the expression rate or level of expression may, for example, be determined using RT-PCR in plant tissue; the alteration in stability, for example, by investigating ubiquitin binder sites and prediction via alterations in the tertiary structure. Furthermore, recombinant expression of the wild type protein and the corresponding mutated proteins and subsequent biochemical activity tests are also suitable. The person skilled in the art will be aware of other agents and methods in the prior art which could be used for the identification of a plant or plant cell in step B).

The present invention also concerns molecular markers which detect the presence or absence of a mutation in the endogenous DNA sequence or in a regulatory sequence of the endogenous DNA sequence. Markers of this type are based, for example, on a SNP and are specific for the mutation (examples: KASPar or TaqMan Marker).

The present invention furthermore concerns a plant which can be produced or has been produced using the present method, or a portion of said plant, wherein a portion of the plant may be a fertilized or non-fertilized seed, an embryo, pollen, a tissue, an organ or a plant cell, and which has at least one mutation in its genome. Similarly, the present invention also encompasses a descendant of the plant which comprises the at least one mutation and is chill-tolerant.

Furthermore, the present invention also concerns a method for isolating a nucleic acid which confers or increases chill tolerance in a plant or plant cell, comprising the following steps:

A) producing a plant in accordance with the method described above or providing a plant or a cell of a plant which has been produced using the method described above or can be produced thereby, and B) isolating a nucleic acid which comprises the endogenous DNA sequence with the at least one mutation from the genome of the plant or cell from A). Isolation of the nucleic acid in step B) may be carried out by CTAB extraction or on DNA-binding columns, detection of the mutation via sequencing or molecular markers such as SNP-based KASPar or TaqMan markers, or in the case of insertion or deletion mutants via markers based on length polymorphisms.

The present invention also encompasses a nucleic acid which has been obtained by the method described above for isolation or which is obtainable by the method described above for isolation, as well as an expression cassette or a vector which comprises the isolated nucleic acid.

In a further aspect, the present invention provides a method for the production of a transgenic chill-tolerant plant. The method may comprise the following steps: A) providing the nucleic acid or expression cassette described above, or providing the vector described above, B) transformation, preferably stable transformation, of at least one plant cell by introduction of the nucleic acid, the expression cassette or the vector from A), C) regenerating transgenic plants from the at least one transformed plant cell from B), and D) identifying a transgenic, chill-tolerant plant from C). The method for the production of the transgenic chill-tolerant plant also includes the provision of two or more of the nucleic acids described above, optionally also different embodiments of the nucleic acid in accordance with the invention and optionally in one or more expression cassettes or vectors, and the transformation of plant cells by introducing the two or more nucleic acids. Finally, in addition to the nucleic acid in accordance with the invention, one or more other nucleic acids, which in known manner may be used to mediate or increase chill tolerance, may be used as a transgene (for example WO 2002/048378 A2, WO 2008/148298 A1).

In a preferred embodiment of the production method, a plant identified in D) preferably has an altered expression pattern compared with a wild type plant which, for example, was regenerated from an isogenic, non-transformed plant cell, characterized in that, because of post-transcriptional gene silencing, the expression rate or expression level of an endogenous DNA sequence with a nucleic acid sequence selected from the group consisting of (i) a nucleic acid sequence with one of the SEQ ID NOs: 27, 17, 19, 5, 7, 23 or 25, (ii) a nucleic acid sequence which is complementary to a sequence from i), (iii) a nucleic acid sequence which has at least 80%, 85%, 90% or 95% or preferably at least 96%, 97%, 98%, or 99% identity with a sequence from (i) or (ii), (iv) a nucleic acid sequence which differs from a nucleic acid sequence according to (i), (ii) or (iii) in accordance with the degeneracy of the genetic code, (v) a nucleic acid sequence which hybridizes with a nucleic acid sequence according to (i), (ii) or (iii) under stringent conditions, or (vi) a nucleic acid sequence which codes for a protein with one of the SEQ ID NOs: 28, 18, 20, 6, 8, 24 or 26, or a homologue, analogue or orthologue thereof, is reduced.

The present invention also concerns a transgenic chill-tolerant plant which can be produced using the said method or is produced using it, or a portion of said plant, wherein a portion of a plant may be a fertilized or unfertilized seed, an embryo, pollen, tissue, an organ or a plant cell, wherein the fertilized or unfertilized seed, embryo or pollen are produced on the transgenic plant and into the genome of which the nucleic acid in accordance with the invention has been integrated as a transgene, expression cassette or vector. Similarly, the present invention also encompasses a descendant of the transgenic plant which is chill-tolerant.

In a further aspect, the present invention concerns a method for conferring or increasing chill tolerance in a plant cell or a plant. A method of this type may comprise the following steps: A) transformation, preferably stable transformation, preferably of at least one plant cell by introducing the nucleic acid in accordance with the invention described above or expression cassette of the present invention, or the vector of the present invention described above, optionally B) regenerating transgenic plants from the at least one transformed plant cell from A). The method for the production of the transgenic chill-tolerant plant also encompasses the transformation of two or more of the nucleic acids in accordance with the invention described above, optionally also different embodiments of the nucleic acids in accordance with the invention and optionally one or more of the expression cassettes or vectors of the present invention. In a preferred embodiment of the method, the transformation in step A) results in a plant cell or plant which, compared with a wild type plant cell which, for example is an isogenic, non-transformed plant cell, or is a plant which, for example, has been regenerated from an isogenic non transformed plant cell, preferably has an altered expression pattern, characterized in that, because of post-transcriptional gene silencing, the expression rate or expression level of an endogenous DNA sequence with a nucleic acid sequence selected from the group consisting of (i) a nucleic acid sequence with one of the SEQ ID NOs: 27, 17, 19, 5, 7, 23 or 25, (ii) a nucleic acid sequence which is complementary to a sequence from i), (iii) a nucleic acid sequence which has at least 80%, 85%, 90% or 95% or preferably at least 96%, 97%, 98%, or 99% identity with a sequence from (i) or (ii), (iv) a nucleic acid sequence which differs from a nucleic acid sequence according to (i), (ii) or (iii) in accordance with the degeneracy of the genetic code, (v) a nucleic acid sequence which hybridizes with a nucleic acid sequence according to (i), (ii) or (iii) under stringent conditions, or (vi) a nucleic acid sequence which codes for a protein with one of the SEQ ID NOs: 28, 18, 20, 6, 8, 24 or 26, or a homologue, analogue or orthologue thereof, is reduced.

Furthermore, in an alternative aspect, the invention also concerns the use of the nucleic acid in accordance with the invention, the expression cassette or the vector of the present invention in a method for the production of a transgenic chill-tolerant plant cell or plant or in a method for conferring or increasing the chill tolerance in a plant cell or plant.

In a further aspect, the present invention concerns an agent for external application to plants. This agent is provided for external application to plants. It contains double stranded RNA, wherein a strand of this RNA contains a nucleic acid sequence which matches over at least 19, 20, 21, 22, 23, 24 or 25, preferably at least 30, 32, 34, 36, 38 or 40, particularly preferably at least 50, 60, 70, 80, 90 or 100, or more particularly preferably at least 150, 200, 250, 300, 400, 500, 750 or 1000 successive nucleotides with one of the nucleic acid sequences selected from the group consisting of (i) a nucleic acid sequence with one of the SEQ ID NOs: 27, 17, 19, 5, 7, 23 or 25, (ii) a nucleic acid sequence which is complementary to a sequence from i), (iii) a nucleic acid sequence which has at least 80%, 85%, 90% or 95% or preferably at least 96%, 97%, 98%, or 99% identity with a sequence from (i) or (ii), (iv) a nucleic acid sequence which differs from a nucleic acid sequence according to (i), (ii) or (iii) in accordance with the degeneracy of the genetic code, (v) a nucleic acid sequence which hybridizes with a nucleic acid sequence according to (i), (ii) or (iii) under stringent conditions, (vi) a nucleic acid sequence which codes for a protein with one of the SEQ ID NOs: 28, 18, 20, 6, 8, 24 or 26, or a homologue, analogue or orthologue thereof, or vii) a nucleic acid sequence in antisense orientation to a nucleic acid sequence according to (i) to (vi). Double stranded RNA for the production of the agent in accordance with the invention can be produced by in vitro methods which are known to the person skilled in the art. As an example, synthesis of the double stranded RNA may be carried out synthetically, wherein the RNA is formed directly in vitro. The double stranded RNA may also be synthesized from a double stranded DNA via the formation of a mRNA transcript which then, for example, forms a hairpin structure.

The agent in accordance with the invention may be used as an admixture in a seed casing or in early development by spraying in the form of a spray. Furthermore, the agent may also be used by mixing with the growing substrate before or after emergence of the plants. In each case, the agent is suitable for conferring or increasing chill tolerance in a cell of the seed or plant or the seed or the plant. When used to pre-treat seed, the agent may initially be bound into a carrier substance and be applied in a combination which comprises the double stranded RNA and the carrier substance onto the seeds, wherein the carrier substance may, for example, have a RNA-stabilizing action. Examples of RNA stabilizers which may be used are liposomes, which encapsulate the RNA molecule.

Furthermore, the present invention also encompasses a method for conferring or increasing chill tolerance in a plant cell or a plant, which comprises the step of external application of the agent in accordance with the invention. Preferably, the agent is mixed in with the seed material sheath or the seed film or is sprayed directly onto the seed material or the plant. The present invention also concerns the use of the agent in accordance with the invention for conferring or increasing chill tolerance in a plant cell or a plant.

In a further aspect, the present invention concerns a chill-tolerant maize plant or a portion thereof, comprising a first chromosomal interval from a donor on chromosome 4 between the marker positions ma59778s31 and ma59778119, which comprises a chill tolerance-conferring nucleic acid, preferably an endogenous chill tolerance-conferring nucleic acid, and in a region on chromosome 4 flanked by the marker positions ma59778119 and ma20205s01, it comprises at least one further chromosomal interval from the same donor as the first chromosomal interval and at least one chromosomal interval which does not originate from the donor, wherein the chill tolerance-conferring nucleic acid comprises one or more nucleic acid sequences selected from the group consisting of a) a nucleic acid sequence with one of the SEQ ID NOs: 29, 3, 7, 11, 15, 25 or 35, b) a nucleic acid sequence which has at least 98%, 99% or 99.5% identity with a sequence from a) or b), c) a nucleic acid sequence which differs from a nucleic acid sequence according to a) in accordance with the degeneracy of the genetic code, d) a nucleic acid sequence which codes for a protein with one of the SEQ ID NOs: 30, 4, 8, 12, 16 or 26 or a homologue, analogue or orthologue thereof. In a preferred exemplary embodiment, the chromosomal interval on chromosome 4, which comprises a chill tolerance-conferring nucleic acid, is an interval between the marker positions ma59778s32 and ma59778119 and/or the chill tolerance-conferring nucleic acid comprises a nucleic acid sequence selected from the group consisting of a) a nucleic acid sequence with SEQ ID NO: 29, b) a nucleic acid sequence which has at least 98%, 99% or 99.5% identity with a sequence from a), c) a nucleic acid sequence which differs from a nucleic acid sequence according to a) in accordance with the degeneracy of the genetic code, or d) a nucleic acid sequence which codes for a protein with SEQ ID NO 30 or a homologue, analogue or orthologue thereof; preferably, the nucleic acid sequence is operatively connected with a promoter which comprises the nucleotide sequence with SEQ ID NO: 33, or with an allele variant or a modified form of a promoter which comprises the nucleotide sequence with SEQ ID NO: 34, wherein the allele variant or the modified form has a comparable expression rate or level of expression to the promoter which comprises the nucleotide sequence with SEQ ID NO: 33. An "allele variant" or a "modified form of the promoter" means a promoter which has an expression rate or expression level which is reduced by more than 5%, 10%, 15%, 20%, 25%, 30%, 40% or 50% compared with the expression rate or expression level produced by the promoter which comprises the nucleotide sequence with SEQ ID NO: 34. A "comparable expression rate or expression level" means that the allele variant or the modified form of the promoter which comprises the nucleotide sequence with SEQ ID NO: 34, which essentially has an expression rate or expression level which differs by no more than 20%, 18%, 16%, 14% or 12%, preferably by no more than 10%, 9%, 8%, 7% or 6%, or particularly preferably no more than 5%, 4%, 3%, 2%, 1%, 0.5% or 0% from the expression rate or expression level of the promoter which comprises the nucleotide sequence with SEQ ID NO: 33.

Furthermore, the presence of the at least one chromosomal interval which does not originate from the donor in the region on chromosome 4 flanked by the marker positions ma59778119 and ma20205s01 means that, for example, because of one or more recombination events in the crossing process with a maize plant which does not carry the donor interval, a corresponding donor interval or corresponding donor intervals is replaced by the at least one chromosomal interval which does not originate from the donor. In other words, the chromosomal interval flanked by the marker positions ma59778119 and ma20205s01 which originates from the donor is present in the donor allele in a truncated form.

Alternatively, modern biotechnology provides the person skilled in the art with a variety of other tools which can be used to carry out precise genome engineering: genetic engineering strategies by means of which specific donor segments can be replaced by non-donor segments, and so a "selective sweep" in a plant genome can be reduced or eliminated, including the use of TALE nucleases (TALENs) or zinc-finger nucleases (ZFNs) as well as CRISPR/Cas systems which, inter alia, have been described in the German patent application DE 10 2013 014 637 for the elimination of linkage drag-carrying nucleotide sequences from the genome of *Helminthosporium turcicum* resistant (hybrid) maize; see DE 10 2013 014 637 on pages 13 and 14 in paragraphs [0038] to [0042] and the references cited therein. These techniques, which are also described in international patent application WO 2014/104878, may be used in an equivalent manner in the production of the present plants in accordance with the invention.

Furthermore, the present invention also encompasses a combination of the conventional breeding technique and modern biotechnology. Thus, for example, with the aid of this novel genome editing recombination strategy, "hot spots" can be produced in a plant which occur at suitable sites in order to directly promote the exchange of donor segments in the region on chromosome 4 flanked by the marker positions ma59778119 and ma20205s01 by non-donor segments. The present invention makes available to the person skilled in the art in this regard the necessary information regarding the localization of the "selective sweep" as well as the position of the chill tolerance-conferring nucleic acid(s).

In a preferred exemplary embodiment, the plant in the region on chromosome 4 flanked by the marker positions ma59778119 and ma20205s01, it comprises at least one further chromosomal interval from the same donor and at least one chromosomal interval which does not originate from the donor, wherein the at least one further chromosomal interval from the same donor constitutes less than 90%, less than 80%, less than 70%, preferably less than 60%, less than 50%, less than 40%, or particularly preferably less than 30%, less than 20%, less than 10%, less than 5%, less than 2% or less than 1% of the region on chromosome 4 flanked by the marker positions ma59778119 and ma20205s01, or wherein the at least one chromosomal interval which does not originate from the donor constitutes more than 5%, more than 10%, more than 20%, more than 30%, preferably more than 40%, more than 50%, more than 60%, or particularly preferably more than 70%, more than 80%, more than 90%, more than 95%, more than 98% or more than 99% of the region on chromosome 4 flanked by the marker positions ma59778119 and ma20205s01.

In a preferred exemplary embodiment, in the region on chromosome 4 flanked by the marker positions ma59778119 and ma20205s01, the plant comprises at least one further chromosomal interval from the same donor and at least one chromosomal interval which does not originate from the donor, wherein the at least one further chromosomal interval from the same donor constitutes less than 100 Mb, less than 90 Mb, less than 80 Mb, preferably less than 70 Mb, less than 60 Mb, less than 50 Mb, or particularly preferably less than 40 Mb, less than 30 Mb, less than 20 Mb, less than 15 Mb, less than 10 Mb or less than 5 Mb of the region on chromosome 4 flanked by the marker positions ma59778119 and ma20205s01, or wherein the at least one chromosomal interval which does not originate from the donor constitutes more than 5 Mb, more than 10 Mb, more than 15 Mb, more than 20 Mb, preferably more than 30 Mb, more than 40 Mb, more than 50 Mb, or particularly preferably more than 60 Mb, more than 70 Mb, more than 80 Mb, more than 90 Mb or more than 100 Mb of the region on chromosome 4 flanked by the marker positions ma59778119 and ma20205s01.

In a particularly preferred exemplary embodiment, in the region on chromosome 4 flanked by the marker positions ma59778119 and ma20205s01, the plant comprises a chromosomal interval from the same donor from marker position ma59778119 to ma52594s01 and a chromosomal interval which does not originate from the donor, from ma52594s01 to ma20205s01 auf.

In a further preferred embodiment, the region on chromosome 4 flanked by the marker positions ma59778119 and ma20205s01 is either alternatively or additionally also characterized in that it comprises a higher allele frequency, at least in parts.

Preferably, the chromosomal interval between the marker positions ma59778s31 and ma59778119 and the chromosomal interval between the marker positions ma59778119 and ma20205s01 is localized on chromosome 4 in the maize genome. The chromosomal interval between the marker positions ma59778119 and ma20205s01 may contain the centromer of chromosome 4.

In a preferred example, the chromosomal interval which comprises a chill tolerance-conferring nucleic acid is a chromosomal interval between the marker positions ma59778s32 and ma59778119. In a further preferred exemplary embodiment, the chromosomal interval between the marker positions ma59778s31 and ma59778119 comprises a chromosomal interval flanked by marker positions ma59778s32 and ma59778119

Preferably, the chromosomal interval between the marker positions ma59778s31 and ma59778119 as well as the chill tolerance-conferring nucleic acid contained therein originates from a maize line of the Dent pool or is characteristic of a Dent pool, i.e. the person skilled in the art is able to identify the chromosomal interval as originating unequivocally from the Dent pool, for example with the aid of molecular markers.

Figure 5:
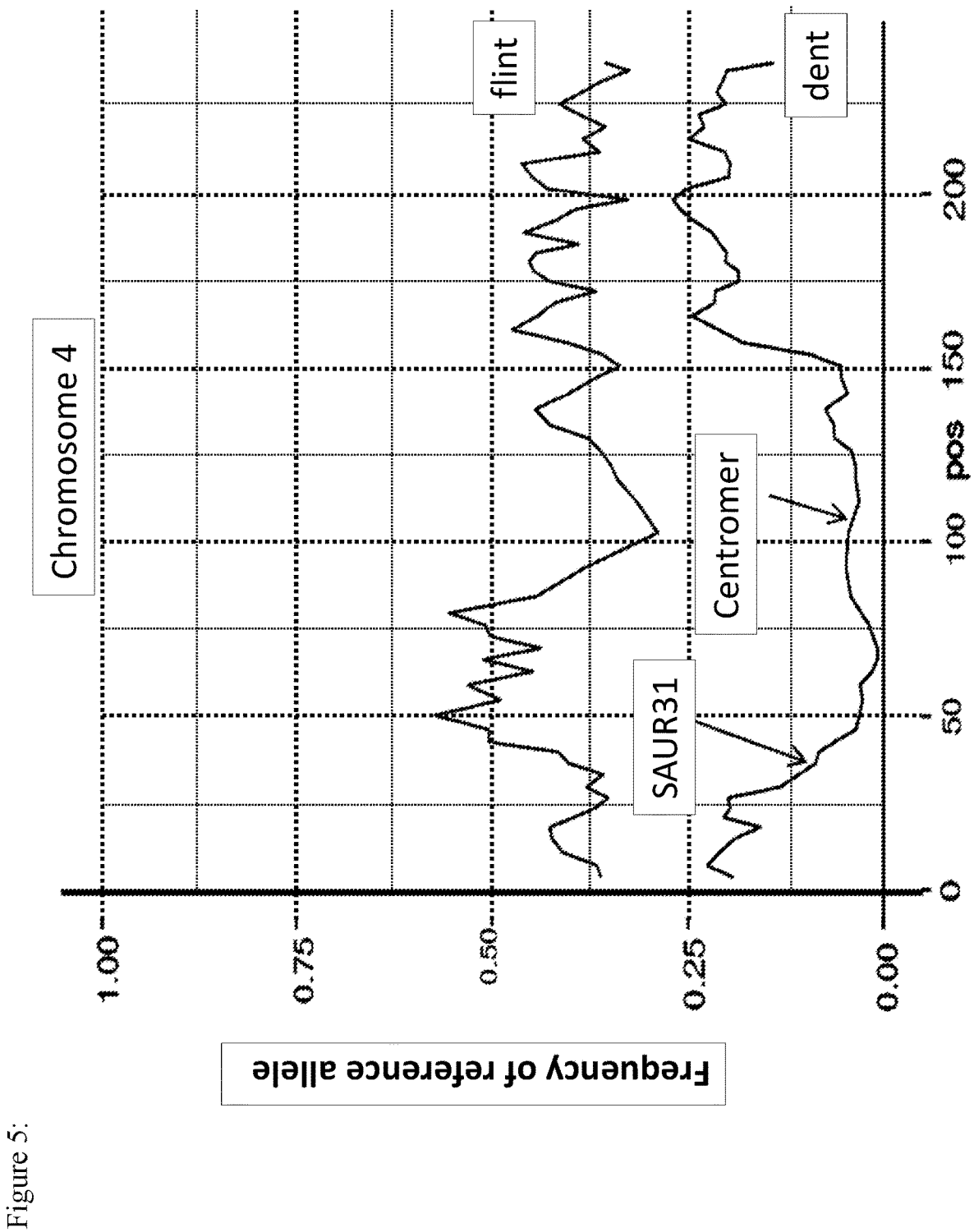

A selection on genes with strong effects or chromosomal intervals containing a gene with a strong effect such as, for example, in the genome interval in accordance with the invention or chill tolerance-conferring QTL (in particular the identified gene SAUR31) results in an alteration in the allele frequencies. Depending on the degree of recombination and the selection intensity, this alteration in the allele frequencies not only affects the gene or the region bordering the interval, but also neighbouring chromosome regions. This could result in a limited genetic diversity, which is known as "selective sweep". For a person skilled in the art in the area of plant breeding, this "selective sweep" is extraordinarily disadvantageous, because the plant material which is produced in further breeding operations can no longer achieve its original potential. The genetic depletion means that the conventional strategy of breeding from fresh recombinations and selections comes to nothing. This is illustrated in FIG. 5. The figure shows a substantially reduced genetic diversity in the Dent gene pool compared with the Flint gene pool in the region of chill tolerance-conferring QTL comprising, for example, the gene SAUR31. All of the ORFs of the QTLs found here and the corresponding genes originate from the Dent gene pool. Uncontrolled crossing of the chill tolerance-conferring QTL in another genetic background (for example the Flint pool) would even in this pool lead to a drastic reduction in allele frequencies. In the context of the invention, clearly, crossing of the chromosomal interval between the marker positions ma59778s31 and ma59778119, which comprises a chill tolerance-conferring nucleic acid, without adequate countermeasures would result in each case in a substantial deterioration in the allele frequency on chromosome 4. The transfer of the identified QTLs or the identified chill tolerance-conferring nucleic acid without a reduction in the diversity of the breeding material constitutes an enormous challenge and was finally accomplished by means of very complicated marker-supported fine mapping of the region. In this connection, the identification of single nucleotide polymorphisms (SNPs; consequence of SNPs=haplotype) in the chromosomal interval and the adjacent regions was also necessary. By identifying the TH haplotypes equipped with increased chill tolerance and developing novel markers, however, in accordance with the invention, it was surprisingly possible, by using newly-developed molecular markers for a marker-supported selection, to cross the corresponding chromosomal interval in accordance with the invention described above with the chill tolerance-conferring nucleic acid within a substantially limited interval. The plants produced in this manner exhibited an increased chill tolerance simultaneously with a largely retained genetic diversity. From known breeding lines such as B73, for example, this produces a solution to the problem of selective sweep on the basis of the variable structure of the region.

An allele frequency which is increased "at least in parts" means, for example, that the region on chromosome 4 flanked by the marker positions ma59778119 and ma20205s01 has an increased allele frequency in a region of at least 5 megabases (Mb), at least 10 Mb, at least 15 Mb, at least 20 Mb or at least 25 Mb, preferably at least 30 Mb, at least 40 Mb, at least 50 Mb or at least 60 Mb, or particularly preferably at least 70 Mb, at least 80 Mb, at least 90 Mb or at least 100 Mb. Furthermore, an allele frequency which is increased "at least in parts" can mean that the region on chromosome 4 flanked by the marker positions ma59778119 and ma20205s01 preferably has an increased allele frequency of at least 1 Mb, at least 2 Mb, at least 3 Mb, at least 4 Mb or at least 5 Mb, preferably at least 10 Mb, at least 15 Mb, at least 20 Mb or at least 25 Mb, or particularly preferably at least 30 Mb, at least 35 Mb, at least 40 Mb or at least 50 Mb on either side of the centromer, preferably of chromosome 4.

An "increased allele frequency" means, for example, a deviation from the allele frequency of 0.5 by no more than 0.4, 0.375 or 0.35, preferably no more than 0.325, 0.3 or 0.275, or particularly preferably no more than 0.25. Furthermore, an "increased allele frequency" can also mean that the allele frequency is not smaller than 0.1, 0.125 or 0.15, preferably not smaller than 0.175, 0.2 or 0.225, or particularly preferably not smaller than 0.25. Furthermore, an "increased allele frequency" can also mean that at least 10%, 15% or 20%, preferably 25%, 30% or 40% or particularly preferably 45% or 50% of a chromosomal interval originates from the Flint pool. In contrast, a "low allele frequency" means a deviation from the allele frequency of 0.5 by more than 0.4 or 0.425. Furthermore, a "low allele frequency" can also mean that the allele frequency is less than 0.1 or 0.075. Furthermore, a "low allele frequency" can also mean that less than 5%, 6%, 7%, 8%, 9% or 10% of a chromosomal interval originates from the Flint pool. In the context of the present invention, an "increased allele frequency" can also mean that the chromosomal interval, which the increased allele frequency exhibits is truncated or shortened, preferably proximally or distally to the chill tolerance-conferring nucleic acid, for example by at least 5 megabases (Mb), at least 10 Mb, at least 15 Mb, at least 20 Mb or at least 25 Mb, preferably at least 30 Mb, at least 40 Mb, at least 50 Mb or at least 60 Mb, or particularly preferably at least 70 Mb, at least 80 Mb, at least 90 Mb or at least 100 Mb.

In a further aspect, the present invention encompasses molecular markers which are capable, in a chromosomal interval flanked by the marker positions ma59778s31 and ma20205s01 or by the marker positions ma59778s31 and ma52594s01 or by the marker positions ma59778s31 and ma59778119, of differentiating between a chill-tolerant and a chill-sensitive haplotype. Preferably, the chill-tolerant haplotype corresponds to the TH line with a haplotype according to Table 2, and/or the chill-sensitive haplotype corresponds to the SL line with a haplotype according to Table 2. A molecular marker of the present invention may, for example, be a molecular marker which is capable, at one of the marker positions ma59778s31, ma59778s32, ma59778119, ma52594s01 and ma20205s01, of differentiating between a chill-tolerant and a chill-sensitive haplotype. A molecular marker may be an oligonucleotide, in particular a primer oligonucleotide, or it may be present in an isolated form. In a particularly preferred embodiment, the molecular marker of the present invention, alone or in combination with other molecular markers, is capable of detecting the chill tolerance-mediating nucleic acid. Furthermore, the present invention concerns the use of at least one of the molecular markers of the present invention for the identification or selection of a chill-tolerant maize plant in accordance with the invention or a portion thereof.

In a further aspect, the present invention concerns a method for the identification of a chill-tolerant maize plant or portions thereof in accordance with the invention as described above, comprising the steps of A) isolating DNA from the genome of a maize plant, and B) detecting an allele in a chromosomal interval flanked by the marker positions ma59778s31 and ma20205s01 on chromosome 4, optionally supplemented by a step C) for detection of at least one chromosomal interval which does not originate from the donor, or of an allele frequency which is at least partially raised in a chromosomal interval flanked by the marker positions ma59778119 and ma20205s01 or by the marker positions ma59778119 and ma52594s01. Preferably, the allele from step B) is found in a chromosomal interval flanked by the marker positions ma59778s31 and ma59778119 or ma59778s32 and ma59778119. In a particularly preferred embodiment, the allele from step B) is diagnostic for the chill tolerance-conferring nucleic acid. "Diagnostic" means that the allele lies either directly on the chill tolerance-conferring nucleic acid, or is closely coupled to the chill tolerance-mediating nucleic acid. In another particularly preferred embodiment, the molecular markers in accordance with the invention described above are used for the detection in step B).

In a further particularly preferred embodiment, in step B), in addition to a first allele, a second allele is also detected, wherein the first allele and the second allele constitute marker positions which flank a chromosomal interval which comprises the chill tolerance-conferring nucleic acid. In this regard, the first allele is preferably distal to the chill tolerance-conferring nucleic acid, preferably in a chromosomal interval between ma11840s01 and ma59778s31 or ma11840s01 and ma59778s32, and the second allele is proximal to the chill tolerance-conferring nucleic acid, preferably in a chromosomal interval between ma59778119 and ma20205s01 or ma59778119 and ma52594s01.

In a further aspect, the present invention concerns a method for the selection of a chill-tolerant maize plant or portions thereof in accordance with the invention as described above, comprising the method described above for the identification of a chill-tolerant maize plant or portions thereof in accordance with the invention as described above, supplemented by a further step for selection of the chill-tolerant maize plant or portions thereof on the basis of the detection of step B) and optionally of step C).

A further aspect concerns a method for the production of a maize plant in accordance with the invention, comprising a first step for crossing two maize plants, wherein one maize plant is a chill-tolerant maize plant comprising a first chromosomal interval between the marker positions ma59778s31 and ma59778119, which comprises a chill tolerance-conferring nucleic acid, and a further chromosomal interval flanked by the marker positions ma59778119 and ma20205s01, at least portions of which derive from the same donor as the first chromosomal interval, and/or which comprises a low allele frequency at least in parts, and as the second step, the method described above for selection of a chill-tolerant maize plant in accordance with the invention from the descendants of the cross in the first step. Preferably, the chill tolerance-conferring nucleic acid comprises one or more nucleic acid sequences selected from the group consisting of a) a nucleic acid sequence with one of the SEQ ID NOs: 29, 3, 7, 11, 15, 25 or 35, b) a nucleic acid sequence which has at least 98%, 99% or 99.5% identity with a sequence from a) or b), c) a nucleic acid sequence which differs from a nucleic acid sequence according to a) in accordance with the degeneracy of the genetic code, d) a nucleic acid sequence which codes for a protein with one of the SEQ ID NOs: 30, 4, 8, 12, 16 or 26 or a homologue, analogue or orthologue thereof. In a preferred exemplary embodiment, the chromosomal interval is on chromosome 4, which comprises a chill tolerance-conferring nucleic acid, an interval between the marker positions ma59778s32 and ma59778119 and/or the chill tolerance-conferring nucleic acid comprises a nucleic acid sequence selected from the group consisting of a) a nucleic acid sequence with SEQ ID NO: 29, b) a nucleic acid sequence which has at least 98%, 99% or 99.5% identity with a sequence from a), c) a nucleic acid sequence which differs from a nucleic acid sequence according to a) in accordance with the degeneracy of the genetic code, or d) a nucleic acid sequence which codes for a protein with SEQ ID NO 30 or a homologue, analogue or orthologue thereof; preferably, the nucleic acid sequence is operatively connected with a promoter which comprises the nucleotide sequence with SEQ ID NO: 33, or with an allele variant or a modified form of a promoter which comprises the nucleotide sequence with SEQ ID NO: 34, wherein the allele variant or the modified form has a comparable expression rate or level of expression to the promoter which comprises the nucleotide sequence with SEQ ID NO: 33. An "allele variant" or a "modified form of the promoter" means a promoter which has an expression rate or expression level reduced by more than 5%, 10%, 15%, 20%, 25%, 30%, 40% or 50% compared with the expression rate or expression level produced by the promoter which comprises the nucleotide sequence with SEQ ID NO: 34. A "comparable expression rate or expression level" means that the allele variant or the modified form of the promoter which comprises the nucleotide sequence with SEQ ID NO: 34 essentially has an expression rate or expression level which differs by no more than 20%, 18%, 16%, 14% or 12%, preferably by no more than 10%, 9%, 8%, 7% or 6%, or particularly preferably no more than 5%, 4%, 3%, 2%, 1%, 0.5% or 0% from the expression rate or expression level of the promoter which comprises the nucleotide sequence with SEQ ID NO: 33.

In an additional aspect, the present invention concerns a method for increasing the yield of plants or maize plants, comprising cultivating transgenic chill-tolerant plants in accordance with the invention, mutated chill-tolerant plants or chill-tolerant maize plants in accordance with the invention as well as harvesting an increased yield. The growing plants have an increased chill tolerance which to a certain extent make them capable, during a chill stress phase, of growing faster than a plant with a comparable genotype which does not contain a nucleic acid in accordance with the invention in its genome. This leads to the fact that when the transgenic chill-tolerant plants in accordance with the invention are harvested, mutated chill-tolerant plants or chill-tolerant maize plants in accordance with the invention provide and increased yield.

In a further additional aspect, the present invention encompasses a method for reducing the use of herbicides when cultivating plants or maize plants, in particular during the early development of the plants or maize plants, comprising cultivating transgenic chill-tolerant plants in accordance with the invention, mutated chill-tolerant plants or chill-tolerant maize plants in accordance with the invention. The growing plants have an increased chill tolerance, which to a certain extent make them capable, during a chill stress phase, of growing faster than a plant with a comparable genotype which does not contain a nucleic acid in accordance with the invention in its genome. This means that the plants can compete against growing weeds/foreign vegetation. Preferably, the cultivated plants also have a resistance against herbicides.

Some of the terms used in this application will now be defined in more detail:

The term "hybridize" or "hybridization" means a process in which a single stranded nucleic acid molecule precipitates out with a substantially complementary nucleic acid strand, i.e. forms base-pairs. Standard processes for hybridization are described, for example, in Sambrook et al. 2001. Preferably, this means that at least 60%, more preferably at least 65%, 70%, 75%, 80% or 85%, particularly preferably 90%, 91%, 92%, 93%, 94%, 95%, 96%, 97%, 98% or 99% of the bases of the nucleic acid molecule base-pairs with the substantially complementary nucleic acid strand. The possibility of such a base-pairing is dependent on the stringency of the hybridization conditions. The term "stringency" relates to the hybridization conditions. High stringency is the case in which base-pairing is difficult; low stringency is the case when base pairing is easier. The stringency of the hybridization conditions is dependent, for example, on the salt concentration or ionic strength and the temperature. In general, the stringency can be increased by increasing the temperature and/or by reducing the salt content. The term "stringent hybridization conditions" means those conditions in which a hybridization takes place substantially only between homologous nucleic acid molecules. The term "hybridization conditions" thus not only refers to the conditions during actual pairing of the nucleic acids, but also to the conditions prevailing during the associated washing steps. Examples of stringent hybridization conditions are conditions under which primarily, only those nucleic acid molecules hybridize which have at least 70%, preferably at least 75%, at least 80%, at least 85%, at least 90% or at least 95% sequence identity. Examples of stringent hybridization conditions are: hybridization in 4×SSC at 65° C. and subsequent multiple washing in 0.1×SSC at 65° C. for approximately 1 hour. The term "stringent hybridization conditions" as used here may also mean: hybridization at 68° C. in 0.25 M sodium phosphate, pH 7.2, 7% SDS, 1 mM EDTA and 1% BSA for 16 hours and subsequently washing twice with 2×SSC and 0.1% SDS at 68° C. Preferably, hybridization is carried out under stringent conditions.

In the context of the invention, the term "homologue" means a protein with the same phylogenetic origin; the term "analogue" means a protein which carries out the same function, but has a different phylogenetic origin; and the term "orthologue" means a protein from another species which carries out the same function.

Unless otherwise stated, a "plant" in the context of the invention may be any species selected from dicotyledon, monocotyledon and gymnosperm plants. Examples are *Hordeum vulgare, Sorghum bicolor, Secale cere ale, Triticale, Saccharum officinarum, Zea mays, Setaria italic, Oryza sativa, Oryza minuta, Oryza australiensis, Oryza alta, Trificum aestivum, Trificum durum, Hordeum bulbosum, Brachypodium distachyon, Hordeum marinum, Aegilops tauschii, Beta vulgaris, Helianthus annuus, Daucus glochidiatus, Daucus pusillus, Daucus muricatus, Daucus carota, Eucalyptus grandis, Erythranthe guttata, Genlisea aurea, Gossypium* sp., *Musa* sp., *Avena* sp., *Nicofiana syl-*

*vestris, Nicotiana tabacum, Nicotiana tomentosiformis, Solanum lycopersicum, Solanum tuberosum, Coffea canephora, Vitis vinifera, Cucumis sativus, Morus notabilis, Arabidopsis thaliana, Arabidopsis lyrata, Arabidopsis arenosa, Crucihimalaya himalaica, Crucihimalaya wallichii, Cardamine flexuosa, Lepidium virginicum, Capsella bursa pastoris, Olmarabidopsis pumila, Arabis hirsuta, Brassica napus, Brassica oleracea, Brassica rapa, Brassica juncacea, Brassica nigra, Raphanus sativus, Eruca vesicaria sativa, Citrus sinensis, Jatropha curcas, Glycine max* and *Populus trichocarpa*. A plant in accordance with the invention is preferably a plant from the genus *Zea*, in particular the species *Zea mays*, or sorghum.

"Operatively connected" means bound in the same nucleic acid molecule in a manner such that the connected elements are positioned with respect to each other and orientated such that a transcription of the nucleic acid molecule can take place. A DNA which is operatively connected with a promoter is under the transcriptional control of this promoter.

Examples of plant "organs" are leaves, plant stems, stems, roots, vegetative buds, meristems, embryos, anthers, ovulae or fruit. Plant "portions" mean a combination of several organs, for example a flower or a seed, or a portion of an organ, for example a section from the stem. Examples of plant "tissue" are callus tissue, soft tissue, meristem tissue, leaf tissue, stem tissue, root tissue, plant tumour tissue or reproductive tissue. The term plant "cells" should be understood to mean, for example, isolated cells with a cell wall or aggregates thereof or protoplasts.

A "functional fragment" of a nucleotide sequence means a section of a nucleotide sequence which comprises the identical or a comparable functionality as the total nucleotide sequence from which the functional fragment originates. As such, the functional fragment may have a nucleotide sequence which is identical to or homologous with the total nucleotide sequence to an extent of at least 50%, 55%, 60%, 65%, 70%, 75%, 80%, 85%, 90%, 92%, 94% 96%, 97%, 98% or 99%. Furthermore, a "functional fragment" of a nucleotide sequence may also mean a section of a nucleotide sequence which changes the functionality of the total nucleotide sequence, for example during the course of post-transcriptional or transcriptional gene silencing. As such, the functional fragment of a nucleotide sequence may comprise at least 14, 15, 16, 17, 18, 19, 20, 21, 22, 23, 24 or 25, preferably at least 30, 35, 40, 45, 50, 60, 70, 80, 90, 100, 120 or 140, particularly preferably at least 160, 180, 200, 250, 300, 350, 400, 450, 500, 600, 700, 800, 900 or 1000 successive nucleotides of the total nucleotide sequence.

The term "heterologous" means that the introduced polynucleotide originates, for example, from a cell or an organism with a different genetic background from the same species or from another species, or is homologous to the prokaryotic or eukaryotic host cell, but is then localized in a different genetic environment and thus differs from any naturally available corresponding polynucleotide. A heterologous polynucleotide may be present in addition to a corresponding endogenous gene.

In connection with the present invention, the term "regulatory sequence" means a nucleotide sequence which influences the specificity and/or the expression strength, for example in that the regulatory sequence confers a specific tissue specificity. A regulatory sequence of this type may be located upstream of the transcription initiation point of a minimal promoter, but also downstream thereof such as, for example, in a transcribed but not translated leader sequence or within an intron.

The term "chromosomal interval" means a continuous linear section on a genomic DNA which is present in a single chromosome in the plant or on a chromosomal interval. If the chromosomal interval is defined by providing two flanking marker positions, this represents the end points of the interval on the distal and proximal sides. In this manner, the marker positions which defines the ends of the interval may themselves also be part of the interval. In the description, an interval is also specified as being "between marker position A and marker position B". In this case, the chromosomal interval is constituted by a continuous linear section of DNA which is localized between the two specified marker positions. The marker positions are not the end points of the interval at the distal and proximal side. The specified marker positions themselves do not form part of the interval.

The term "allele" involves one or two or more nucleotide sequences at a specific locus in the genome. A first allele is on a chromosome; a second is on a second chromosome at the same position. If the two alleles are different, then these are heterozygous, and if the alleles are the same, they are homozygous. Different alleles of a gene (gene allele) differ in at least one SNP. Depending on the context of the description, an allele also means only a single SNP which, for example, allows a differentiation between two haplotypes.

A "maize plant" should be understood to mean a plant from the species *Zea mays* as well as its subspecies such as, for example, *Zea mays* ssp. *mays, Zea mays* ssp. *mexicana* or *Zea mays* ssp. *parviglumis*.

A "marker" or "molecular marker" is a nucleotide sequence which is used as a reference or orientation point. A marker for detecting a recombination event should be capable of monitoring differences or polymorphisms within a plant population. For markers, these differences are on a DNA level and are, for example, differs in polynucleotides such as, for example, SSRs (simple sequence repeats), RFLPs (restriction fragment length polymorphisms), FLPs (fragment length polymorphisms) or SNPs (single nucleotide polymorphisms). The markers may be derived from genomic or expressed nucleic acids such as, for example, spliced RNA, cDNA or ESTs, and may also refer to nucleic acids which are used as probes or primer pairs and as such are capable of amplifying a sequence fragment using PCR-based methods. Markers which concern genetic polymorphisms between parts of a population can be detected by means of an established method from the prior art (An Introduction to Genetic Analysis. 7th Edition, Griffiths, Miller, Suzuki et al., 2000). These include, for example DNA sequencing, PCR-based, sequence-specific amplification, detection of RFLPs, detection of polynucleotide polymorphisms using allele-specific hybridization (ASH), the detection of SSRs, SNPs or AFLPs. Furthermore, methods for the detection of ESTs (expressed sequence tags) and RAPD (randomly amplified polymorphic DNA) are also known. Depending on the context, the term "marker" in the description also means a specific chromosome position in the genome of a species, where a specific marker (for example SNP) can be found. Such a marker position may be used in order to monitor the presence of a coupled locus, for example a coupled locus which contributes to the expression of a specific phenotype trait. As an example, the marker locus may also be used in order to observe the segregation of alleles at a locus (QTL or individual gene) which are genetically or physically closely coupled to the marker position.

The present invention will now be described in the examples with reference to the figures which are, however, non-limiting in nature. For the purposes of the invention, all documents cited herein are incorporated by reference. In the figures:

FIG. 1: shows the diagrammatic sequence for candidate genes in the region between the marker positions ma59778s31 and ma59778119, comparing SL, TH and B73 AGPv02. Solid-lined boxes: annotated gene; dotted-lined boxes: information from marker-supported mapping; region in which a genetic polymorphism occurs between the SL and TH lines are ORF-SL-01/ORF-TH-01, ORF-SL-02/ORF-TH-02, Region-SL-13a/Region-TH-13a, Region-SL-13b/Region-TH-13b, ORF-SL-05, ORF-SL-06, Region-SL-11/ORF-TH-11, ORF-SL-12/Region-TH-12, Region-SL-06/Region-TH-06, ORF-SL-09/ORF-TH-09 and Region-SL-07/Region-TH-07; arrowheads show the 5'-3' direction, irrespective of the DNA strand on which the respective gene is; SL: chill-sensitive genotype; TH: chill-tolerant genotype; B73: maize line the genome of which has been sequenced and which is used by the person skilled in the art for maize breeding as a reference genome. Using the B73 data, it is possible, in addition to the marker-supported candidate gene position, to provide the relative position (relative to B73 reference genome) as well.

FIG. 2: additive marker effect (half the difference between the means of the two homozygous marker sites) for the phenotype trait of early plant height and leaf green colour of the investigated plants after chill stress in experiments the field (on the left) and in a climatic chamber (on the right). The length of a bar behind the mark for the marker position indicates the magnitude of the influence of the genetics on the manifestation of said features after chill stress. According to this, the marker positions ma59778s32, ma59778116 and ma59778119 decide to a great extent whether a plant is chill-tolerant. The measurements and calculations for FIG. 2 can be seen in Table 5.

Figure 3:
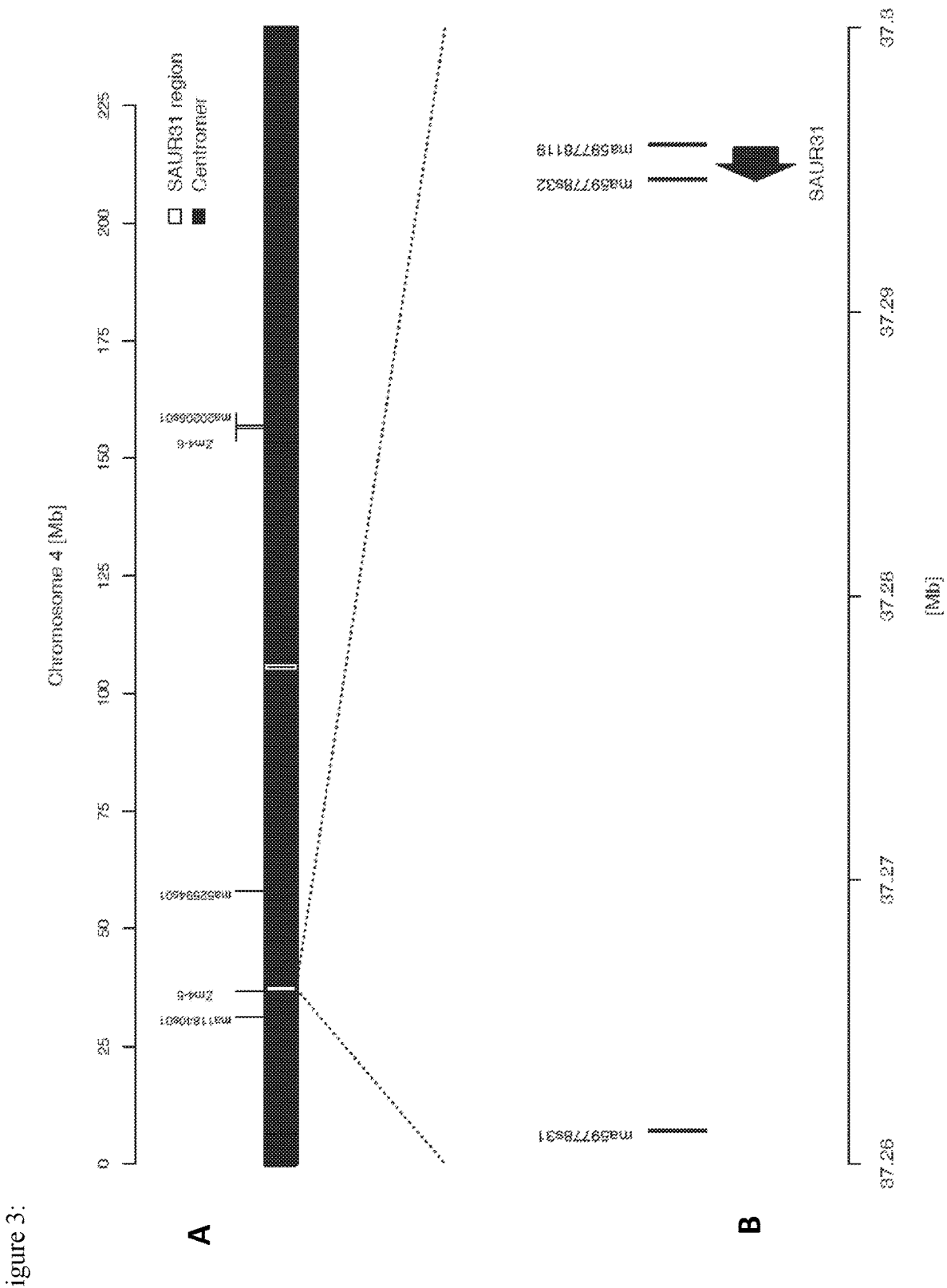

FIG. 3 shows, in the upper region (A), the diagrammatic representation of chromosome 4 from Zea mays with a total of approximately 225 megabases. The position of the centromer and four important marker positions and their names are clearly marked. In the lower region (B), an enlarged section around the marker Zm4-5 can be seen in which the gene SAUR31 can also be found. This constitutes fine mapping which very precisely shows the position of SAUR31 using three marker positions. SAUR31 is flanked by the two markers ma59778s32 and ma59778119.

Figure 4:
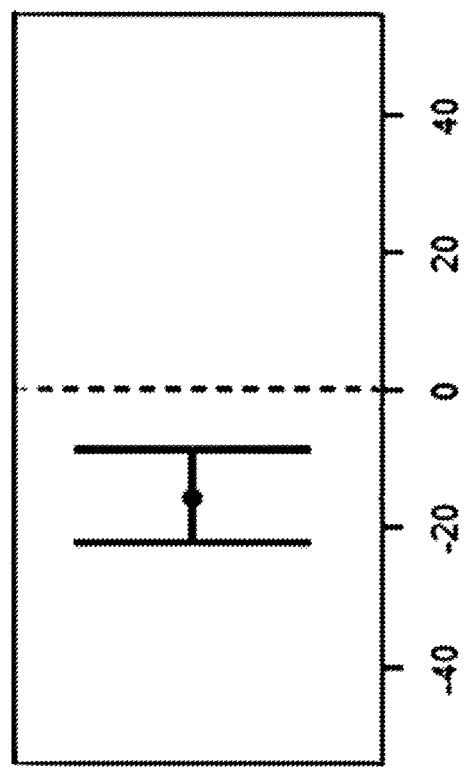
Figure 4:
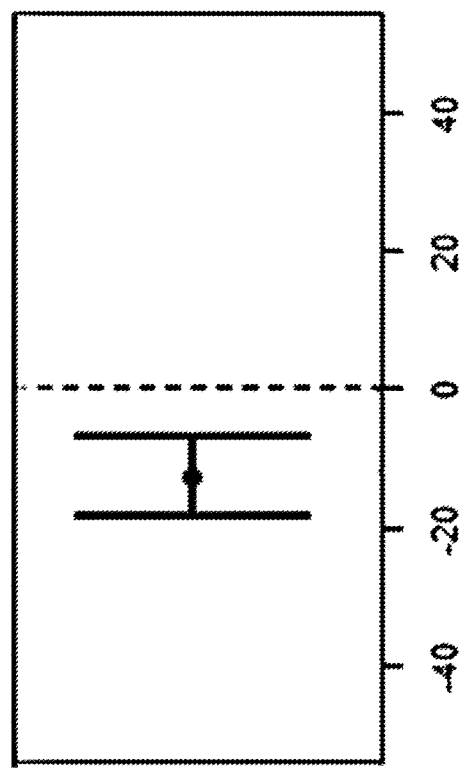

FIG. 4 shows the mean of the trait "plant height" of plants with mutations in the 5'UTR region before the SAUR31 gene compared with the mean of the non-mutagenized starting line. It shows two different points in time for measurement (two different stages of plant development): the measurement shown on the left was carried out 50 days after sowing and the second measurement on the left was carried out 27 days after the first measurement shown on the left. The field emergence was carried out under cool spring conditions and both measurements were carried out before the maize flowered. The data verify the significance of SAUR31 on the phenotype manifestation of the "chill tolerance" trait.

FIG. 5 shows the extent of genetic diversity using the allele frequencies in the Dent gene pool (lower line) and in the Flint gene pool (upper line) on chromosome 4. Maximum genetic diversity is at an allele frequency of 0.5. The values 0.0 and 1.0 represent extremes which indicate the complete fixing of a specific genetic background without any variability. As can be seen from the figure, the Dent gene pool shows clear genetic fixing compared with the Flint gene pool, in particular bordering the region for chill tolerance-conferring QTL containing the gene SAUR31.

Figure 6:
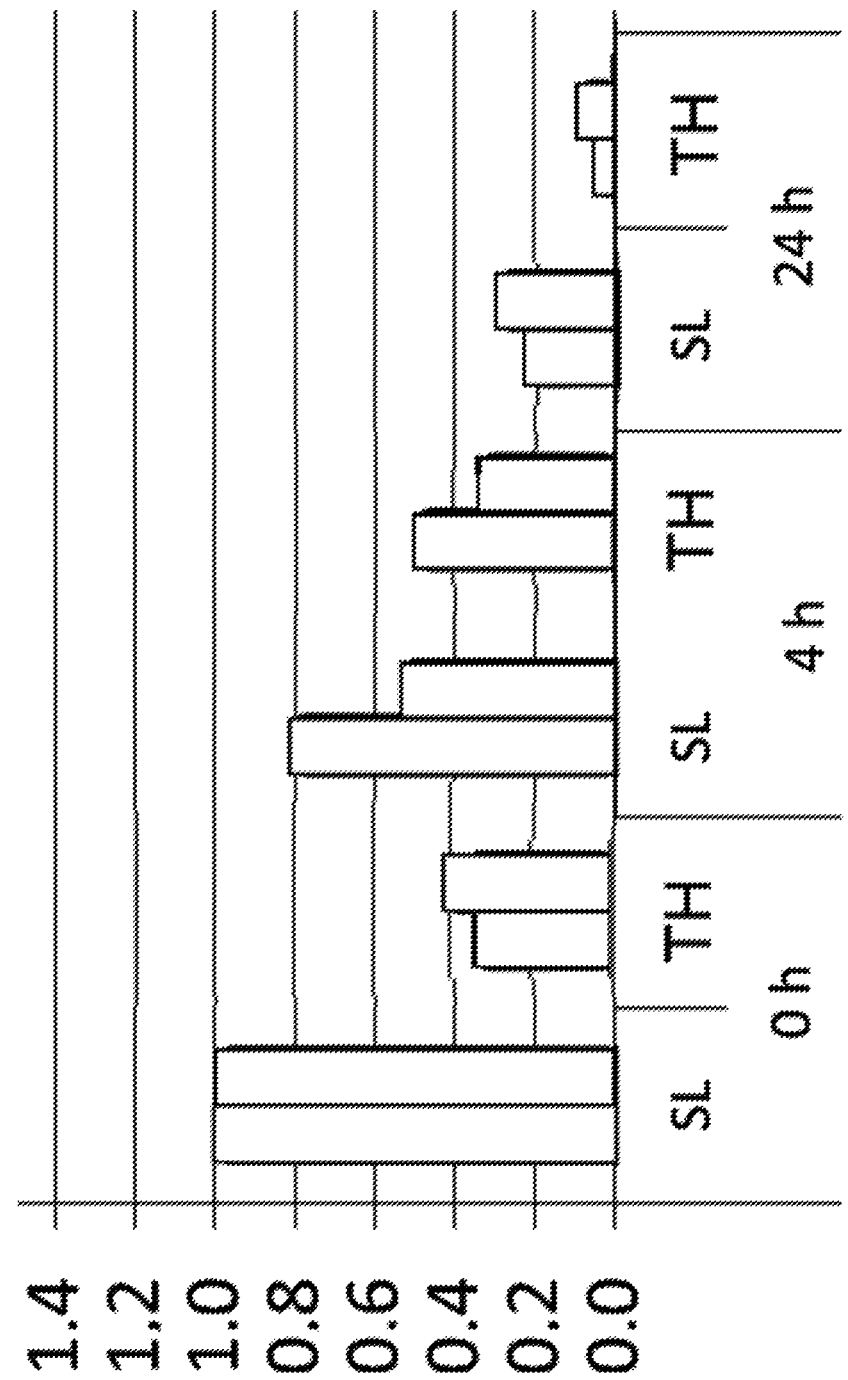

FIG. 6 shows the relative expression of the SAUR31 gene in chill-sensitive and chill-tolerant lines. The plants were cultivated for two weeks at temperatures of 22° C./25° C. and then were subjected to a chill stress of 6° C./8° C. for 24 h. At the start of the chilling treatment (0 h) as well as after 4 h and 24 h, the above-ground parts of eight plants were used for RNA isolation. The RNA was investigated using RT-PCR. The tests were carried out twice and both results are shown as two adjacent bars. All of the values were standardized to the SL 0 h value, which was defined as 1.

SEQ ID NOs: 1 to 35 show:

SEQ ID NO: 1 open reading frame ORF-SL-01 from the SL line

SEQ ID NO: 2 the protein coded by SEQ ID NO: 1

SEQ ID NO: 3 open reading frame ORF-TH-01 from the TH line

SEQ ID NO: 4 the protein coded by SEQ ID NO: 3

SEQ ID NO: 5 open reading frame ORF-SL-02 from the SL line

SEQ ID NO: 6 the protein coded by SEQ ID NO: 5

SEQ ID NO: 7 open reading frame ORF-TH-02 from the TH line

SEQ ID NO: 8 the protein coded by SEQ ID NO: 7

SEQ ID NO: 9 open reading frame ORF-SL-03 from the SL line

SEQ ID NO: 10 the protein coded by SEQ ID NO: 9

SEQ ID NO: 11 open reading frame ORF-TH-03 from the TH line

SEQ ID NO: 12 the protein coded by SEQ ID NO: 11

SEQ ID NO: 13 open reading frame ORF-SL-04 from the SL line

SEQ ID NO: 14 the protein coded by SEQ ID NO: 13

SEQ ID NO: 15 open reading frame ORF-TH-04 from the TH line

SEQ ID NO: 16 the protein coded by SEQ ID NO: 15

SEQ ID NO: 17 open reading frame ORF-SL-05 from the SL line

SEQ ID NO: 18 the protein coded by SEQ ID NO: 17

SEQ ID NO: 19 open reading frame ORF-SL-06 from the SL line

SEQ ID NO: 20 the protein coded by SEQ ID NO: 19

SEQ ID NO: 21 open reading frame ORF-SL-12 from the SL line

SEQ ID NO: 22 the protein coded by SEQ ID NO: 21

SEQ ID NO 23 open reading frame ORF-SL-08 from the SL line

SEQ ID NO: 24 the protein coded by SEQ ID NO: 23

SEQ ID NO: 25 open reading frame ORF-TH-08 from the TH line, which is identical to ORF-SL-08 from the SL line SEQ ID NO: 26 the protein coded by SEQ ID NO: 25

SEQ ID NO: 27 open reading frame ORF-SL-09 from the SL line, which corresponds to the gene SAUR 31.

SEQ ID NO: 28 the protein coded by SEQ ID NO: 27

SEQ ID NO: 29 open reading frame ORF-TH-09 from the TH line, which corresponds to the gene SAUR 31, wherein the gene is present in an allele variation which apparently contributes to the manifestation of chill tolerance SEQ ID NO: 30 the protein coded by SEQ ID NO: 29

SEQ ID NO: 31 open reading frame ORF-B73-09 from the maize genome reference line B73, which corresponds to the gene SAUR 31

SEQ ID NO: 32 the protein coded by SEQ ID NO: 31

SEQ ID NO: 33 promoter region of the gene SAUR31 corresponding to the allele variation ORF-TH-09, wherein the promoter region is present in an allele variation which apparently contributes to the manifestation of chill tolerance SEQ ID NO: 34 promoter region of the gene SAUR31 corresponding to the allele variation ORF-SL-09

SEQ ID NO: 35 open reading frame ORF-TH-11 from the TH line

SEQ ID NO: 36 primer

SEQ ID NO: 37 primer

SEQ ID NO: 38 mutated version of SAUR31 with base exchange of adenine for a guanine in position −25 (relative to translation start); the codogenic strand is shown in the 5' to 3' direction.

EXAMPLES

A QTL mapping study was carried out in a bi-parental mapping population of the inbred lines SL and TH. The inbred line SL is sensitive to cool temperatures during early development of the plant in the field, while TH is the tolerant parent line.

Field experiments were carried out with 720 DH (double haploid) lines in 8 locations (Presterl et al., 2007). The 720 DH lines were genotyped with 188 SSR markers over the genome. A phenotyping of the plant development was carried out at an early stage (six to eight fully developed leaves) and the total yield of fresh plant material and the number of plants were determined as a measure of the field chill tolerance.

The QTL mapping was calculated on the level of the line per se and test crosses. As a result, 7 QTL regions could be determined on 6 chromosomes, wherein the strongest QTL was detected on chromosome 4 in a 4 cM interval with 33.7% of the determined phenotype variance. In the first QTL mapping, only 3 SSR markers covered the genome region (Presterl et al. 2007). On the B73 AGPv01 physical map, this region covered 155 Mb. The QTL mapping was later verified in this population. Further fine mapping of this region was carried out. 23 markers for the QTL region were developed and near isogenic lines (NILs) were genotyped for the large QTL region and further recombination plants were derived from crosses between NILs and the sensitive SL parent, in order to develop NILs with smaller chromosome segments. Two flanking polymorphic markers for the QTL region could be mapped at 36.7 Mb (Zm4-5) and 156.4 Mb (Zm4-6) on the physical map of B73 AGPv01 (see FIG. 3). The newly developed markers could be mapped at 37.1 Mb. The novel markers narrowed the QTL region to 119.7 Mb, but because of the low recombination frequency in this region (pericentromeric region) and insufficient genomic resources, a smaller interval could not be determined (Baliashvili, 2011).

A phenotype test to determine the cold sensitivity was established, wherein the plants were cultivated in a growth chamber for 14 days (three leaf stage) during the day at 25° C. and at night at 22° C. Following this, the temperature was reduced to 8° C. during the day and 6° C. at night for one week. The yield at 25° C. during the day and 22° C. at night after chilling treatment produced a chlorotic lesion in the fourth and fifth leaf when the plant was sensitive to the chilling treatment (SL line). The tolerant plants remained green (TH line).

Molecular analysis and genomic resources: in order to enrich the QTL region with the novel molecular markers, novel genomic resources were produced. Thus, a sequence capture strategy with the SL, TH lines and the NIL TH-N4-32-line 28 produced novel polymorphism SNP markers in a comparison between SL and TH. BAC sequences from two BAC libraries which derived from a line which carried the sensitive SL allele on the QTL and a line which carried the tolerant TH allele on the QTL were also prepared. BAC library screening, sequencing and scaffold construction were carried out. The BAC libraries were screened with the known markers for the QTL region in both libraries. Three BAC clones from the SL-BAC libraries and four BAC clones from the TH-BAC libraries were sequenced with three different next generation techniques. For the SL-BAC scaffold, a total size of 284 kb and for the TH-BAC scaffold, a total size of 356 kb were put together, which both contained the target region between ma59778s31 and ma59778119 including flanking regions. The missing polymorphism marker in the direction towards the centromer could be established by comparison of the BAC sequences from both libraries. Beyond 38729663 bp on the B73 AGPv02 map, no polymorphism could be detected between the two lines. In position 37297901 bp, ma59778119 was confirmed as the last functional marker. This marker enabled 3' determination of the QTL region, because from position 38729663 onwards, no further polymorphisms were observed between SL and TH. Without this marker, it would not have been possible to identify introgressions as small as 35 kb (from marker ma59778s31 to ma59778119) (see FIG. 3).

Identification of candidate genes: the BAC scaffolds of both BAC libraries were annotated. Candidate genes/regions were confirmed when they matched the results of the recombinant screenings, their functional annotation, the results of the expression analyses, and whether they exhibited polymorphisms between the SL and TH lines. A total of nine open reading frames (ORFs) could be annotated on the S1-BAC scaffold, and seven ORFs could be annotated on the TH-BAC scaffold between ma59778s31 and 7202707. ORFs could be detected, wherein most of them coded for complete or shortened transposable elements (Tables 1a to c). It is known that such elements, when located close to genes, can influence their expression (Butelli, Eugenio, et al. "Retrotransposons control fruit-specific, cold-dependent accumulation of anthocyanins in blood oranges." The Plant Cell 24.3 (2012): 1242-1255; Meihls, Lisa N., et al. "Natural variation in maize aphid resistance is associated with 2,4-dihydroxy-7-methoxy-1,4-benzoxazin-3-one glucoside methyltransferase activity." The Plant Cell 25.6 (2013): 2341-2355.).

Two annotated ORFs (ORF-SL-03/ORF-TH-03, ORF-SL-08/ORF-TH-08) exhibited no genomic sequence differences between SL and TH. Four annotated ORFs (ORF-SL-02/ORF-TH-02, ORF-SL-04/ORF-TH-04, ORF-SL-09/ORF-TH-09, ORF-TH-11/Region-SL-11, ORF-SL-12/Region-TH-12) exhibited polymorphisms either from individual nucleotides or insertions/deletions; one ORF (ORF-SL-01/ORF-TH-01) mapped only partially between the genotypes. Two ORFs (ORF-SL-05, ORF-SL-06), which were identified and annotated in SL were missing in TH. As a result, all ORFs which are polymorphic, are missing between the two genotypes or exhibit a different expression, are suitable candidate genes for the observed property of chill tolerance. ORF-09, which was identified as SAUR31 in the maize database, is of particular interest. SAUR genes (small auxin upregulated RNA) react to auxin.

Validation of candidate genes: screening of a TILLING population with the tolerant allele from TH for the chill tolerance-conferring QTL region on chromosome 4 was started for the candidate genes, in particular ORF-SL-09, ORF-TH-09 (B73: GRMZM2G420812). Two amino acid exchanges could be identified in the mutants, and two mutants exhibited polymorphisms in the 5' region of the gene.

The expression of selected candidate genes was analysed by qRT-PCR in both parent lines and in two NILs which differ in chill tolerance. Plants were cultivated in a growth chamber under the conditions described above, and the expression of the candidate genes was analysed at three points in time during the chilling treatment:
1. before the chilling treatment (t0),
2. four hours after the beginning of the chilling treatment (t4) and
3. 24 hours after the beginning of the chilling treatment (t24).

The expression of the SAUR31 gene (ORF-09) was higher in the chill-sensitive lines and decreased at each measurement point. Two of the analysed transposable elements (ORF-08 and ORF-02) also exhibited a different expression between sensitive and tolerant lines (FIG. 6). Tables 1a to c summarize the candidate genes, their annotation, the observed polymorphisms and the results of the expression analysis. The differences in expression could be assumed to be the cause of the retarded growth under cool conditions.

Development of a SAUR31 mutant and its analysis in field trials: because of the particular influence of SAUR31 on the phenotype manifestation of chill tolerance, a functional validation of this gene was sought. The strategy was an undirected EMS mutagenesis of polyamide-imide pollen (see Neuffer and Coe, 1978; Paraffin oil technique for treating mature corn pollen with chemical mutagens. Maydica 23: 21-28). After mutagenesis of an original line (KWS279), M1 seed was cultivated and next, a leaf harvest of the corresponding individual plants was carried out. The subsequent DNA extraction from the harvested leaf samples carried out using specific primers (SEQ ID NOs: 36 and 37), produced a DNA fragment of the SAUR31 gene for amplification. By sequencing this DNA fragment, deviations from the original sequence of the SAUR31 gene could be specifically detected and traced back to the corresponding individual plant. By means of this method, one such mutant could successfully be identified which had a mutation of the SAUR31 gene in the 5'-UTR (untranslated region). Here, an exchange of G/C for A/T in position (−25), starting from the start ATG in the original sequence was observed. The associated sequence is given in SEQ ID NO: 38. The heterozygotic mutation identified in the M1 generation was fixed by selfing the corresponding individual plant in the following M2 generation.

In field trials at location A, the mutants were cultivated in rows each with 20 plants repeated 5 times. The non-mutagenized original line was cultivated in the direct vicinity of the mutant in order to ensure the best possible comparison. The statistical evaluation of the mean values of the mutants to the original line exhibited a significantly poorer growth of the mutants under cool spring conditions compared with the original line (FIG. 4). FIG. 4 shows the means for the plant growth height trait for the mutants with respect to the mean of the non-mutagenized starting line at two different measurement points (two different stages of plant development): the second measurement shown on the right in FIG. 4 was carried out 27 days after the first measurement shown on the left. The field emergence was carried out under cool spring conditions.

Development of recombinant NILs: using the novel molecular markers, furthermore, recombinant NILs, which originated from the NILs TH-N4-8X, TH-N4-56X and TH-N4-32, were developed. Very small recombination events could be identified, which comprised 34.729 kb on the B73AGPv02 physical map, 32.731 kb on the SL-BAC scaffold and 25.662 kb on the TH-BAC scaffold (the edges were given by marker ma59778s31 to marker ma59778119) (Table 2). An overview of the NILs which were used in the various challenges is given in Table 2.

TABLE 2

Overview of NILs and parents used for the various challenges. The marker positions with reference to AGPv2 are: ma11840s01 = 31306276 bp; ma59778s31 = 37263172 bp; ma59778s32 = 37296672 bp; ma59778119 = 37297901 bp; ma52594s01 = 58033711 bp; ma20205s01 = 156998152 bp.

| lines | ma11840s01 | ma59778s31 | ma59778s32 | ma59778119 | ma52594s01 | ma20205s01 | haplotype |
|---|---|---|---|---|---|---|---|
| SL | A | C | C | A | A | G | HP1 |
| TH | G | T | T | C | A | A | HP2 |
| TH-N4-32 | G | T | T | C | A | G | HP3 |
| TH-N4-8X | G | T | T | C | A | A | HP2 |
| TH-N4-56X | G | T | T | C | A | G | HP3 |
| SL-BAC library | A | C | C | A | A | G | HP1 |
| TH-BAC library | G | T | T | C | A | A | HP2 |
| KWS279-TILLING | G | T | T | C | A | A | HP2 |
| NIL-003-RNAseq | G | T | T | C | A | G | HP3 |
| NIL-011-RNAseq | A | C | C | A | A | G | HP1 |
| NIL1 phenotype |  | T | T | C | A |  | HP1 |
| NIL2 phenotype |  | C | T | C | A |  | HP4 |
| NIL3 phenotype |  | T | C | A | A |  | HP5 |
| NIL4 phenotype |  | T | C | C | A |  | HP6 |

Phenotype evaluation: the NILs which contained the donor segment at marker ma59778s32 but the SL allele contained marker ma59778s31 and vice versa, were phenotyped in the field and in the growth chamber.

NILs and the parent lines were evaluated for plant development in an early stage in two locations A and B in Northern Germany, which are known to have low temperatures during early growth periods for maize Experiment 1 was carried out at two locations with 27 recombinant plants in 20 replications, and experiment 2 consisted of 38 recombination plants in 10 replications, evaluated at location A. In both experiments, NILs were planted in a row with 20 plants. The plant development was measured as the plant height at the start of the elongation phase for the stem.

TABLE 3

Mean of heritability as a function of test location for early plant height for experiments 1 and 2

| | Experiment 1 | | | Experiment 2 |
|---|---|---|---|---|
| Parameter | Several locations | Location A | Location B | Location A |
| Mean [cm] | 67.4 | 61.0 | 73.8 | 58.0 |
| Mean TH [cm] | 83.0 | 76.2 | 89.8 | 79.9 |
| Mean SL [cm] | 64.8 | 59.0 | 70.6 | 58.7 |
| LSD5% [cm] | 1.9 | 2.4 | 3.0 | 2.6 |
| Heritability [%] | 98.5 | 97.2 | 97.2 | 97.4 |

Early plant height exhibited a very high heritability (>97%, Table 3). The two parent lines SL and TH were included in both experiments and differed significantly in early plant height.

Early plant height of NILs was calculated as the percentage of sensitive SL parents (Table 3). RecNILs with identical genotypes in the chromosomal interval between markers ma59778s31 and ma59778119 were brought together as haplotypes (Table 4). RecNILs which exhibited the SL genotype at markers ma59778s32, ma59778119 and ma59778116, had a clearly lower early plant height compared with the corresponding TH genotypes. The TH variant surprisingly had a plant length which was increased by about 35%; in absolute terms, approximately an additional 21 cm. Two NILs with the SL genotype at markers ma59778119 and ma59778116 exhibited a similarly low early plant height.

In addition, the NILs were phenotyped in the climatic chamber using the phenotype tests described above. The lines were cultivated for two weeks in a greenhouse (25/22° C.) and transferred into the climatic chamber for one week at 8/6° C. (cool conditions); after recovering for one week in the greenhouse (25/22° C.), the green colour of leaves four and five was evaluated between 0 (yellow) and 100% (green). In this regard, a value of 100% represented complete maintenance of the green leaf colour and a value of 0% represented completely yellow (chlorosis). It was seen that the TH variant was superior to the SL variant even with maintenance of chlorophyll under chill stress. In total, values of 10% to 85% were measured. The leaf green colour loss for the TH variants in this regard was reduced by 19% up to 75% compared with the SL variants.

TABLE 4

Tabular overview of NIL haplotypes, represented with different number (N) of individual NILs and their phenotype results for the properties of early plant height (SL = 100%) and greenness of leaves.

| Lines | Haplotype | Early plant height [% SL] | N | Green colour [%] | N |
|---|---|---|---|---|---|
| NIL1 phenotype | HP2 | 107.6 | 22 | 83.1 | 10 |
| NIL2 phenotype | HP4 | 106.1 | 6 | 63.1 | 7 |
| NIL3 phenotype | HP5 | 92.8 | 16 | 34.2 | 5 |

TABLE 4-continued

Tabular overview of NIL haplotypes, represented with different number (N) of individual NILs and their phenotype results for the properties of early plant height (SL = 100%) and greenness of leaves.

| Lines | Haplotype | Early plant height [% SL] | N | Green colour [%] | N |
|---|---|---|---|---|---|
| NIL4 phenotype | HP6 | 94.3 | 2 | 15.0 | 2 |
| SL | HP1 | 100 | 1 | 10 | 1 |

In addition, the effects of the marker in the target interval for the results from the field and the climatic chamber trials using an individual marker regression strategy (FIG. 1) were calculated. The markers which are physically close to or in the gene ORF-09 (ma59778120-ma59778119) exhibited the largest effects and were significantly associated with the two phenotype measurements. In the field trial, 6% of the additional effect corresponded to a difference between the two homozygous marker classes of 12%. In absolute terms, this represents 7.8 cM, which is 40% of the phenotype difference between SL and TH. For the growth chamber, the additive effect was 22.7% of the two closest flanking markers.

TABLE 5

LOD values (logarithmic odds ratio, statistical estimation of the probability of a marker and trait manifestation being inherited in a coupled manner. LOD = 3 is usually taken to be the significance threshhold) and additive marker effects (corresponds to half the difference of the two homozygotic marker manifestations) for the early plant height and green coloration of leaves phenotypes for the investigated recombinant plants in the field and in the climatic chamber experiments

| | | Early plant height | | Green coloration | |
|---|---|---|---|---|---|
| Marker | Position | LOD | Effect [%] | LOD | Effect [%] |
| zm00139s01 | 37227335 | 0 | 0.52 | 0 | 0.29 |
| ma59778s17 | 37250743 | 0.3 | 1.09 | 0 | 2.27 |
| ma59778s20 | 37255740 | 0.2 | 1.02 | 0 | 2.27 |
| ma59778s21 | 37255778 | 0.2 | 0.94 | 0 | 1.45 |
| ma59778s22 | 37257777 | 0.1 | 0.79 | 0 | 1.67 |
| ma59778s24 | 37258325 | 0.2 | 0.89 | 0 | 2.27 |
| ma35241s01 | 37258811 | 0.3 | 1.09 | 0.1 | 4.10 |
| ma59778s25 | 37258935 | 0.3 | 1.09 | 0 | 2.27 |
| ma59778s26 | 37260907 | 0.3 | 1.09 | 0.1 | 5.32 |
| ma59778s27 | 37260916 | 0.3 | 1.09 | 0.1 | 4.10 |
| ma59778s30 | 37263151 | 0.2 | 0.89 | 0.1 | 4.10 |
| ma59778s31 | 37263172 | 0.2 | 1.00 | 0 | 1.69 |
| ma59778s32 | 37296672 | 19.5 | 5.99 | 4.4 | 24.20 |
| ma59778119 | 37297901 | 14.1 | 5.37 | 3.2 | 22.70 |

Relevance of developed marker to chill tolerance: the identification of the candidate gene haplotype and the development of novel markers means that, with the aid of marker-supported selection, the corresponding candidate gene can be crossed within a significantly limited interval into chill-sensitive breeding material. The plants produced in this manner have an increased chill tolerance, while biodiversity is retained as far as is possible.

An analysis of 5598 genotypes from the Dent gene pool used for breeding has shown that 86% of the genotypes have the candidate gene in the desired allele variant and thus comprise the desired haplotypes.

The invention claimed is:

1. A method for the selection of a chill-tolerant maize plant, comprising the steps of
    A) isolating DNA from the genome of a maize plant,
    B) detecting an allele in a chromosomal interval flanked by the marker positions ma59778s31 and ma52594s01, and
    C) selecting a chill-tolerant maize plant or portions thereof on the basis of the detection of step B),
wherein the chill-tolerant maize plant or portion thereof comprises:
    (i) a first chromosomal interval from a donor on chromosome 4 between the marker positions ma59778s31 and ma59778119, which comprises an endogenous chill tolerance-conferring nucleic acid, and
    (ii) in a region on chromosome 4 flanked by the marker positions ma59778119 and ma52594s01, at least one further chromosomal interval from the same donor and at least one chromosomal interval which does not originate from the donor, wherein the chill tolerance-conferring nucleic acid comprises a nucleic acid sequence:
    a) selected from the group consisting of: a) a nucleic acid sequence with SEQ ID NO: 29, b) a nucleic acid sequence which has at least 98% identity with the sequence from a), c) a nucleic acid sequence which differs from a nucleic acid sequence according to a) in accordance with the degeneracy of the genetic code, d) a nucleic acid sequence which codes for a protein with SEQ ID NO: 30; and
    b) the nucleic acid sequence of a) is operatively connected with either a promoter which comprises the nucleotide sequence with SEQ ID NO: 33, or a modified form of a promoter which comprises the nucleotide sequence with SEQ ID NO: 34, wherein the modified form produces a comparable expression rate or level of expression as the promoter which comprises the nucleotide sequence with SEQ ID NO: 33, and
wherein the marker positions with reference to AGPv2 are: ma59778s31=37263172 bp; bp; ma59778119=37297901 bp; ma52594s01=58033711 bp.

2. A method for the selection of a chill-tolerant maize plant, comprising the steps of
    A) isolating DNA from the genome of a maize plant,
    B) detecting a first allele distal to the chill tolerance-conferring nucleic acid in a chromosomal interval between ma11840s01 and ma59778s31 and a second allele proximal to the chill tolerance-conferring nucleic acid in a chromosomal interval between ma59778119 and ma52594s01, and
    C) selecting a chill-tolerant maize plant or portions thereof on the basis of the detection of step B),
wherein the chill-tolerant maize plant or portion thereof comprises:
    (i) a first chromosomal interval from a donor on chromosome 4 between the marker positions ma59778s31 and ma59778119, which comprises an endogenous chill tolerance-conferring nucleic acid, and
    (ii) in a region on chromosome 4 flanked by the marker positions ma59778119 and ma52594s01, at least one further chromosomal interval from the same donor and at least one chromosomal interval which does not originate from the donor, wherein the chill tolerance-conferring nucleic acid comprises a nucleic acid sequence:
    a) selected from the group consisting of: a) a nucleic acid sequence with SEQ ID NO: 29, b) a nucleic acid sequence which has at least 98% identity with the sequence from a), c) a nucleic acid sequence which differs from a nucleic acid sequence according to a) in accordance with the degeneracy of the genetic code, d) a nucleic acid sequence which codes for a protein with SEQ ID NO: 30; and
    b) the nucleic acid sequence of a) is operatively connected with either a promoter which comprises the nucleotide sequence with SEQ ID NO: 33, or a modified form of a promoter which comprises the nucleotide sequence with SEQ ID NO: 34, wherein the modified form produces a comparable expression rate or level of expression as the promoter which comprises the nucleotide sequence with SEQ ID NO: 33, and
wherein the marker positions with reference to AGPv2 are: ma59778s31=37263172 bp; bp; ma59778119=37297901 bp; ma52594s01=58033711 bp.

3. The method of claim 1, wherein step B) comprises detecting alleles at the marker positions ma59778s31, ma59778s32 and ma59778119,
    wherein the marker position ma59778s31 is a T, the marker position ma59778s32 is a T, the marker position ma59778119 is a C, or
    wherein the marker position ma59778s31 is a C, the marker position ma59778s32 is a T, the marker position ma59778119 is a C.

* * * * *